(12) United States Patent
Chevalier et al.

(10) Patent No.: US 8,415,341 B2
(45) Date of Patent: *Apr. 9, 2013

(54) HETEROAROMATIC AND AROMATIC PIPERAZINYL AZETIDINYL AMIDES AS MONOACYLGLYCEROL LIPASE INHIBITORS

(75) Inventors: Kristen Chevalier, Collegeville, PA (US); Jose Clemente, Exton, PA (US); Scott Dax, Landenberg, PA (US); Chris Flores, Spring House, PA (US); Li Liu, Doylestown, PA (US); Mark Macielag, Spring House, PA (US); Mark McDonnell, Lansdale, PA (US); Marina Nelen, Spring House, PA (US); Erica Nulton, Spring House, PA (US); Stephen Prouty, Philadelphia, PA (US); Matthew Todd, Spring House, PA (US); Sui-Po Zhang, Radnor, PA (US); Bin Zhu, Spring House, PA (US)

(73) Assignee: Janssen Pharmaceutica, NV (BE)

( * ) Notice: Subject to any disclaimer, the term of this patent is extended or adjusted under 35 U.S.C. 154(b) by 217 days.

This patent is subject to a terminal disclaimer.

(21) Appl. No.: 12/765,617

(22) Filed: Apr. 22, 2010

(65) Prior Publication Data

US 2010/0324015 A1 Dec. 23, 2010

Related U.S. Application Data

(60) Provisional application No. 61/171,660, filed on Apr. 22, 2009, provisional application No. 61/171,661, filed on Apr. 22, 2009.

(51) Int. Cl.
*A61K 31/496* (2006.01)
*A61K 31/551* (2006.01)
*C07D 401/06* (2006.01)
*C07D 401/14* (2006.01)
*C07D 403/12* (2006.01)
*C07D 409/14* (2006.01)
*C07D 417/12* (2006.01)

(52) U.S. Cl. ............... 514/210.18; 540/575; 544/212; 544/295; 544/363; 544/364; 544/368; 544/367

(58) Field of Classification Search .............. None
See application file for complete search history.

(56) References Cited

U.S. PATENT DOCUMENTS

| | | |
|---|---|---|
| 2004/0167224 A1 | 8/2004 | Ozaki et al. |
| 2006/0148844 A1 | 7/2006 | Nakade et al. |
| 2007/0142394 A1 | 6/2007 | Solomon et al. |
| 2007/0293496 A1 | 12/2007 | Ozaki et al. |
| 2009/0269784 A1* | 10/2009 | Grasberger et al. ........... 435/7.4 |
| 2010/0041651 A1 | 2/2010 | Even et al. |

FOREIGN PATENT DOCUMENTS

| | | |
|---|---|---|
| EP | 2180048 A1 | 4/2010 |
| FR | 2915199 | 10/2008 |
| WO | WO 98/37077 A1 | 8/1998 |
| WO | WO 99/19297 A1 | 4/1999 |
| WO | WO 00/63168 A1 | 10/2000 |
| WO | WO 01/77101 A1 | 10/2001 |
| WO | WO 2004/056800 | 7/2004 |
| WO | WO 2006/097175 A1 | 9/2006 |

OTHER PUBLICATIONS

Magrioti et al. Bioorganic & Medicinal Chemistry Letters, vol. 18, p. 5424-5427 (2008).*
International Search Report and Written Opinion, PCT/US2010/032098, dated Jun. 18, 2010, 14 pages.
Benito et al., "Cannabinoid CB2 receptors in human brain inflammation", Brit J Pharmacol, 2008, vol. 153, pp. 277-285.
Behrendt, HJ et al. "Characterization of the mouse cold-menthol receptor TRPM8 and vanilloid receptor type-1 VR1 using a fluorometric imaging plate reader (FLIPR) assay", Brit J Pharmacol, 2004, vol. 141(4): pp. 737-745.
Bennett GJ, Xie YK., "A Peripheral Mononeuropathy in Rat that Produces Disorders of Pain Sensation Like Those Seen in Man", Pain, 1988, vol. 33(1), pp. 87-107.
Ben-Shabat et al., An entourage effect: inactive endogenous fatty acid glycerol esters enhance 2-arachidonoyl-glycerol cannabinoid activity, Eur J Pharmacol, 1998, vol. 353, pp. 23-31.
Cravatt et al., The Endogenous Cannabinoid System and Its Role in Nociceptive Behavior, J Neurobiol, 2004, vol. 61, pp. 149-160.
Comelli et al., "The inhibition of monoacylglycerol lipase by URB602 showed an anti-inflammatory and anti-nociceptive effect in a murine model of acute inflammation", Brit J Pharmacol, 2007, vol. 152, pp. 787-794.
Cavuoto et al.,"The expression of receptors for endocannabinoids in human and rodent skeletal muscle", Biochem Biophys Res Commun, 2007, vol. 364, pp. 105-110.
Devane et al., "Isolation and Structure of a Brain Constituent That Binds to the Cannabinoid Receptor", Science, 1992, vol. 258, pp. 1946-1949.
Di Marzo et al., "Endocannabinoids: New Targets for Drug Development", Curr Pharm Des, 2000, vol. 6, pp. 1361-1380.
Di Marzo et al., "Endocannabinoids and the Regulation of their levels in Health and Disease", Curr Opin Lipidol, 2007, vol. 18, pp. 129-140.
Dogrul et al., "'Knock-down' of spinal CB1 receptors produces abnormal pain and elevates spinal dynorphin content in mice", Pain, 2002, vol. 100, pp. 203-209.

(Continued)

*Primary Examiner* — Emily Bernhardt

(57) ABSTRACT

Disclosed are compounds, compositions and methods for treating diseases, syndromes, conditions and disorders that are affected by the inhibition of MGL, including pain. Such compounds are represented by Formula (I) as follows:

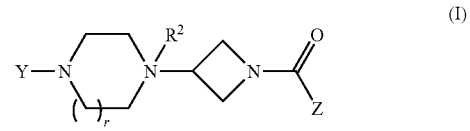

wherein Y, r, R2 and Z are defined herein.

18 Claims, No Drawings

OTHER PUBLICATIONS

Fox, A et al., "Critical evaluation of the streptozotocin model of painful diabetic neuropathy in the rat", Pain , 1999, vol. 81: pp. 307-316.

Guindon et al., Cannabinoid CB2 receptors: a therapeutic target for the treatment of inflammatory and neuropathic pain, Brit J Pharmacol, 2008, vol. 153, pp. 319-334.

Hajrasouliha et al., "Endogenous cannabinoids contribute to remote ischemic preconditioning via cannabinoid CB2 receptors in the rat heart", Eur J Pharmacol, 2008, vol. 579, pp. 246-252.

Hunter, JC et al., The effect of novel anti-epileptic drugs in rat experimental models of acute and chronic pain Eur J Pharmacol 1997 vol. 324: pp. 153-160.

Iyengar, S., et al., "Efficacy of Duloxetine, a Potent and Balanced Serotonin-Norepinephrine Reuptake Inhibitor in Persistent Pain Models in Rats", *JPET*, 2004 vol. 311:pp. 576-584.

Jhaveri et al., "Endocannabinoid metabolism and uptake: novel targets for neuropathic and inflammatory pain", Brit J Pharmacol, 2007, vol. 152, pp. 624-632.

Jorum, E et al. "Cold allodynia and hyperalgesia in neuropathic pain: the effect of N-methyl-d-aspartate (NMDA) receptor antagonist ketamine—a double-blind, cross-over comparison with alfentanil and placebo", Pain, 2003, vol. 101, pp. 229-235.

Kathuria et al., "Modulation of anxiety through blockade of anandamide hydrolysis", Nat Med, 2003, vol. 9, pp. 76-81.

Lichtman et al., "Pharmacological Activity of Fatty Acid Amides Is Regulated, but Not Mediated, by Fatty Acid Amide Hydrolase in Vivo", J Pharmacol Exp Ther, 2002, 302, 73-9.

Lichtman et al., "Mice lacking fatty acid amide hydrolase exhibit a cannabinoid receptor-mediated phenotypic hypoalgesia", Pain, 2004, vol. 109, pp. 319-27.

Matsuda et al., "Structure of a Cannabinoid Receptor and Functional Expression of the cloned cDNA", Nature, 1990, vol. 346, pp. 561-564.

Matulis et al, "Thermodynamic Stability of Carbonic Anhydrase: Measurements of Binding Affinity and Stoichiometry Using ThermoFluor", Biochemistry, 2005, vol. 44, pp. 5258-5266.

McCarberg B. et al., "The Future of Cannabinoids as Analgesic Agents: A Pharmacologic, Pharmacokinetic, and Pharmacodynamic Overview", Amer J Ther, 2007, vol. 14, pp. 475-483.

Mechoulam et al., "Identification of an Endogenous 2-Monoglyceride, Present in Canine Gut, that Binds to Cannabinoid Receptors", Biochem Pharmacol, 1995, vol. 50, pp. 83-90.

Munro et al., "Molecular Characterization of a Peripheral Receptor for Cannabinoids", Nature, 1993, vol. 365, pp. 61-65.

Njie, Ya Fatou et al, "Aqueous humor outflow effects of 2-arachidonylglycerol", Exp. Eye Res., 2008, vol. 87(2), pp. 106-114.

Pacher et al., "Pleiotropic effects of the $CB_2$ cannabinoid receptor activation on human monocyte migration: implications for atherosclerosis and inflammatory diseases", Amer J Physiol, 2008, vol. 294, pp. H1133-H1134.

Pantoliano, M. W. et al., "High-Density Miniaturized Thermal Shift Assays as a General Strategy for Drug Discovery", J Biomol Screen, 2001, vol. 6, pp. 429-440.

Pertwee, The diverse CB1 and CB2 receptor pharmacology of three plant cannabinoids: $\Delta^9$-tetrahydrocannabinol, cannabidiol and $\Delta^9$-tetrahydrocannabivarin, Brit J Pharmacol, 2008, vol. 153, pp. 199-215.

Piomelli, "The Molecular Logic of Endocannabinoid Signalling", Nat Rev Neurosci, 2003, vol. 4, pp. 873-884.

Pomonis, JD et al., "*N*-(4-Tertiarybutylphenyl)-4-(3-cholorphyridin-2-yl)tetrahydropyrazine-1(2*H*)-carbox-amide (BCTC), a Novel, Orally Effective Vanilloid Receptor 1 Antagonist with Analgesic Properties: II. In Vivo Characterization in Rat Models of Inflammatory and Neuropathic Pain", *JPET*, 2003, vol. 306:pp. 387-393.

Sugiura et al., "2-Arachidonoylglycerol: A Possible Endogenous Cannabinoid Receptor Ligand in Brain", Biochem Biophys Res Commun, 1995, vol. 215, pp. 89-97.

Suzuki, R et al., "The effectiveness of spinal and systemic morphine on rat dorsal horn neuronal responses in the spinal nerve ligation model of neuropathic pain", Pain, 1999, vol. 80: pp. 215-228.

Walker et al., "Pain modulation by release of the endogenous cannabinoid anandamide", Proc Natl Acad Sci USA, 1999, vol. 96, pp. 12198-12203.

Yaksh, TL et al., "Vincristine-induced allodynia in the rat", Pain, 2001, vol. 93: pp. 69-76.

Tammpere et al., "Evaluation of pseudo-affective responses to noxious 10 colorectal distension in rats by manometric recordings.", Pain, 2005, pp. 220-226, vol. 116.

Ness et al., "Colorectal distension as a noxious visceral stimulus: physiologic and pharmacologic characterization of pseudaffective reflexes in the rat.", Brain Research, 1988, pp. 153-169, vol. 450.

* cited by examiner

HETEROAROMATIC AND AROMATIC PIPERAZINYL AZETIDINYL AMIDES AS MONOACYLGLYCEROL LIPASE INHIBITORS

CROSS REFERENCE TO RELATED APPLICATIONS

This application claims the benefit of U.S. Provisional Application No. 61/171,660, filed on Apr. 22, 2009, which is incorporated by reference herein in its entirety.

This application is related to provisional application entitled, Heteroaromatic and Aromatic piperazinyl Azetidinyl Amides as Monoacylglycerol Lipase Inhibitors, U.S. Provisional Application No. 61/171,661, filed on Apr. 22, 2009.

STATEMENT REGARDING FEDERALLY SPONSORED RESEARCH OR DEVELOPMENT

The research and development of the invention described below was not federally sponsored.

FIELD OF THE INVENTION

The present invention is directed to novel monoacylglycerol lipase (MGL) inhibitors, pharmaceutical compositions containing them and their use in the treatment, amelioration and/or prevention of an MGL disorder in a subject, including a mammal and/or human, in which the disease, syndrome, or condition is affected by MGL.

BACKGROUND OF THE INVENTION

*Cannabis sativa* has been used for the treatment of pain for many years. $\Delta^9$-tetrahydrocannabinol is a major active ingredient from *Cannabis sativa* and an agonist of cannabinoid receptors (Pertwee, *Brit J Pharmacol*, 2008, 153, 199-215). Two cannabinoid G protein-coupled receptors have been cloned, cannabinoid receptor type 1 ($CB_1$, Matsuda et al., *Nature*, 1990, 346, 561-4) and cannabinoid receptor type 2 ($CB_2$, Munro et al., *Nature*, 1993, 365, 61-5). $CB_1$ is expressed centrally in brain areas, such as the hypothalamus and nucleus accumbens, as well as peripherally in the liver, gastrointestinal tract, pancreas, adipose tissue and skeletal muscle (Di Marzo et al., *Curr Opin Lipidol*, 2007, 18, 129-140). $CB_2$ is predominantly expressed in immune cells, such as monocytes (Pacher et al., *Amer J Physiol*, 2008, 294, H1133-H1134), and, under certain conditions, also in the brain (Benito et al., *Brit J Pharmacol*, 2008, 153, 277-285) and in skeletal (Cavuoto et al., *Biochem Biophys Res Commun*, 2007, 364, 105-110) and cardiac (Hajrasouliha et al., *Eur J Pharmacol*, 2008, 579, 246-252) muscle. An abundance of pharmacological, anatomical and electrophysiological data, using synthetic agonists, indicate that increased cannabinoid signaling through $CB_1/CB_2$ promotes analgesia in tests of acute nociception and suppresses hyperalgesia and/or allodynia in models of chronic neuropathic and inflammatory pain (Cravatt et al., *J Neurobiol*, 2004, 61, 149-60; Guindon et al., *Brit J Pharmacol*, 2008, 153, 319-334).

Efficacy of synthetic cannabanoid receptor agonists is well documented. Moreover, studies using cannabinoid receptor antagonists and knockout mice have also implicated the endocannabinoid system as an important modulator of nociception. Anandamide (AEA) (Devane et al., *Science*, 1992, 258, 1946-9) and 2-arachidinoylglycerol (2-AG) (Mechoulam et al., *Biochem Pharmacol*, 1995, 50, 83-90; Sugiura et al., *Biochem Biophys Res Commun*, 1995, 215, 89-97) are two major endocannabinoids. AEA is hydrolyzed by fatty acid amide hydrolase (FAAH) and 2-AG is hydrolyzed by monoacylglycerol lipase (MGL) (Piomelli, *Nat Rev Neurosci*, 2003, 4, 873-884). Genetic ablation of FAAH elevates endogenous AEA and results in a $CB_1$-dependent analgesia in models of acute and inflammatory pain (Lichtman et al., *Pain*, 2004, 109, 319-27), suggesting that the endocannabinoid system functions naturally to inhibit nociception (Cravatt et al., *J Neurobiol*, 2004, 61, 149-60). Unlike the constitutive increase in endocannabinoid levels using FAAH knockout mice, use of specific FAAH inhibitors transiently elevates AEA levels and results in antinociception in vivo (Kathuria et al., *Nat Med*, 2003, 9, 76-81). Further evidence for an endocannabinoid-mediated antinociceptive tone is demonstrated by the formation of AEA in the periaqueductal gray, a known pain center, following noxious stimulation in the periphery (Walker et al., *Proc Natl Acad Sci USA*, 1999, 96, 12198-203) and, conversely, by the induction of hyperalgesia following the administration of $CB_1$ antisense RNA in the spinal cord (Dogrul et al., *Pain*, 2002, 100, 203-9).

With respect to 2-AG, intravenous delivery produces analgesia in the tail flick (Mechoulam et al., *Biochem Pharmacol*, 1995, 50, 83-90) and hot plate (Lichtman et al., *J Pharmacol Exp Ther*, 2002, 302, 73-9) assays. In contrast, it was demonstrated that 2-AG given alone is not analgesic in the hot plate assay, but when combined with other 2-monoacylglycerols (i.e., 2-linoleoyl glycerol and 2-palmitoyl glycerol), significant analgesia is attained, a phenomenon known as the "entourage effect" (Ben-Shabat et al., *Eur J Pharmacol*, 1998, 353, 23-31). These "entourage" 2-monoacylglycerols are endogenous lipids that are co-released with 2-AG and potentiate endocannabinoid signaling, in part, by inhibiting 2-AG breakdown, most likely by competition for the active site on MGL. This suggests that synthetic MGL inhibitors will have a similar effect. Indeed, URB602, a relatively weak synthetic MGL inhibitor, showed an antinociceptive effect in a murine model of acute inflammation (Comelli et al., *Brit J Pharmacol*, 2007, 152, 787-794).

Although the use of synthetic cannabinoid agonists have conclusively demonstrated that increased cannabinoid signaling produces analgesic and anti-inflammatory effects, it has been difficult to separate these beneficial effects from the unwanted side effects of these compounds. An alternative approach is to enhance the signaling of the endocannabinoid system by elevating the level of 2-AG, the endocannabinoid of highest abundance in the central nervous system (CNS) and gastrointestinal tract, which may be achieved by inhibition of MGL. Therefore, MGL inhibitors are potentially useful for the treatment of pain, inflammation and CNS disorders (Di Marzo et al., *Curr Pharm Des*, 2000, 6, 1361-80; Jhaveri et al., *Brit J Pharmacol*, 2007, 152, 624-632; McCarberg Bill et al., *Amer J Ther*, 2007, 14, 475-83), as well as glaucoma and disease states arising from elevated intraocular pressure (Njie, Ya Fatou; He, Fang; Qiao, Xhuanhong; Song, Zhoa-Hui, *Exp. Eye Res.*, 2008, 87(2):106-14).

SUMMARY OF THE INVENTION

The present invention is directed to a compound of formula (I)

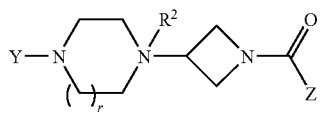

or an enantiomer, diastereomer, solvate, or pharmaceutically acceptable salts thereof; wherein Y is phenyl or a heteroaryl selected from the group consisting of thiazolyl, pyridyl, pyrimidinyl, 1,3,5-triazinyl, benzoxazolyl, benzisoxazolyl, benzothiazolyl, and 1,3,4-thiadiazolyl;

wherein the phenyl or heteroaryl is optionally substituted with one substituent selected from the group consisting of fluoro, chloro, bromo, iodo, $C_{1-4}$alkyl, trifluoromethyl, $C_{1-4}$alkoxy, $C_{1-4}$alkylthio, nitro and cyano;

r is an integer from 1 to 2;

$R^2$ is absent or is oxo;

Z is selected from the group consisting of (a) phenyl substituted with $NR^a R^b$;
wherein $R^a$ is hydrogen or $C_{1-4}$alkyl; wherein $R^b$ is $C_{1-4}$alkyl, cycloalkyl, phenyl, furanylmethyl, or phenyl($C_{1-2}$alkyl); and wherein the phenyl of $R^b$, the phenyl of phenyl($C_{1-2}$alkyl) of $R^b$, or the furanyl of furanylmethyl of $R^b$ are optionally substituted with an iodo substituent; alternatively, $R^a$ and $R^b$ are taken together with the nitrogen atom to which they are both bound to form a 5 to 8 membered heterocyclyl, which heterocyclyl is optionally fused to a benzo group;

(b) biphenyl-3-yl or biphenyl-4-yl; wherein the interior phenyl ring, attached to the carbonyl of Formula (I) is optionally substituted with a fluoro substituent; and wherein the terminal phenyl ring is optionally substituted with a substituent selected from the group consisting of trifluoromethyl, $C_{1-4}$alkoxy, chloro, dichloro, fluoro, and iodo;

(c) phenyl substituted with a substituent selected from the group consisting of $C_{5-8}$cycloalkyl, —NHC(=O)cyclohexyl, phenyloxy, phenylcarbonyl, phenyl($C_{1-3}$)alkyl, phenyl($C_{1-3}$)alkoxy, pyrrolyl, pyrazolyl, imidazolyl, isoindol-2-yl-1,3-dione, 2,3-dihydro-isoindol-2-yl; 1-(t-butoxycarbonyl)piperidin-4-yloxy, and 1-(t-butoxycarbonyl)piperidin-4-yl;

(d) phenyl substituted with one to two substituents independently selected from the group consisting of $C_{1-6}$alkyl, $C_{1-4}$alkoxy, iodo, chloro and nitro;

(e) phenyl($C_{1-2}$)alkyl-; wherein the phenyl is optionally substituted with one to two substituent independently selected from the group consisting of iodo, fluoro, $C_{1-6}$alkyl, phenyl, and $NR^c R^d$; wherein $R^c$ is hydrogen or $C_{1-4}$alkyl; and wherein $R^d$ is $C_{1-4}$alkyl or $C_{3-6}$cycloalkyl($C_{1-4}$alkyl; and wherein the $C_{1-2}$alkyl of phenyl($C_{1-2}$)alkyl is optionally substituted with phenyl;

(f) phenyl($C_{2-4}$)alkenyl-; wherein the phenyl is optionally substituted with a substituent selected from the group consisting of $C_{1-4}$alkyl, $C_{1-4}$alkoxy, trifluoromethyl, trifluoromethylthio and phenyl;

(g) naphthyl; wherein the naphthyl is optionally substituted with one $C_{1-4}$alkoxy substituent;

(h) fluorenyl or xanthenyl; wherein the fluorenyl or xanthenyl is optionally substituted with oxo;

(i) $C_{5-8}$cycloalkyl; wherein the $C_{5-8}$cycloalkyl is optionally substituted with one $C_{1-6}$alkyl substituent;

(j) benzofused $C_{5-8}$cycloalkyl or benzofused $C_{5-8}$cycloalkyl($C_{1-4}$)alkyl; wherein said $C_{5-8}$cycloalkyl portion is optionally substituted with 1 to 4 methyl substituents;

(k) bicyclo[2.2.2]octyl-1-yl; wherein the bicyclo[2.2.2]octyl-1-yl is optionally substituted with $C_{1-6}$alkyl;

(l) a heteroaryl or benzo-fused heteroaryl selected from the group consisting of benzoxazolyl, quinolinyl, benzimidazolyl, pyridinyl, indolyl, thienyl, furanyl, pyrazolyl, oxazolyl, benzothienyl, and benzofuranyl;
wherein the heteroaryl or benzo-fused heteroaryl is optionally substituted with one to two substituents independently selected from the group consisting of $C_{1-4}$alkyl, trifluoromethyl, $C_{5-8}$cycloalkyl, phenyl, phenyl($C_{1-2}$)alkoxy, phenyl($C_{2-4}$)alkynyl and dichlorophenoxy; and wherein the phenyl substituent on the heteroaryl is further optionally substituted with a substituent selected from $C_{1-4}$alkyl, $C_{1-4}$alkoxy or trifluoromethyl;

(m) 1,5-diphenyl-1H-pyrazol-3-yl; wherein the pyrazol-3-yl is optionally substituted with a methyl substituent; and wherein each of the phenyl groups of the 1,5-diphenyl substituents is further optionally substituted with a substituent selected from chloro, dichloro or aminosulfonyl;

(n) 1,2,3,4-tetrahydro-quinolin-6-yl; wherein the 1,2,3,4-tetrahydro-quinolin-6-yl is optionally substituted with phenyl or trifluoromethyl substituted phenyl; and (o) benzofused heterocyclyl($C_{2-4}$)alkenyl; wherein the benzofused heterocyclyl is attached to the $C_{2-4}$alkenyl via the benzo ring; and wherein benzofused heterocyclyl is further optionally substituted with $C_{5-6}$cycloalkyl;

with the proviso that the compound of formula (I) is other than a compound wherein Y is 3-methylpyridin-2-yl, r is 1, and $R^2$ is absent and Z is 4-biphenyl;

a compound wherein Y is pyridin-2-yl, r is 1, and $R^2$ is absent and Z is 2-(phenylcarbonyl)phenyl;

a compound wherein Y is 5-trifluoromethylpyridin-2-yl, r is 1, and $R^2$ is absent and Z is 4-cyclohexyl-phenyl;

a compound wherein Y is pyridin-2-yl, r is 1, and $R^2$ is absent and Z is 3-(cyclohexylcarbonylamino)phenyl;

a compound wherein Y is 5-cyanopyridin-2-yl, r is 1, and $R^2$ is absent and Z is 4-biphenyl;

a compound wherein Y is 5-trifluoromethylpyridin-2-yl, r is 1, and $R^2$ is absent and Z is 4-biphenyl;

a compound wherein Y is pyrimidin-2-yl, r is 2, and $R^2$ is absent and Z is 2-(4-trifluoromethylthiophenyl)-vinyl;

a compound wherein Y is pyridin-2-yl, r is 1, and $R^2$ is absent and Z is 2-phenyl-vinyl;

a compound wherein Y is pyridin-2-yl, r is 1, and $R^2$ is absent and Z is 2-phenylethyl;

a compound wherein Y is pyridin-2-yl, r is 1, and $R^2$ is absent and Z is 2-t-butyl-benzoxazol-6-yl;

a compound wherein Y is pyridin-2-yl, r is 1, and $R^2$ is absent and Z is 2-(4-methoxyphenyl)-benzoxazol-7-yl;

a compound wherein Y is pyridin-2-yl, r is 1, and $R^2$ is absent and Z is 2-cyclohexyl-benzoxazol-6-yl;

a compound wherein Y is pyridin-2-yl, r is 1, and $R^2$ is absent and Z is 1,2-diisobutyl-1H-indol-5-yl;

a compound wherein Y is pyridin-2-yl, r is 1, and $R^2$ is absent and Z is 1-methyl-2-propyl-1H-indol-5-yl;

a compound wherein Y is pyridin-2-yl, r is 1, and $R^2$ is absent and Z is 1-isobutyl-2-phenyl-1H-indol-5-yl;

a compound wherein Y is pyridin-2-yl, r is 1, and R² is absent and Z is 1-isobutyl-2-(4-methylphenyl)-1H-indol-5-yl;

a compound wherein Y is pyridin-2-yl, r is 1, and R² is absent and Z is 2-(3-methoxyphenyl)-benzoxazol-5-yl;

a compound wherein Y is pyridin-2-yl, r is 1, and R² is absent and Z is 2-benzylphenyl;

a compound wherein Y is pyridin-2-yl, r is 1, and R² is absent and Z is (1R)-1,2,3,4-tetrahydronaphthalen-1-yl;

a compound wherein Y is pyridin-2-yl, r is 1, and R² is absent and Z is (1S)-1-[4-(2-methylpropyl)phenyl]ethyl;

a compound wherein Y is pyridin-2-yl, r is 1, and R² is absent and Z is (1S)-1-(2-fluoro-[1,1'-biphenyl]-4-yl)ethyl;

a compound wherein Y is pyridin-2-yl, r is 1, and R² is absent and Z is 2,3-dihydro-1H-inden-2-yl;

a compound wherein Y is pyridin-2-yl, r is 1, and R² is absent and Z is 2,2-diphenylethyl; or a compound wherein Y is 3-trifluoromethylphenyl, r is 1, and R² is absent and Z is 1,2,3,4-tetrahydroquinolin-6-yl.

The present invention is further directed to the use of a compound of formula (I) as herein defined, as an inhibitor of MGL for the treatment or amelioration or prevention of a disorder, disease, syndrome, or condition that is affected by the inhibition of MGL.

The present invention further provides methods for treating, ameliorating and/or preventing a disorder, disease, syndrome, or condition that is affected by the inhibition of MGL such as pain, the diseases that lead to such pain, inflammation and CNS disorders comprising, consisting of and/or consisting essentially of administering to a subject in need thereof, a therapeutically effective amount of a compound of Formula (I) as herein defined.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I) as herein defined, or a pharmaceutically acceptable salt form thereof.

Also provided are processes for making a pharmaceutical composition comprising, consisting of, and/or consisting essentially of admixing a compound of Formula (I) as herein defined, and a pharmaceutically acceptable carrier, a pharmaceutically acceptable excipient, and/or a pharmaceutically acceptable diluent.

The present invention is further directed to the use of a compound of formula (I) as herein defined for the preparation of a medicament or a pharmaceutical composition for the treatment, amelioration and/or prevention of a disease, syndrome, condition or disorder that is affected by the inhibition of MGL, in a subject in need thereof.

The present invention also provides methods for producing the compounds of Formula (I) as herein defined, and pharmaceutical compositions and medicaments thereof.

DETAILED DESCRIPTION OF THE INVENTION

The term "alkyl" whether used alone or as part of a substituent group, refers to straight and branched carbon chains having 1 to 8 carbon atoms. Therefore, designated numbers of carbon atoms (e.g. $C_{1-8}$) refer independently to the number of carbon atoms in an alkyl moiety or to the alkyl portion of a larger alkyl-containing substituent. In substituent groups with multiple alkyl groups such as $(C_{1-6}alkyl)_2amino$- the $C_{1-6}alkyl$ groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond. One skilled in the art will further recognize that the term "vinyl" and "ethenyl" are interchangeable are used to designate a $C_2$alkenyl substituent group.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl and adamantyl.

The term "benzo-fused cycloalkyl" refers to a 5 to 8 membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members and which contains carbon atoms and from 1 to 4 heteroatoms independently selected from the group consisting of N, O, and S. Included within the term heterocyclyl is a nonaromatic cyclic ring of 5 to 7 members in which 1 to 2 members are nitrogen, or a nonaromatic cyclic ring of 5 to 7 members in which zero, one or two members are nitrogen and up to two members are oxygen or sulfur and at least one member must be either nitrogen, oxygen or sulfur; wherein, optionally, the ring contains zero to one unsaturated bonds, and, optionally, when the ring is of 6 or 7 members, it contains up to two unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from the group consisting of N, O, and S. The carbon atom ring members that form the heterocycle ring may be fully saturated or partially saturated. Unless otherwise noted, benzo-fused heterocycle ring is attached to its pendant group at a carbon atom of the benzene ring.

The term "aryl" refers to an unsaturated, aromatic monocyclic or bicyclic ring of 6 to 10 carbon members. Examples of aryl rings include phenyl and naphthyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to three additional nitrogens. In the case of 6 membered rings, the heteroaryl ring preferably contains from one to three nitrogen atoms. For the case wherein the 6 membered ring has three nitrogens, at most two nitrogen atoms are adjacent. When a heteroaryl is bicyclic, at least one heteroatom is present in each ring. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl and pyrazinyl. Unless otherwise noted, the heteroaryl is attached to its pendant group at any heteroatom or carbon atom that results in a stable structure.

Unless otherwise noted, the term "benzo-fused heteroaryl" refers to a 5 to 6 membered monocyclic heteroaryl ring fused to a benzene ring. The heteroaryl ring contains carbon atoms and from 1 to 4 heteroatoms independently selected from the group consisting of N, O, and S. Examples of heteroaryl groups with the optionally fused benzene rings include indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the benzo-fused heteroaryl is attached to its pendant group at any heteroatom or carbon atom that results in a stable structure.

The term "halogen" or "halo" refers to fluorine, chlorine, bromine and iodine.

The term "formyl" refers to the group —C(=O)H.

The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

With reference to substituents, the term "independently" means that when more than one substituent is possible, the substituents may be the same or different from each other.

Unless otherwise noted, it is intended that the definition of any substituent or variable at a particular location in a molecule be independent of its definitions elsewhere in that molecule. It is understood that substituents and substitution patterns on the compounds of formula (I) can be selected by one of ordinary skill in the art to provide compounds that are chemically stable and that can be readily synthesized by techniques known in the art as well as those methods set forth herein.

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

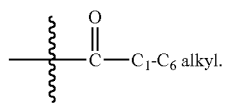

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Abbreviations used in the specification, particularly the Schemes and Examples, are as follows:
DCC=N,N-Dicyclohexylcarbodiimide
DCM=Dichloromethane
DIPEA=Diisopropylethylamine
DMF=N,N-Dimethylformamide
DMSO=Dimethylsulfoxide
EDTA=Ethylene Diamine Tetraacetic Acid
EtOAc=Ethyl acetate
h=hour(s)
HATU=O-(7-Azabenzotriazol-1-yl)-N,N,N",N"-Tetramethyl Uronium Hexafluorophosphate
HBTU=O-Benzotriazol-1-yl-N,N,N',N'-Tetramethyl-Uronium-Hexafluoro-phosphate
HEPES=4-(2-Hydroxyethyl)-1-piperazine Ethane Sulfonic Acid
HPLC=High Performance Liquid Chromatography
min=minute(s)
MPLC=Medium Pressure Liquid Chromatography
mCPBA=m-chloroperoxybenzoic acid
PIPES=piperazine-N,N'-bis(2-ethanesulfonic acid
sec=second(s)
TEA=Triethylamine
THF=Tetrahydrofuran The term "subject" as used herein, refers to an animal, preferably a mammal, most preferably a human, who has been the object of treatment, observation or experiment.

The term "therapeutically effective amount" as used herein, refers to an amount of an active compound or pharmaceutical agent that elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

As used herein, the term "composition" is intended to encompass a product comprising the specified ingredients in therapeutically effective amounts, as well as any product that results, directly or indirectly, from combinations of the specified ingredients in the specified amounts.

As used herein, unless otherwise noted, the terms "treating", "treatment", "ameliorating" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the terms "preventing" and "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical professional to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme, such as, for example, pain and the diseases that lead to such pain as well as inflammation and CNS disorders.

As used herein, unless otherwise noted, the term "affect" or "affected" (when referring to a disease, syndrome, condition or disorder that is affected by inhibition of MGL) shall imply a reduction in the frequency and/or severity of one or more symptoms or manifestations of said disease, syndrome, condition or disorder; and/or imply the prevention of the development of one or more symptoms or manifestations of said disease, syndrome, condition or disorder or the development of the disease, condition, syndrome or disorder.

The compounds of Formula (I) as herein defined, are useful in methods for treating, ameliorating and/or preventing a disease, a syndrome, a condition or a disorder that is affected by the inhibition of MGL. Such methods comprise, consist of and/or consist essentially of administering to a subject, including an animal, a mammal, and a human in need of such treatment, amelioration and/or prevention, a therapeutically effective amount of a compound of Formula (I), as herein defined, or an enantiomer, diastereomer, solvate or pharmaceutically acceptable salt thereof. In particular, the compounds of formula (I) are useful for treating, ameliorating and/or preventing pain; diseases, syndromes, conditions, or disorders causing such pain; inflammation and/or CNS disorders. More particularly, the compounds of Formula (I) as herein defined, are useful for treating, ameliorating and/or preventing inflammatory pain, inflammatory hypersensitivity conditions and/or neuropathic pain, comprising administering to a subject in need thereof a therapeutically effective amount of a compound of Formula (I), as herein defined, as herein defined.

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease, ulcerative colitis, urinary incontinence, benign prostatic hypertrophy, cough, asthma, rhinitis, nasal hypersensitivity, itch, contact dermititis and/or dermal allegry and chronic obstructive pulmonary disease.

In an embodiment, the present invention is directed to a method for treating, ameliorating and/or preventing inflammatory visceral hyperalgesia in which a enhanced visceral irritability exists, comprising, consisting of, and/or consisting essentially of the step of administering to a subject in need of such treatment a therapeutically effective amount of a compound, salt or solvate of formula (I). In a further embodiment, the present invention is directed to a method for treating inflammatory somatic hyperalgesia in which a hypersensitivity to thermal, mechanical and/or chemical stimuli exists, comprising administering to a mammal in need of such treatment a therapeutically effective amount of a compound of formula (I) or an enantiomer, diastereomer, solvate or pharmaceutically acceptable salt thereof.

A further embodiment of the present invention is directed to a method for treating, ameliorating and/or preventing neuropathic pain. Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising, consisting of, and/or consisting essentially of the step of administering to a subject in need of such treatment a therapeutically effective amount of a compound of Formula (I) as herein defined, or an enantiomer, diastereomer, solvate or pharmaceutically acceptable salt thereof.

In a further embodiment, the present invention is directed to a method for treating, ameliorating and/or preventing CNS disorders. Examples of CNS disorders include anxieties, such as social anxiety, post-traumatic stress disorder, phobias, social phobia, special phobias, panic disorder, obsessive-compulsive disorder, acute stress disorder, separation anxiety disorder, and generalized anxiety disorder, as well as depression, such as major depression, bipolar disorder, seasonal affective disorder, post natal depression, manic depression, and bipolar depression.

The present invention is directed to a compound of formula (I)

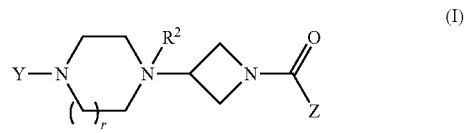

or an enantiomer, diastereomer, solvate, or a pharmaceutically acceptable salt thereof as described in more detail herein; wherein the compound of formula (I) is useful for treating, ameliorating and/or preventing a disease, syndrome, condition or disorder that is affected by the inhibition of MGL.

In an embodiment, the present invention is directed to any single compound or subset of compounds selected from the representative compounds listed in Tables 1-2 below, or enantiomers, diastereomers, solvates or pharmaceutically acceptable salts thereof. Additional embodiments of the present invention, include compounds of Formula (I) as herein defined or enantiomers, diastereomers, solvates or pharmaceutically acceptable salts thereof wherein the substituents selected for one or more of the variables defined herein (e.g. Y, r, $R^2$, Z, etc.) are independently selected to be any individual substituent or any subset of substituents selected from the complete list as defined herein. Additional embodiments of the present invention, include compounds of Formula (I) as herein defined, or enantiomers, diastereomers, solvates or pharmaceutically acceptable salts thereof wherein the substituents selected for one or more of the variables defined herein (e.g. Y, r, $R^2$, Z, etc.) are independently selected to be any individual substituent or any subset of substituents from those exemplified in the listings in Tables 1-2, below.

Representative compounds of Formula (I) as herein defined, of the present invention are as listed in Tables 1 and 2, below.

TABLE 1

Representative Compounds of Formula (I)

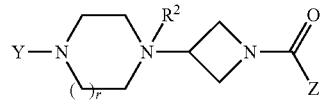

| Cmpd No. | Y | r | $R^2$ | Z |
|---|---|---|---|---|
| 1 | pyrid-2-yl | 1 | absent | 4-(N-methyl-N-cyclohexyl-amino)-phenyl |
| 2 | pyrimidin-2-yl | 1 | absent | 4-(pyrrolidin-1-yl)-phenyl |
| 3 | pyrid-2-yl | 1 | absent | 4-(1-azepanyl)-phenyl |
| 4 | pyrimidin-2-yl | 1 | absent | 4-(3-trifluoromethyl-phenyl)-phenyl |
| 5 | pyrimidin-2-yl | 1 | absent | 4-(4-methoxyphenyl)-phenyl |
| 6 | thiazol-2-yl | 1 | absent | 4-cyclohexyl-phenyl |
| 7 | pyrimidin-2-yl | 1 | absent | 4-(N-(2-iodobenzyl)-amino)-phenyl |
| 8 | pyrimidin-2-yl | 1 | absent | 4-(2-chlorophenyl)-phenyl |
| 9 | pyrimidin-2-yl | 1 | absent | 4-(4-fluorophenyl)-phenyl |
| 11 | pyrimidin-2-yl | 1 | absent | 4-(3,4-dichlorophenyl)-phenyl |
| 12 | pyrimidin-2-yl | 1 | absent | biphen-4-yl |
| 13 | pyrimidin-2-yl | 1 | absent | 4-cyclohexyl-phenyl |
| 15 | pyrid-2-yl | 1 | absent | 4-cyclohexyl-phenyl |
| 18 | pyrid-2-yl | 1 | absent | 4-(N-methyl-N-phenyl-amino)-phenyl |
| 19 | pyrimidin-2-yl | 1 | absent | 4-(4-iodophenyl)-phenyl |
| 20 | pyrimidin-2-yl | 1 | absent | 4-phenyloxy-phenyl |
| 21 | 3-cyano-pyrid-2-yl | 1 | absent | 4-cyclohexyl-phenyl |
| 22 | pyrimidin-2-yl | 1 | absent | 4-(N-(5-iodo-furan-2-ylmethyl)amino)-phenyl |

TABLE 1-continued

Representative Compounds of Formula (I)

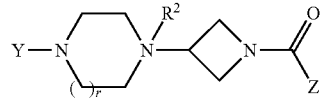

| Cmpd No. | Y | r | R² | Z |
|---|---|---|---|---|
| 23 | 3-cyano-pyrid-2-yl | 1 | absent | biphen-4-yl |
| 24 | pyrimidin-2-yl | 1 | absent | 4-benzyl-phenyl |
| 25 | pyrimidin-2-yl | 1 | absent | 4-(pyrrol-1-yl)-phenyl |
| 26 | pyrimidin-2-yl | 1 | absent | 4-(3-fluorophenyl)-phenyl |
| 27 | pyrid-2-yl | 1 | absent | 4-(N-cyclohexylcarbonyl-amino)-phenyl |
| 28 | pyrimidin-2-yl | 1 | absent | 4-dimethylamino-phenyl |
| 30 | pyrid-2-yl | 1 | absent | 4-benzyl-phenyl |
| 32 | 1,3,5-triazin-2-y1 | 1 | absent | 4-cyclohexyl-phenyl |
| 33 | benzisoxazol-3-yl | 1 | absent | 4-cyclohexyl-phenyl |
| 34 | 5-trifluoromethyl-1,3,4-thiadiazol-2-yl | 1 | absent | 4-cyclohexyl-phenyl |
| 35 | pyrid-2-yl | 1 | absent | 4-butyl-phenyl |
| 36 | thiazol-2-yl | 1 | absent | biphen-4-yl |
| 37 | pyrid-2-yl | 1 | absent | 4-diethylamino-phenyl |
| 38 | pyrimidin-2-yl | 1 | absent | 3-iodo-4-methoxy-phenyl |
| 42 | pyrid-2-yl | 1 | absent | biphen-4-yl |
| 43 | pyrimidin-2-yl | 1 | absent | 3-iodo-4-chloro-phenyl |
| 44 | pyrid-2-yl | 1 | absent | 4-(1,1-dimethyl-propyl)-phenyl |
| 45 | pyrid-2-yl | 1 | absent | 4-(phenyloxy)-phenyl |
| 46 | pyrimidin-2-yl | 1 | absent | 4-(pyrazol-1-yl)-phenyl |
| 47 | pyrid-2-yl | 1 | absent | 3-(phenyloxy)-phenyl |
| 48 | pyrimidin-2-yl | 1 | absent | 3-iodo-4-methyl-phenyl |
| 50 | pyrimidin-2-yl | 1 | absent | 3-methyl-4-iodo-phenyl |
| 52 | pyrid-2-yl | 1 | absent | 3-(4-fluorophenyl)-phenyl |
| 53 | pyrimidin-2-yl | 1 | absent | 4-iodophenyl |
| 56 | 5-chloro-pyrid-2-yl | 1 | absent | 4-cyclohexyl-phenyl |
| 58 | pyrid-2-yl | 1 | absent | 2-(benzyloxy)-phenyl |
| 60 | pyrid-2-yl | 1 | absent | 4-(3-fluorophenyl)-phenyl |
| 66 | benzoxazol-2-yl | 1 | absent | 4-cyclohexyl-phenyl |
| 67 | pyrid-2-yl | 1 | absent | biphen-3-yl |
| 69 | pyrimidin-2-yl | 1 | oxo | biphen-4-yl |
| 71 | pyrimidin-2-yl | 1 | absent | 4-(imidazol-1-yl)-phenyl |
| 73 | pyrid-2-yl | 1 | absent | biphen-4-yl |
| 74 | pyrid-2-yl | 1 | absent | 4-(phenylcarbonyl)-phenyl |
| 75 | 4-methyl-pyrid-2-yl | 1 | absent | 4-cyclohexyl-phenyl |
| 76 | pyrid-2-yl | 1 | absent | 2-(isoindolyl-1,3-dione)-phenyl |
| 77 | 5-bromo-pyrid-2-yl | 1 | absent | 4-cyclohexyl-phenyl |
| 79 | 3-chloro-pyrid-2-yl | 1 | absent | 4-cyclohexyl-phenyl |
| 81 | pyrid-2-yl | 1 | absent | 3-(2,3-dihydro-1H-isoindol-2-yl)-phenyl |
| 82 | 3-trifluoromethyl-pyrid-2-yl | 1 | absent | 4-cyclohexyl-phenyl |
| 83 | pyrimidin-2-yl | 2 | absent | biphen-4-yl |
| 85 | 5-bromo-pyrid-2-yl | 1 | absent | biphen-4-yl |
| 86 | pyrid-2-yl | 1 | absent | 3-(phenylcarbony1)-phenyl |
| 87 | pyrimidin-2-yl | 2 | absent | 4-(pyrrolidin-l-yl)-phenyl |
| 88 | pyrid-2-yl | 1 | absent | biphen-4-yl |
| 89 | 2-methoxy-phenyl | 1 | absent | biphen-4-yl |
| 90 | benzoxazol-2-yl | 1 | absent | biphen-4-yl |
| 91 | 2-methylthio-phenyl | 1 | absent | biphen-4-yl |
| 93 | 5-cyano-pyrid-2-yl | 1 | absent | 4-cyclohexyl-phenyl |
| 94 | pyrimidin-2-yl | 1 | absent | 4-nitrophenyl |
| 98 | 3-iodo-pyrid-2-yl | 1 | absent | 4-cyclohexyl-phenyl |
| 100 | 3-methyl-pyrid-2-yl | 1 | absent | 4-cyclohexyl-phenyl |
| 101 | 3-trifluoromethyl-pyrid-2-yl | 1 | absent | biphen-4-yl |
| 102 | 4-methyl-pyrid-2-yl | 1 | absent | biphen-4-yl |
| 104 | benzothiazol-2-yl | 1 | absent | 4-cyclohexyl-phenyl |
| 105 | 2-nitro-phenyl | 1 | absent | biphen-4-yl |
| 106 | benztohiazol-2-yl | 1 | absent | biphen-4-yl |
| 109 | pyrid-2-yl | 1 | absent | 3-(phenyloxy)-phenyl |
| 110 | pyrimidin-2-yl | 2 | absent | 4-benzyl-phenyl |
| 111 | pyrimidin-2-yl | 1 | absent | 4-benzyloxy-phenyl |
| 112 | pyrid-2-yl | 1 | absent | 4-benzyloxy-phenyl |
| 114 | 3-iodo-pyrid-2-yl | 1 | absent | 4-benzyl-phenyl |
| 118 | 3-iodo-pyrid-2-yl | 1 | absent | 4-benzyloxy-phenyl |
| 122 | pyrid-2-yl | 1 | absent | 4-(1-t-butoxycarbonyl-piperidin-4-yl)-phenyl |

TABLE 1-continued

Representative Compounds of Formula (I)

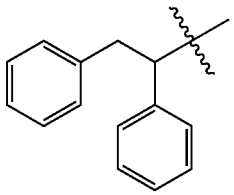

| Cmpd No. | Y | r | R² | Z |
|---|---|---|---|---|
| 124 | pyrid-2-yl | 1 | absent | 4-(1-t-butoxycarbonyl-piperidin-4-yl)oxy)-phenyl |
| 131 | pyrimidin-2-yl | 1 | absent | 4-benzyl-phenyl |
| 29 | pyrid-2-yl | 1 | absent | 1,1,4,4,tetramethyl-1,2,3,4-tetrahydro-naphth-6-yl-ethyl |
| 57 | pyrid-2-yl | 1 | absent | 6-methoxy-naphth-2-yl |
| 125 | pyrid-2-yl | 1 | absent | 1,2,3,4-tetrahydro-naphth-2-yl |
| 59 | pyrid-2-yl | 1 | absent | 2-(9-oxo-fluorenyl) |
| 96 | pyrid-2-yl | 1 | absent | fluoren-2-yl |
| 40 | pyrid-2-yl | 1 | absent | 4-(N-methyl-N-cyclohexylmethyl-amino)-phenylethyl |
| 51 | pyrimidin-2-yl | 1 | absent | 4-iodo-phenylethyl |
| 55 | pyrid-2-yl | 1 | absent | 4-(t-butyl)-phenylethyl |
| 64 | pyrimidin-2-yl | 1 | absent | 3-iodo-phenylethyl |
| 103 | pyrid-2-yl | 1 | absent | 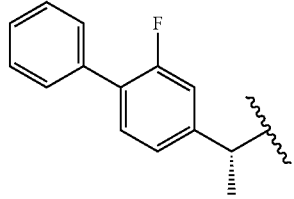 [SMILES: *[C@H](C)c1ccc(-c2ccccc2)c(F)c1] (also known as 1-(1,2-diphenyl)-ethyl) |
| 126 | pyrid-2-yl | 1 | absent | |
| 41 | pyrid-2-yl | 1 | absent | 4-(trifluoromethyl-thio)-phenyl-ethenyl |
| 65 | pyrid-2-yl | 1 | absent | 4-isopropyl-phenyl-ethenyl |
| 95 | pyrid-2-yl | 1 | absent | 3-trifluoromethyl-phenyl-ethenyl |
| 113 | pyrid-2-yl | 1 | absent | 3-ethoxy-phenyl-ethenyl |
| 54 | pyrid-2-yl | 1 | absent | 4-(n-pentyl)-cyclohexyl |
| 78 | pyrid-2-yl | 1 | absent | 4-(t-butyl)-cyclohexyl |
| 128 | pyrid-2-yl | 1 | absent | 4-pentyl-bicyclo[2.2.2]oct-l-yl |
| 139 | pyrimidin-2-yl | 1 | absent | 6-trifluoromethyl-benzo[b]thien-2-yl |

TABLE 2

Representative Compounds of Formula (I)

| Cmpd No. | Y | r | R² | Z |
|---|---|---|---|---|
| 10 | pyrimidin-2-yl | 1 | absent | 2-cyclohexyl-benzoxazol-6-yl |
| 14 | pyrimidin-2-yl | 1 | absent | 2-methyl-3-phenyl-benzimidazol-6-yl |
| 16 | pyrimidin-2-yl | 1 | absent | 1-isopropyl-2-trifluoromethyl-benzimidazol-4-yl |
| 17 | pyrimidin-2-yl | 1 | absent | 1-cyclohexyl-2-methyl-benzimidazol-4-yl |
| 31 | pyrid-2-yl | 1 | absent | 1-propyl-indol-5-yl |
| 49 | pyrid-2-yl | 1 | absent | 2-phenyl-benzimidazol-5-yl |
| 61 | pyrid-2-yl | 1 | absent | 4-phenyl-5-trifluoromethyl-thien-2-yl |

TABLE 2-continued

Representative Compounds of Formula (I)

| Cmpd No. | Y | r | R² | Z |
|---|---|---|---|---|
| 62 | pyrid-2-yl | 1 | absent | 5-benzyloxy-indol-2-yl |
| 80 | pyrid-2-yl | 1 | absent | 5-(3-trifluoromethyl-phenyl)-furan-2-yl) |
| 84 | pyrid-2-yl | 1 | absent | 5-(4-methylphenyl)-furan-2-yl |
| 92 | pyrid-2-yl | 1 | absent | 5-(4-methoxyphenyl)-furan-2-yl |
| 99 | pyrid-2-yl | 1 | absent | 5-phenyl-furan-2-yl |
| 107 | pyrid-2-yl | 1 | absent | 1-phenyl-pyrazol-4-yl |
| 108 | pyrid-2-yl | 1 | absent | 2-phenyl-5-trifluoromethyl-oxazol-4-yl |
| 115 | pyrid-2-yl | 1 | absent | quinolin-6-yl |
| 116 | pyrid-2-yl | 1 | absent | quinolin-2-yl |
| 117 | pyrid-2-yl | 1 | absent | 3-methyl-benzofuran-2-yl |
| 119 | pyrid-2-yl | 1 | absent | 5-butyl-pyrid-2-yl |
| 120 | pyrid-2-yl | 1 | absent | 4-benzyloxy-indol-2-yl |
| 121 | pyrid-2-yl | 1 | absent | indol-5-yl |
| 123 | pyrid-2-yl | 1 | absent | 5-(phenylethynyl)-furan-2-yl |
| 129 | pyrid-2-yl | 1 | absent | 5-(3,5-dichlorophenyloxy)-furan-2-yl |
| 130 | pyrid-2-yl | 1 | absent | Xanthen-3-yl-9-one |
| 63 | pyrid-2-yl | 1 | absent | (1-cyclohexyl-indolin-5-yl)-ethenyl- |
| 39 | pyrid-2-yl | 1 | absent | 1-(2,4-dichlorophenyl)-4-methyl-5-(4-chlorophenyl)-pyrazol-3-yl |
| 68 | pyrid-2-yl | 1 | absent | 1-(2,4-dichlorophenyl)-5-(4-chlorophenyl)-pyrazol-3-yl |
| 70 | pyrid-2-yl | 1 | absent | 1,5-diphenyl-pyrazol-3-yl |
| 72 | pyrid-2-yl | 1 | absent | 1-(4-aminosulfonyl-phenyl)-5-(4-chlorophenyl)-pyrazol-3-yl |
| 97 | pyrid-2-yl | 1 | absent | 1,2,3,4-tetrahydro-quinolin-6-yl |
| 132 | phenyl | 1 | absent | 1-phenyl-1,2,3,4-tetrahydro-quinolin-6-yl |
| 133 | 4-trifluoromethyl-phenyl | 1 | absent | 1,2,3,4-tetrahydro-quinolin-6-yl |
| 134 | 4-trifluoromethyl-phenyl | 1 | absent | 1-(4-trifluoromethyl-phenyl)-1,2,3,4-tetrahydro-quinolin-6-yl |
| 135 | 3-trifluoromethyl-phenyl | 1 | absent | 1-(3-trifluoromethyl-phenyl)-1,2,3,4-tetrahydro-quinolin-6-yl |

In an embodiment, the present invention is directed to one or more compounds of Formula (I) as herein defined, or enantiomers, diastereomers, solvates, or pharmaceutically acceptable salts thereof, wherein r is 1. In another embodiment, the present invention is directed to one or more compounds of Formula (I) as herein defined, or enantiomers, diastereomers, solvates, or pharmaceutically acceptable salts thereof, wherein r is 2.

In an embodiment, the present invention is directed to one or more compounds of Formula (I) as herein defined, or enantiomers, diastereomers, solvates, or pharmaceutically acceptable salts thereof, wherein $R^2$ is absent. In another embodiment, the present invention is directed to one or more compounds of Formula (I) as herein defined, or enantiomers, diastereomers, solvates, or pharmaceutically acceptable salts thereof, wherein $R^2$ is oxo.

In an embodiment, the present invention is directed to one or more compounds of Formula (I) as herein defined, or enantiomers, diastereomers, solvates, or pharmaceutically acceptable salts thereof, wherein Y is selected from the group consisting of phenyl, pyridyl, pyrimidyl, 1,3,5-triazinyl, thiazolyl, 1,3,4-thiadiazolyl, benzoxazolyl, benzisoxazolyl and benzothiazolyl; wherein the phenyl, pyridyl, pyrimidyl, 1,3,5-triazinyl, thiazolyl, 1,3,4-thiadiazolyl, benzoxazolyl, benzisoxazolyl, benzothiazolyl is optionally substituted with a substituent selected from the group consisting of cyano, fluoro, chloro, bromo, iodo, $C_{1-4}$alkyl, trifluoromethyl, $C_{1-4}$alkoxy, $C_{1-4}$alkylthio and nitro.

In another embodiment, the present invention is directed to one or more compounds of Formula (I) as herein defined, or enantiomers, diastereomers, solvates, or pharmaceutically acceptable salts thereof, wherein Y is selected from the group consisting of phenyl, pyridyl, pyrimidyl, 1,3,5-triazinyl, thiazolyl, 1,3,4-thiadiazolyl, benzoxazolyl, benzisoxazolyl and benzothiazolyl; wherein the phenyl, pyridyl, pyrimidyl, 1,3,5-triazinyl, thiazolyl, 1,3,4-thiadiazolyl, benzooxazolyl, benzisoxazolyl, benzothiazolyl is optionally substituted with a substituent selected from the group consisting of cyano, fluoro, chloro, bromo, iodo, $C_{1-2}$alkyl, trifluoromethyl, $C_{1-2}$alkoxy, $C_{1-2}$alkylthio and nitro.

In another embodiment, the present invention is directed to one or more compounds of Formula (I) as herein defined, or enantiomers, diastereomers, solvates, or pharmaceutically acceptable salts thereof, wherein Y is selected from the group consisting of phenyl, 3-trifluoromethyl-phenyl, 4-trifluoromethyl-phenyl, 2-methoxy-phenyl, 2-methylthio-phenyl, 2-nitro-phenyl pyrid-2-yl, 3-cyano-pyrid-2-yl, 5-cyano-pyrid-2-yl, 5-bromo-pyrid-2-yl, 3-chloro-pyrid-2-yl, 5-chloro-pyrid-2-yl, 3-iodo-pyrid-2-yl, 3-methyl-pyrid-2-yl, 4-methyl-pyrid-2-yl, 3-trifluoromethyl-pyrid-2-yl, pyrimidin-2-yl, 1,3,5-triazin-2-yl, benzooxazol-2-yl, benzisoxazol-3-yl, thiazol-2-yl, 5-trifluoromethyl-[1,3,4]-thiadiazol-2-yl and benzothiazol-2-yl.

In another embodiment, the present invention is directed to one or more compounds of Formula (I) as herein defined, or enantiomers, diastereomers, solvates, or pharmaceutically acceptable salts thereof, wherein Y is selected from the group consisting of pyrid-2-yl, 3-cyano-pyrid-2-yl, 5-cyano-pyrid-2-yl, 5-bromo-pyrid-2-yl, 3-chloro-pyrid-2-yl, 5-chloro-pyrid-2-yl, 3-iodo-pyrid-2-yl, 3-methyl-pyrid-2-yl, 4-methyl-pyrid-2-yl, 3-trifluoromethyl-pyrid-2-yl, pyrimidin-2-yl, 1,3,5-triazin-2-yl, benzoxazol-2-yl, benzisoxazol-3-yl, thiazol-2-yl, 5-trifluoromethyl-1,3,4-thiadiazol-2-yl and benzothiazol-2-yl. In another embodiment, the present invention is directed to one or more compounds of formula (I), or enantiomers, diastereomers, solvates, or pharmaceutically acceptable salts thereof, wherein Y is selected from the group consisting of phenyl, 3-trifluoromethyl-phenyl, 4-trifluoromethyl-phenyl, 2-methoxy-phenyl, 2-methylthio-phenyl and 2-nitro-phenyl, In another embodiment, the present invention is directed to one or more compounds of Formula (I) as herein defined, or enantiomers, diastereomers, solvates, or pharmaceutically acceptable salts thereof, wherein Y is selected from the group consisting of pyrid-2-yl-, 3-cyano-pyrid-2-yl, 5-chloro-pyrid-2-yl, pyrimidin-2-yl, thiazol-2-yl, 5-trifluoromethyl-1,3,4-thiadiazol-2-yl, 1,3,5-triazin-2-yl and benzisoxazol-2-yl. In another embodiment, the present invention is directed to one or more compounds of formula (I), or enantiomers, diastereomers, solvates, or pharmaceutically acceptable salts thereof, wherein Y is selected from the group consisting of pyrid-2-yl, 3-cyano-pyrid-2-yl, pyrimidin-2-yl, 1,3,5-triazin-2-yl, thiazol-2-yl, 5-trifluoromethyl-1,3,4-thiadiazol-2-yl and benzisoxazol-3-yl. In another embodiment, the present invention is directed to one or more compounds of formula (I), or enantiomers, diastereomers, solvates, or pharmaceutically acceptable salts thereof, wherein Y is selected from the group consisting of pyrid-2-yl, 3-cyano-pyrid-2-yl, pyrimidin-2-yl and thiazol-2-yl. In another embodiment, the present invention is directed to one or more compounds of Formula (I) as herein defined, or enantiomers, diastereomers, solvates, or pharmaceutically acceptable salts thereof, wherein Y is selected from the group consisting of pyrid-2-yl, pyrimidin-2-yl, thiazol-2-yl and benzisoxazol-2-yl.

In another embodiment, the present invention is directed to one or more compounds of Formula (I) as herein defined, or enantiomers, diastereomers, solvates, or pharmaceutically acceptable salts thereof, wherein Z is selected from the group consisting of (a) phenyl substituted with $NR^aR^b$; wherein $R^a$ is hydrogen or $C_{1-4}$alkyl; and $R^b$ is $C_{1-4}$alkyl, cycloalkyl, phenyl, furanylmethyl, or phenyl($C_{1-2}$alkyl); and wherein the phenyl of $R^b$, the phenyl of phenyl($C_{1-2}$alkyl) of $R^b$ or the furanyl of furanylmethyl of $R^b$ are optionally substituted with one iodo substituent; alternatively, $R^a$ and $R^b$ are taken together with the nitrogen atom to which they are both bound to form a 5 to 6 membered heterocyclyl, which heterocyclyl is optionally fused to a benzo group;

(b) biphenyl-3-yl or biphenyl-4-yl; wherein the terminal phenyl ring of is optionally substituted with a substituent selected from the group consisting of trifluoromethyl, $C_{1-4}$alkoxy, chloro, dichloro, fluoro, and iodo;

(c) phenyl substituted with a substituent selected from the group consisting of $C_{5-8}$cycloalkyl, —NHC(=O)cyclohexyl, phenyloxy, phenylcarbonyl, phenyl($C_{1-3}$)alkoxy, benzyl, pyrrolyl, pyrazolyl, imidazolyl, isoindol-2-yl-1,3-dione, 2,3-dihydro-isoindol-2-yl; 1-(t-butoxycarbonyl)piperidin-4-yloxy, and 1-(t-butoxycarbonyl)piperidin-4-yl;

(d) phenyl substituted with one to two substituents independently selected from the group consisting of $C_{1-6}$alkyl, $C_{1-4}$alkoxy, iodo, chloro and nitro;

(e) phenyl($C_{1-2}$)alkyl-; wherein the phenyl is optionally substituted with one to two substituent independently selected from the group consisting of iodo, fluoro, $C_{1-6}$alkyl, phenyl, and $NR^cR^d$; wherein $R^c$ is hydrogen or $C_{1-4}$alkyl; and wherein $R^d$ is $C_{1-4}$alkyl or $C_{3-6}$cycloalkyl($C_{1-4}$)alkyl; and wherein the $C_{1-2}$alkyl of phenyl($C_{1-2}$)alkyl is optionally substituted with phenyl;

(f) phenyl($C_{2-4}$)alkenyl-; wherein the phenyl is optionally substituted with a substituent selected from the group consisting of trifluoromethylthio, $C_{1-4}$alkyl, $C_{1-4}$alkoxy, phenyl, and trifluoromethyl;

(g) naphthyl; wherein the naphthyl is optionally substituted with one $C_{1-4}$alkoxy substituent;

(h) fluorenyl or xanthenyl; wherein the fluorenyl or xanthenyl is optionally substituted with oxo;

(i) $C_{5-6}$cyclalkyl; wherein the $C_{5-6}$cycloalkyl is optionally substituted with one $C_{1-5}$alkyl substituent;

(j) benzofused $C_{5-6}$cycloalkyl or benzofused $C_{5-6}$cycloalkyl($C_{1-4}$)alkyl; wherein said $C_{5-6}$cycloalkyl portion is optionally substituted with 1 to 4 methyl substituents;

(k) bicyclo[2.2.2]octyl-1-yl; wherein the bicyclo[2.2.2]octyl-1-yl is optionally substituted with $C_{1-6}$alkyl;

(l) a heteroaryl or benzo-fused heteroaryl selected from the group consisting of benzooxazolyl, quinolinyl, benzimidazolyl, pyridinyl, indolyl, thienyl, furanyl, pyrazolyl, oxazolyl, benzothienyl, and benzofuranyl; wherein the heteroaryl or benzo-fused heteroaryl is optionally substituted with one to two substituents independently selected from the group consisting of $C_{5-6}$cycloalkyl, $C_{1-4}$alkyl, phenyl, trifluoromethyl, phenyl($C_{1-2}$)alkoxy, dichlorophenoxy, and phenyl-ethynyl; and wherein the phenyl substituent on the heteroaryl is further optionally substituted with a substituent selected from methyl, methoxy, or trifluoromethyl;

(m) 1,5-diphenyl-1H-pyrazol-3-yl; wherein the pyrazol-3-yl is optionally substituted with a methyl substituent; and wherein each of the phenyl groups of the 1,5-diphenyl substituents is optionally substituted with a substituent selected from chloro, dichloro or aminosulfonyl;

(n) 1,2,3,4-tetrahydro-quinolin-6-yl; wherein the 1,2,3,4-tetrahydro-quinolin-6-yl is optionally substituted with phenyl or trifluoromethyl substituted phenyl; and (o) benzofused heterocyclyl($C_{2-4}$)alkenyl; wherein the benzofused heterocyclyl is attached to the $C_{2-4}$alkenyl via the benzo ring; and wherein benzofused heterocyclyl is optionally substituted with $C_{5-6}$cycloalkyl.

In another embodiment, the present invention is directed to one or more compounds of formula (I), or enantiomers, diastereomers, solvates, or pharmaceutically acceptable salts thereof, wherein Z is selected from the group consisting of (a) phenyl substituted with $NR^aR^b$; wherein $R^a$ is hydrogen or $C_{1-4}$alkyl; and $R^b$ is $C_{1-4}$alkyl, cycloalkyl, phenyl, furanylmethyl, or benzyl; and wherein the phenyl or benzyl of $R^b$ or the furanyl of furanylmethyl of $R^b$ are optionally substituted with one iodo substituent; alternatively, $R^a$ and $R^b$ are taken together with the nitrogen atom to which they are both bound to form 1-pyrrolidinyl or 1-azepanyl;

(b) biphenyl-3-yl or biphenyl-4-yl; wherein the terminal phenyl ring of is optionally substituted with a substituent selected from the group consisting of trifluoromethyl, $C_{1-4}$alkoxy, chloro, dichloro, fluoro, and iodo;

(c) phenyl substituted with a substituent selected from the group consisting of cyclohexyl, —NHC(=O)cyclohexyl, phenyloxy, phenylcarbonyl, benzyloxy, benzyl, pyrrolyl, pyrazolyl, imidazolyl, isoindol-2-yl-1,3-dione, 2,3-dihydro-isoindol-2-yl; 1-(t-butoxycarbonyl)piperidin-4-yloxy, and 1-(t-butoxycarbonyl)piperidin-4-yl;

(d) phenyl substituted with one to two substituents independently selected from the group consisting of $C_{1-6}$alkyl, $C_{1-4}$alkoxy, iodo, chloro and nitro;

(e) phenyl($C_{1-2}$)alkyl-; wherein the phenyl is optionally substituted with one to two substituent independently selected from the group consisting of iodo, fluoro, $C_{1-6}$alkyl, phenyl, and $NR^cR^d$; wherein $R^c$ is hydrogen or $C_{1-4}$alkyl; and wherein $R^d$ is $C_{1-4}$alkyl or $C_{3-6}$cycloalkyl($C_{1-4}$)alkyl; and wherein the $C_{1-2}$alkyl of phenyl($C_{1-2}$)alkyl is optionally substituted with phenyl;

(f) phenyl($C_{2-4}$)alkenyl-; wherein the phenyl is optionally substituted with a substituent selected from the group consisting of trifluoromethylthio, $C_{1-4}$alkyl, $C_{1-4}$alkoxy, and trifluoromethyl;

(g) naphthyl; wherein the naphthyl is optionally substituted with one $C_{1-4}$alkoxy substituent;

(h) fluorenyl or xanthenyl; wherein the fluorenyl or xanthenyl is optionally substituted with oxo;

(i) cyclohexyl; wherein the cyclohexyl is optionally substituted with one $C_{1-6}$alkyl substituent;

(j) benzofused $C_{5-6}$cycloalkyl or benzofused $C_{5-6}$cycloalkyl($C_{1-4}$)alkyl; wherein said $C_{5-6}$cycloalkyl portion is optionally substituted with 1 to 4 methyl substituents;

(k) bicyclo[2.2.2]octyl-1-yl; wherein the bicyclo[2.2.2]octyl-1-yl is optionally substituted with $C_{1-6}$alkyl;

(l) a heteroaryl or benzo-fused heteroaryl selected from the group consisting of benzooxazolyl, quinolinyl, benzimidazolyl, pyridinyl, indolyl, thienyl, furanyl, pyrazolyl, oxazolyl, benzothienyl, and benzofuranyl; wherein the heteroaryl or benzo-fused heteroaryl is optionally substituted with one to two substituents independently selected from the group consisting of cyclohexyl, $C_{1-4}$alkyl, phenyl, trifluoromethyl, benzyloxy, dichlorophenoxy, and phenyl-ethynyl; and wherein the phenyl substituent on the heteroaryl is further optionally substituted with a substituent selected from methyl, methoxy, or trifluoromethyl;

(m) 1,5-diphenyl-1H-pyrazol-3-yl; wherein the pyrazol-3-yl is optionally substituted with a methyl substituent; and wherein each of the phenyl groups of the 1,5-diphenyl substituents is optionally substituted with a substituent selected from chloro, dichloro or aminosulfonyl;

(n) 1,2,3,4-tetrahydro-quinolin-6-yl; wherein the 1,2,3,4-tetrahydro-quinolin-6-yl is optionally substituted with phenyl or trifluoromethyl substituted phenyl; and (o) benzofused heterocyclyl($C_{2-4}$)alkenyl; wherein the benzofused heterocyclyl is attached to the $C_{2-4}$alkenyl via the benzo ring; and wherein benzofused heterocyclyl is optionally substituted with cyclohexyl.

In another embodiment, the present invention is directed to one or more compounds of Formula (I) as herein defined, or enantiomers, diastereomers, solvates, or pharmaceutically acceptable salts thereof, wherein Z is selected from the group consisting of 4-(N-methyl-N-cyclohexyl-amino)-phenyl, 4-(pyrrolidin-1-yl)-phenyl, 4-(1-azepanyl)-phenyl, 4-(3-trifluoromethyl-phenyl)-phenyl, 4-(4-methoxyphenyl)-phenyl, 4-cyclohexyl-phenyl, 4-(N-(2-iodobenzyl)-amino)-phenyl, 4-(2-chlorophenyl)-phenyl, 4-(4-fluorophenyl)-phenyl, 4-(3,4-dichlorophenyl)-phenyl, biphen-4-yl, 4-(N-methyl-N-phenyl-amino)-phenyl, 4-(4-iodophenyl)-phenyl, 4-phenyloxy-phenyl, 4-(N-(5-iodo-furan-2-ylmethyl)amino)-phenyl, 4-benzyl-phenyl, 4-(pyrrol-1-yl)-phenyl, 4-(3-fluorophenyl)-phenyl, 4-(N-cyclohexylcarbonyl-amino)-phenyl, 4-dimethylamino-phenyl, 4-butyl-phenyl, 4-diethylamino-phenyl, 3-iodo-4-methoxy-phenyl, 3-iodo-4-chloro-phenyl, 4-(1,1-dimethyl-propyl)-phenyl, 4-(pyrazol-1-yl)-phenyl, 3-(phenyloxy)-phenyl, 3-iodo-4-methyl-phenyl, 3-methyl-4-iodo-phenyl, 3-(4-fluorophenyl)-phenyl, 4-iodophenyl, 2-(benzyloxy)-phenyl, biphen-3-yl, 4-(imidazol-1-yl)-phenyl, 4-(phenylcarbonyl)-phenyl, 2-(isoindolyl-1,3-dione)-phenyl, 3-(2,3-dihydro-1H-isoindol-2-yl)-phenyl, 3-(phenylcarbonyl)-phenyl, 4-nitrophenyl, 4-benzyloxy-phenyl, 4-(1-t-butoxycarbonyl-piperidin-4-yl-phenyl, 4-(1-t-butoxycarbonyl-piperidin-4-yl)oxy)-phenyl, 1,1,4,4,tetramethyl-1,2,3,4-tetrahydro-naphth-6-yl, 6-methoxy-naphth-2-yl, 1,2,3,4-tetrahydro-naphth-2-yl, 2-(9-oxo-fluorenyl), fluoren-2-yl, 4-(N-methyl-N-cyclohexylmethyl-amino)-phenylethyl, 4-iodo-phenylethyl, 4-(t-butyl)-phenylethyl, 3-iodo-phenylethyl,

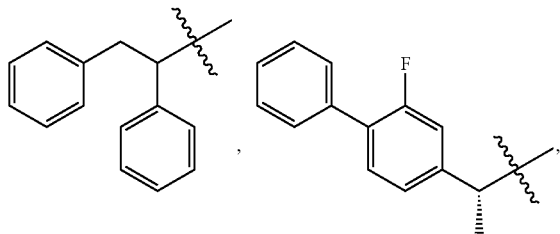 [SMILES: *C(Cc1ccccc1)c1ccccc1 ; *[C@H](C)c1ccc(-c2ccccc2)c(F)c1]

4-(trifluoromethyl-thio)-phenyl-ethenyl, 4-isopropyl-phenyl-ethenyl, 3-trifluoromethyl-phenyl-ethenyl, 3-ethoxy-phenyl-ethenyl, 4-(n-pentyl)-cyclohexyl, 4-(t-butyl)-cyclohexyl, 4-pentyl-bicyclo[2.2.2]oct-1-yl, 2-cyclohexyl-benzoxazol-6-yl, 2-methyl-3-phenyl-benzimidazol-6-yl, 1-isopropyl-2-trifluoromethyl-benzimidazol-4-yl, 1-cyclohexyl-2-methyl-benzimidazol-4-yl, 1-propyl-indol-5-yl, 1-(2,4-dichlorophenyl)-4-methyl-5-(4-chlorophenyl)-pyra- zol-3-yl, 2-phenyl-benzimidazol-5-yl, 4-phenyl-5-trifluoromethyl-thien-2-yl, 5-benzyloxy-indol-2-yl, 1-(2,4-dichlorophenyl)-5-(4-chlorophenyl)-pyrazol-3-yl, 1,5-diphenyl-pyrazol-3-yl, 1-(4-aminosulfonyl-phenyl)-5-(4-chlorophenyl)-pyrazol-3-yl, 5-(3-trifluoromethyl-phenyl)-furan-2-yl, 5-(4-methylphenyl)-furan-2-yl, 5-(4-methoxyphenyl)-furan-2-yl, 1,2,3,4-tetrahydro-quinolin-6-yl, 5-phenyl-furan-2-yl, 1-phenyl-pyrazol-4-yl, 2-phenyl-5-trifluoromethyl-oxazol-4-yl, quinolin-6-yl, quinolin-2-yl, 3-methyl-benzofuran-2-yl, 5-butyl-pyrid-2-yl, 4-benzyloxy-indol-2-yl, indol-5-yl, 5-(phenylethynyl)-furan-2-yl, 5-(3,5-dichlorophenyloxy)-furan-2-yl, xanthen-3-yl-9-one, 1-phenyl-1,2,3,4-tetrahydro-quinolin-6-yl, 1-(4-trifluoromethyl-phenyl)-1,2,3,4-tetrahydro-quinolin-6-yl, 1-(3-trifluoromethyl-phenyl)-1,2,3,4-tetrahydro-quinolin-6-yl, (1-cyclohexyl-indolin-5-yl)-ethenyl- and 6-trifluoromethyl-benzo[b]thien-2-yl.

In another embodiment, the present invention is directed to one or more compounds of formula (I), or enantiomers, diastereomers, solvates, or pharmaceutically acceptable salts thereof, wherein Z is selected from the group consisting of 4-(N-methyl-N-cyclohexyl-amino)-phenyl, 4-(pyrrolidin-1-yl)-phenyl, 4-(1-azepanyl)-phenyl, 4-(3-trifluoromethyl-phenyl)-phenyl, 4-(4-methoxyphenyl)-phenyl, 4-cyclohexyl-phenyl, 4-(N-(2-iodobenzyl)-amino)-phenyl, 4-(2-chlorophenyl)-phenyl, 4-(4-fluorophenyl)-phenyl, 4-(3,4-dichlorophenyl)-phenyl, biphen-4-yl, 4-(N-methyl-N-phenyl-amino)-phenyl, 4-(4-iodophenyl)-phenyl, 4-phenyloxy-phenyl, 4-(N-(5-iodo-furan-2-ylmethyl) amino)-phenyl, 4-benzyl-phenyl, 4-(pyrrol-1-yl)-phenyl, 4-(3-fluorophenyl)-phenyl, 4-(N-cyclohexylcarbonyl-amino)-phenyl, 4-dimethylamino-phenyl, 4-butyl-phenyl, 4-diethylamino-phenyl, 3-iodo-4-methoxy-phenyl, 3-iodo-4-chloro-phenyl, 4-(1,1-dimethyl-propyl)-phenyl, 4-(pyrazol-1-yl)-phenyl, 3-(phenyloxy)-phenyl, 3-iodo-4-methyl-phenyl, 3-methyl-4-iodo-phenyl, 3-(4-fluorophenyl)-phenyl, 4-iodophenyl, 2-(benzyloxy)-phenyl, 4-benzyloxy-phenyl, 4-(1-t-butoxycarbonyl-piperidin-4-yl)-phenyl, 4-(1-t-butoxycarbonyl-piperidin-4-yl)oxy)-phenyl, 1,1,4,4,tetramethyl-1,2,3,4-tetrahydro-naphth-6-yl-ethyl, 6-methoxy-naphth-2-yl, 2-(9-oxo-fluorenyl), 4-(N-methyl-N-cyclohexylmethyl-amino)-phenylethyl, 4-iodo-phenylethyl, 4-(t-butyl)-phenylethyl, 4-(trifluoromethyl-thio)-phenyl-ethenyl, 4-(n-pentyl)-cyclohexyl, 2-cyclohexyl-benzoxazol-6-yl, 2-methyl-3-phenyl-benzimidazol-6-yl, 1-isopropyl-2-trifluoromethyl-benzimidazol-4-yl, 1-cyclohexyl-2-methyl-benzimidazol-4-yl, 1-propyl-indol-5-yl, 2-phenyl-benzimidazol-5-yl, 4-phenyl-5-trifluoromethyl-thien-2-yl, xanthen-3-yl-9-one, 1-(2,4-dichlorophenyl)-4-methyl-5-(4-chlorophenyl)-pyrazol-3-yl and 6-trifluoromethyl-benzo[b]thien-2-yl.

In another embodiment, the present invention is directed to one or more compounds of formula (I), or enantiomers, diastereomers, solvates, or pharmaceutically acceptable salts thereof, wherein Z is selected from the group consisting of 4-(N-methyl-N-cyclohexyl-amino)-phenyl, 4-(pyrrolidin-1-yl)-phenyl, 4-(1-azepanyl)-phenyl, 4-(3-trifluoromethyl-phenyl)-phenyl, 4-(4-methoxyphenyl)-phenyl, 4-cyclohexyl-phenyl, 4-(N-(2-iodobenzyl)-amino)-phenyl, 4-(2-chlorophenyl)-phenyl, 4-(4-fluorophenyl)-phenyl, 4-(3,4-dichlorophenyl)-phenyl, biphen-4-yl, 4-(N-methyl-N-phenyl-amino)-phenyl, 4-(4-iodophenyl)-phenyl, 4-phenyloxy-phenyl, 4-(N-(5-iodo-furan-2-ylmethyl) amino)-phenyl, 4-benzyl-phenyl, 4-(pyrrol-1-yl)-phenyl, 4-(3-fluorophenyl)-phenyl, 4-(N-cyclohexylcarbonyl-amino)-phenyl, 4-dimethylamino-phenyl, 4-diethylamino-phenyl, 4-benzyloxy-phenyl, 2-cyclohexyl-benzoxazol-6-yl, 2-methyl-3-phenyl-benzimidazol-6-yl, 1-isopropyl-2-trifluoromethyl-benzimidazol-4-yl, 1-cyclohexyl-2-methyl-benzimidazol-4-yl, 1-propyl-indol-5-yl and 6-trifluoromethyl-benzo[b]thien-2-yl.

In another embodiment, the present invention is directed to one or more compounds of Formula (I) as herein defined, or enantiomers, diastereomers, solvates, or pharmaceutically acceptable salts thereof, wherein Z is selected from the group consisting of 4-(N-methyl-N-cyclohexyl-amino)-phenyl, 4-(pyrrolidin-1-yl)-phenyl, 4-(1-azepanyl)-phenyl, 4-(3-trifluoromethyl-phenyl)-phenyl, 4-(4-methoxyphenyl)-phenyl, 4-(2-chlorophenyl)-phenyl, 4-(4-fluorophenyl)-phenyl, 4-(3,4-dichlorophenyl)-phenyl, biphen-4-yl, 4-(N-methyl-N-phenyl-amino)-phenyl, 4-phenyloxy-phenyl, 4-cyclohexyl-phenyl, 4-benzyl-phenyl, 4-(pyrrol-1-yl)-phenyl, 4-(3-fluorophenyl)-phenyl, 4-(N-cyclohexylcarbonyl-amino)-phenyl, 4-dimethylamino-phenyl, 4-butyl-phenyl, 4-diethylamino-phenyl, 3-(4-fluorophenyl)-phenyl, 4-benzyloxy-phenyl, 4-(1-t-butoxycarbonyl-piperidin-4-yl)-phenyl, 1,1,4,4,tetramethyl-1,2,3,4-tetrahydro-naphth-6-yl-ethyl, 4-(N-methyl-N-cyclohexylmethyl-amino)-phenylethyl, 4-(trifluoromethyl-thio)-phenylethenyl, 2-methyl-3-phenyl-benzimidazol-6-yl, 1-isopropyl-2-trifluoromethyl-benzimidazol-4-yl, 1-cyclohexyl-2-methyl-benzimidazol-4-yl, 1-propyl-indol-5-yl and 1-(2,4-dichlorophenyl)-4-methyl-5-(4-chlorophenyl)-pyrazol-3-yl.

In another embodiment, the present invention is directed to one or more compounds of Formula (I) as herein defined, or enantiomers, diastereomers, solvates, or pharmaceutically acceptable salts thereof, wherein Z is selected from the group consisting of 4-cyclohexyl-phenyl, biphen-4-yl, 4-(N-cyclohexylcarbonyl-amino)-phenyl, 4-benzylphenyl, 4-diethylaminophenyl, 3-iodo-4-methoxy-phenyl, 3-(4-fluorophenyl)-phenyl, 4-(3-fluorophenyl)-phenyl, 4-(N-methyl-N-cyclohexylmethyl-amino)phenyl, 9-oxo-fluoren-2-yl and 2-cyclohexyl-benzooxazol-6-yl.

In further embodiments, the present invention is directed to one or more compounds of Formula (I) as herein defined, or enantiomers, diastereomers, solvates, or pharmaceutically acceptable salts thereof, wherein r is an integer from 1 to 2; $R^2$ is absent; Y is selected from the groups (Y-a) through (Y-b), as hereinafter defined; and/or Z is selected from the groups (Z-a) through (Z-f), as hereinafter defined; with the proviso that compound of Formula (I) as herein defined is other than Compound #200: a compound wherein Y is 3-methylpyridin-2-yl, Z is 4-biphenyl, r is 1, and $R^2$ is absent;

Compound #201: a compound wherein Y is pyridin-2-yl, Z is 2-(phenylcarbonyl)phenyl, r is 1, and $R^2$ is absent;

Compound #202: a compound wherein Y is 5-trifluoromethylpyridin-2-yl, Z is 4-cyclohexyl-phenyl, r is 1, and $R^2$ is absent;

Compound #203: a compound wherein Y is pyridin-2-yl, Z is 3-(cyclohexylcarbonylamino)phenyl, r is 1, and $R^2$ is absent;

Compound #204: a compound wherein Y is 5-cyanopyridin-2-yl, Z is 4-biphenyl, r is 1, and $R^2$ is absent;

Compound #205: a compound wherein Y is 5-trifluoromethylpyridin-2-yl, Z is 4-biphenyl, r is 1, and $R^2$ is absent;

Compound #206: a compound wherein Y is pyrimidin-2-yl, Z is 2-(4-trifluoromethylthiophenyl)-vinyl, r is 2, and $R^2$ is absent;

Compound #207: a compound wherein Y is pyridin-2-yl, Z is 2-phenyl-vinyl, r is 1, and $R^2$ is absent;

Compound #208: a compound wherein Y is pyridin-2-yl, Z is 2-phenylethyl, r is 1, and $R^2$ is absent;

Compound #209: a compound wherein Y is pyridin-2-yl, Z is 2-t-butyl-benzoxazol-6-yl, r is 1, and $R^2$ is absent;

Compound #210: a compound wherein Y is pyridin-2-yl, Z is 2-(4-methoxyphenyl)-benzoxazol-7-yl, r is 1, and $R^2$ is absent;

Compound #211: a compound wherein Y is pyridin-2-yl, Z is 2-cyclohexyl-benzoxazol-6-yl, r is 1, and $R^2$ is absent;

Compound #212: a compound wherein Y is pyridin-2-yl, Z is 1,2-diisobutyl-1H-indol-5-yl, r is 1, and $R^2$ is absent;

Compound #213: a compound wherein Y is pyridin-2-yl, Z is 1-methyl-2-propyl-1H-indol-5-yl, r is 1, and $R^2$ is absent;

Compound #214: a compound wherein Y is pyridin-2-yl, Z is 1-isobutyl-2-phenyl-1H-indol-5-yl, r is 1, and $R^2$ is absent;

Compound #215: a compound wherein Y is pyridin-2-yl, Z is 1-isobutyl-2-(4-methylphenyl)-1H-indol-5-yl, r is 1, and $R^2$ is absent;

Compound #216: a compound wherein Y is pyridin-2-yl, Z is 2-(3-methoxyphenyl)-benzoxazol-5-yl, r is 1, and $R^2$ is absent;

Compound #217: a compound wherein Y is pyridin-2-yl, r is 1, and $R^2$ is absent and Z is 2-benzylphenyl;

Compound #218: a compound wherein Y is pyridin-2-yl, r is 1, and $R^2$ is absent and Z is (1R)-1,2,3,4-tetrahydronaphthalen-1-yl;

Compound #219: a compound wherein Y is pyridin-2-yl, r is 1, and $R^2$ is absent and Z is (1S)-1-[4-(2-methylpropyl)phenyl]ethyl;

Compound #220: a compound wherein Y is pyridin-2-yl, r is 1, and $R^2$ is absent and Z is (1S)-1-(2-fluoro-[1,1'-biphenyl]-4-yl)ethyl;

Compound #221: a compound wherein Y is pyridin-2-yl, r is 1, and $R^2$ is absent and Z is 2,3-dihydro-1H-inden-2-yl;

Compound #222: a compound wherein Y is pyridin-2-yl, r is 1, and $R^2$ is absent and Z is 2,2-diphenylethyl; or Compound #223: a compound wherein Y is 3-trifluoromethylphenyl, r is 1, and $R^2$ is absent and Z is 1,2,3,4-tetrahydroquinolin-6-yl.

As used herein, (Y-a) shall mean that Y is a heteroaryl selected from the group consisting of thiazolyl, pyridinyl, pyrimidinyl, 1,3,5-triazinyl, benzooxazolyl, benzo[d]isoxazolyl, and 1,3,4-thiadiazolyl; and wherein Y is optionally substituted with one substituent selected from the group consisting of cyano, trifluoromethyl, fluoro, chloro, bromo, iodo, and $C_{1-4}$alkyl.

As used herein, (Y-b) shall mean that Y is a heteroaryl selected from the group consisting of thiazolyl, pyridinyl, pyrimidinyl, 1,3,5-triazinyl, benzo[d] isoxazolyl, and 1,3,4-thiadiazolyl; and wherein Y is optionally substituted with one substituent selected from the group consisting of cyano, trifluoromethyl, chloro, bromo, iodo, and $C_{1-4}$alkyl.

As used herein, (Z-a) shall mean that Z is selected from the group consisting of (a) phenyl substituted with $NR^aR^b$; wherein $R^a$ is hydrogen or $C_{1-4}$alkyl; and $R^b$ is $C_{1-4}$alkyl, cycloalkyl, or phenyl; and wherein the phenyl of $R^b$ is optionally substituted with one iodo substituent; alternatively, $R^a$ and $R^b$ are taken together with the nitrogen atom to which they are both bound to form a 5 to 8 membered heterocyclyl;

(b) biphenyl-3-yl or biphenyl-4-yl; wherein the interior phenyl ring, attached to the carbonyl of Formula (I), of said biphenyl-3-yl and biphenyl-4-yl is optionally substituted with one fluoro substituent; and wherein the terminal phenyl ring of said biphenyl-3-yl and biphenyl-4-yl is optionally substituted with one substituent selected from the group consisting of trifluoromethyl, $C_{1-4}$alkoxy, chloro, dichloro, fluoro, and iodo;

(c) phenyl substituted with one substituent selected from the group consisting of cyclohexyl, phenyloxy, phenyl($C_{1-3}$)

alkoxy, benzyl, pyrrolyl, pyrazolyl, 1-(t-butoxycarbonyl)piperidin-4-yloxy, and 1-(t-butoxycarbonyl)piperidin-4-yl;

(d) phenyl; wherein the phenyl is optionally substituted with one to two substituents independently selected from the group consisting of $C_{1-4}$alkoxy, iodo, $C_{1-6}$alkyl, and chloro;

(e) phenyl($C_{1-2}$)alkyl; wherein the phenyl is optionally substituted with one substituent selected from the group consisting of iodo, $C_{1-6}$alkyl, and $NR^cR^d$; and wherein $R^c$ is hydrogen or $C_{1-4}$alkyl and $R^d$ is $C_{1-4}$alkyl or cyclohexyl($C_{1-4}$alkyl;

(f) phenyl($C_{2-4}$)alkenyl; wherein the phenyl is optionally substituted with one trifluoromethylthio, $C_{1-4}$alkyl, or phenyl substituent;

(g) naphthyl; wherein the naphthyl is optionally substituted with one $C_{1-4}$alkoxy substituent;

(h) cyclohexyl; wherein the cyclohexyl is optionally substituted with one $C_{1-6}$alkyl substituent;

(i) benzofused cyclohexyl($C_{1-4}$alkyl; wherein the cyclohexyl portion is optionally substituted with 1 to 4 methyl substituents;

(j) benzofused heterocyclyl($C_{2-4}$)alkenyl; wherein the benzofused heterocyclyl is attached to $C_{2-4}$alkenyl via the benzo ring; and wherein benzofused heterocyclyl is optionally substituted with $C_{3-6}$cycloalkyl;

(k) heteroaryl or benzo-fused heteroaryl selected from the group consisting of benzoxazolyl, benzimidazolyl, pyridinyl, indolyl, and thienyl; wherein the heteroaryl or benzo-fused heteroaryl is optionally independently substituted with one to two substituents selected from the group consisting of cyclohexyl, $C_{1-4}$alkyl, phenyl, trifluoromethyl, phenyl($C_{1-4}$)alkoxy, and phenyl-ethynyl; or (l) 1,5-diphenyl-1H-pyrazol-3-yl; wherein the pyrazol-3-yl portion is optionally substituted with a methyl substituent; and wherein the 1,5-phenyl substituents are each optionally independently substituted with one to two chloro substituents or aminosulfonyl.

As used herein, (Z-b) shall mean that Z is selected from the group consisting of (a) phenyl substituted with $NR^aR^b$; wherein $R^a$ is hydrogen or $C_{1-4}$alkyl; and $R^b$ is $C_{1-4}$alkyl, cycloalkyl, or phenyl; and wherein the phenyl of $R^b$ is optionally substituted with one iodo substituent; alternatively, $R^a$ and $R^b$ are taken together with the nitrogen atom to which they are both bound to form a 5 to 8 membered heterocyclyl;

(b) biphenyl-3-yl or biphenyl-4-yl; wherein the interior phenyl ring, attached to the carbonyl of Formula (I), of the biphenyl-3-yl and biphenyl-4-yl is optionally substituted with one fluoro substituent; and wherein the terminal phenyl ring of said biphenyl-3-yl and biphenyl-4-yl is optionally substituted with one substituent selected from the group consisting of trifluoromethyl, $C_{1-4}$alkoxy, chloro, dichloro, fluoro, and iodo;

(c) phenyl substituted with one substituent selected from the group consisting of cyclohexyl, phenyloxy, phenyl($C_{1-3}$)alkoxy, 3- or 4-phenylmethyl, and pyrrolyl;

(d) phenyl substituted with one to two substituents independently selected from the group consisting of alkoxy, iodo, and $C_{1-6}$alkyl;

(e) phenyl($C_{1-2}$)alkyl; wherein the phenyl is optionally substituted with $NR^cR^d$; wherein $R^c$ is hydrogen or $C_{1-4}$alkyl and $R^d$ is $C_{1-4}$alkyl or cycloalkyl($C_{1-4}$)alkyl;

(f) 2-phenyl-vinyl wherein phenyl is optionally substituted with trifluoromethylthio;

(g) benzofused cyclohexyl($C_{1-4}$)alkyl, wherein said cyclohexyl is optionally substituted with 1 to 4 methyl substituents; or (h) heteroaryl or benzo-fused heteroaryl selected from the group consisting of benzoxazolyl and indolyl; wherein heteroaryl or benzo-fused heteroaryl is optionally substituted with one substituent selected from the group consisting of cyclohexyl, $C_{1-4}$alkyl, phenyl, and trifluoromethyl; or (i) 1,5-diphenyl-1H-pyrazol-3-yl wherein the pyrazol-3-yl is optionally substituted with one methyl substituent; and wherein the 1,5-phenyl substituents are each optionally independently substituted with one to two chloro substituents or aminosulfonyl.

As used herein, (Z-c) shall mean that Z is selected from the group consisting of (a) phenyl substituted with $NR^aR^b$; wherein $R^a$ is hydrogen or $C_{1-4}$alkyl; and $R^b$ is $C_{1-4}$alkyl, cycloalkyl, or phenyl; and wherein the phenyl of $R^b$ is optionally substituted with one iodo substituent; alternatively $R^a$ and $R^b$ are taken together with the nitrogen atom to which they are both bound to form a 5 to 8 membered heterocyclyl;

(b) biphenyl-3-yl or biphenyl-4-yl; wherein the interior phenyl ring, attached to the carbonyl of Formula (I), of said biphenyl-3-yl and biphenyl-4-yl is optionally substituted with one fluoro substituent; and wherein the terminal phenyl ring of said biphenyl-3-yl and biphenyl-4-yl is optionally substituted with one substituent selected from the group consisting of trifluoromethyl, $C_{1-4}$alkoxy, chloro, dichloro, fluoro, and iodo;

(c) phenyl substituted with one substituent selected from the group consisting of cyclohexyl, phenyloxy, phenyl($C_{1-3}$)alkoxy, 3- or 4-phenylmethyl, and pyrrolyl;

(d) phenyl substituted with one to two substituents independently selected from the group consisting of alkoxy, iodo, and $C_{1-6}$alkyl;

(e) phenyl($C_{1-2}$)alkyl; wherein the phenyl is optionally substituted with $NR^cR^d$; wherein $R^c$ is hydrogen or $C_{1-4}$alkyl and $R^d$ is $C_{1-4}$alkyl or cycloalkyl($C_{1-4}$)alkyl; or (f) 2-phenyl-vinyl wherein phenyl is optionally substituted with trifluoromethylthio;

(g) benzofused cyclohexyl($C_{1-4}$alkyl, wherein the cyclohexyl is optionally substituted with 1 to 4 methyl substituents; or (h) heteroaryl or benzo-fused heteroaryl selected from the group consisting of benzoxazolyl and indolyl; wherein the heteroaryl or benzo-fused heteroaryl is optionally substituted with one substituent selected from the group consisting of cyclohexyl, $C_{1-4}$alkyl, phenyl, and trifluoromethyl.

As used herein, (Z-d) shall mean that Z is selected from the group consisting of (a) phenyl substituted with $NR^aR^b$; wherein $R^a$ is hydrogen or $C_{1-4}$alkyl; and $R^b$ is $C_{1-4}$alkyl, cycloalkyl, or phenyl; and wherein the phenyl of $R^b$ is optionally substituted with one iodo substituent; alternatively $R^a$ and $R^b$ are taken together with the nitrogen atom to which they are both bound to form a 5 to 8 membered heterocyclyl;

(b) biphenyl-3-yl or biphenyl-4-yl; wherein the interior phenyl ring, attached to the carbonyl of Formula (I), of said biphenyl-3-yl and biphenyl-4-yl is optionally substituted with one fluoro substituent; and wherein the terminal phenyl ring of said biphenyl-3-yl and biphenyl-4-yl is optionally substituted with one substituent selected from the group consisting of trifluoromethyl, $C_{1-4}$alkoxy, chloro, dichloro, fluoro, and iodo;

(c) phenyl substituted with one substituent selected from the group consisting of cyclohexyl, phenyloxy, phenyl($C_{1-3}$)alkoxy, 3-phenylmethyl, 4-phenylmethyl, pyrrolyl, pyrazolyl, 1-(t-butoxycarbonyl)piperidin-4-yloxy, and 1-(t-butoxycarbonyl)piperidin-4-yl;

(d) phenyl substituted with one to two substituents independently selected from the group consisting of alkoxy, iodo, $C_{1-6}$alkyl, and chloro;

(e) phenyl($C_{1-2}$)alkyl; wherein said phenyl is optionally substituted with one substituent selected from the group consisting of iodo, $C_{1-6}$alkyl, and $NR^cR^d$; wherein $R^c$ is hydrogen or $C_{1-4}$alkyl and $R^d$ is $C_{1-4}$alkyl or cyclohexyl($C_{1-4}$alkyl;

(f) phenyl($C_{2-4}$)alkenyl wherein phenyl is optionally substituted with one trifluoromethylthio, $C_{1-4}$alkyl, or phenyl substituent;

(g) naphthyl optionally substituted with one $C_{1-4}$alkoxy substituent;

(h) cyclohexyl optionally substituted with one $C_{1-6}$alkyl substituent;

(i) benzofused cyclohexyl($C_{1-4}$alkyl, wherein said cyclohexyl is optionally substituted with 1 to 4 methyl substituents;

(j) benzofused heterocyclyl($C_{2-4}$)alkenyl wherein the benzofused heterocyclyl is attached to $C_{2-4}$alkenyl via the benzo ring; and wherein the benzofused heterocyclyl is optionally substituted with $C_{3-6}$cycloalkyl;

(k) heteroaryl or benzo-fused heteroaryl selected from the group consisting of benzoxazolyl, benzimidazolyl, pyridinyl, indolyl, and thienyl; wherein heteroaryl or benzo-fused heteroaryl is optionally independently substituted with one to two substituents selected from the group consisting of cyclohexyl, $C_{1-4}$alkyl, phenyl, trifluoromethyl, phenyl($C_{1-4}$)alkoxy, and phenyl-ethynyl; or (l) 1,5-diphenyl-1H-pyrazol-3-yl wherein the pyrazol-3-yl is optionally substituted with one methyl substituent; and wherein the 1,5-phenyl substituents are each optionally independently substituted with one to two chloro substituents or aminosulfonyl.

As used herein, (Z-e) shall mean that Z is selected from the group consisting of (a) phenyl substituted with $NR^aR^b$; wherein $R^a$ is hydrogen or $C_{1-4}$alkyl; and $R^b$ is $C_{1-4}$alkyl, cycloalkyl, or phenyl; and wherein the phenyl of $R^b$ is optionally substituted with one iodo substituent; or $R^a$ and $R^b$ are taken together with the nitrogen atom to which they are both bound to form a 5 to 8 membered heterocyclyl;

(b) biphenyl-3-yl or biphenyl-4-yl; wherein the interior phenyl ring, attached to the carbonyl of Formula (I), of said biphenyl-3-yl and biphenyl-4-yl is optionally substituted with one fluoro substituent; and wherein the terminal phenyl ring of said biphenyl-3-yl and biphenyl-4-yl is optionally substituted with one substituent selected from the group consisting of trifluoromethyl, $C_{1-4}$alkoxy, chloro, dichloro, fluoro, and iodo;

(c) phenyl substituted with one substituent selected from the group consisting of cyclohexyl, phenyloxy, phenyl($C_{1-3}$)alkoxy, 3-phenylmethyl, 4-phenylmethyl, and pyrrolyl;

(d) phenyl substituted with one to two substituents independently selected from the group consisting of alkoxy, iodo, and $C_{1-6}$alkyl;

(e) phenyl($C_{1-2}$)alkyl; wherein the phenyl is optionally substituted with $NR^cR^d$; wherein $R^c$ is hydrogen or $C_{1-4}$alkyl and $R^d$ is $C_{1-4}$alkyl or $C_{3-6}$cycloalkyl($C_{1-4}$alkyl;

(f) 2-phenyl-vinyl wherein phenyl is optionally substituted with trifluoromethylthio;

(g) benzofused cyclohexyl($C_{1-4}$alkyl, wherein said cyclohexyl is optionally substituted with 1 to 4 methyl substituents;

(h) heteroaryl or benzo-fused heteroaryl selected from the group consisting of benzoxazolyl and indolyl; wherein heteroaryl or benzo-fused heteroaryl is optionally substituted with one substituent selected from the group consisting of cyclohexyl, $C_{1-4}$alkyl, phenyl, and trifluoromethyl; or (i) 1,5-diphenyl-1H-pyrazol-3-yl wherein the pyrazol-3-yl is optionally substituted with one methyl substituent; and wherein the 1,5-phenyl substituents are each optionally independently substituted with one to two chloro substituents or aminosulfonyl.

As used herein, (Z-f) shall mean that Z is selected from the group consisting of (a) phenyl substituted with $NR^aR^b$; wherein $R^a$ is hydrogen or $C_{1-4}$alkyl; and $R^b$ is $C_{1-4}$alkyl, cycloalkyl, or phenyl; and wherein the phenyl of $R^b$ is optionally substituted with one iodo substituent; or $R^a$ and $R^b$ are taken together with the nitrogen atom to which they are both bound to form a 5 to 8 membered heterocyclyl;

(b) biphenyl-3-yl or biphenyl-4-yl; wherein the interior phenyl ring, attached to the carbonyl of Formula (I) as herein defined, of said biphenyl-3-yl and biphenyl-4-yl is optionally substituted with one fluoro substituent; and wherein the terminal phenyl ring of said biphenyl-3-yl and biphenyl-4-yl is optionally substituted with one substituent selected from the group consisting of trifluoromethyl, $C_{1-4}$alkoxy, chloro, dichloro, fluoro, and iodo;

(c) phenyl substituted with one substituent selected from the group consisting of cyclohexyl, phenyloxy, phenyl($C_{1-3}$)alkoxy, 3-phenylmethyl, 4-phenylmethyl, or pyrrolyl;

(d) phenyl substituted with one to two substituents independently selected from the group consisting of $C_{1-4}$alkoxy, iodo, and $C_{1-6}$alkyl;

(e) phenyl($C_{1-2}$)alkyl; wherein the phenyl is optionally substituted with $NR^cR^d$; wherein $R^c$ is hydrogen or $C_{1-4}$alkyl and $R^d$ is $C_{1-4}$alkyl or $C_{3-6}$cycloalkyl($C_{1-4}$alkyl; or (f) 2-phenyl-vinyl; wherein the phenyl is optionally substituted with trifluoromethylthio;

(g) benzofused cyclohexyl($C_{1-4}$)alkyl, wherein the cyclohexyl is optionally substituted with 1 to 4 methyl substituents; or (h) heteroaryl or benzo-fused heteroaryl selected from the group consisting of benzoxazolyl and indolyl; wherein heteroaryl or benzo-fused heteroaryl is optionally substituted with one substituent selected from the group consisting of cyclohexyl, $C_{1-4}$alkyl, phenyl, and trifluoromethyl.

In another embodiment, the present invention is directed to a compound of Formula (I)

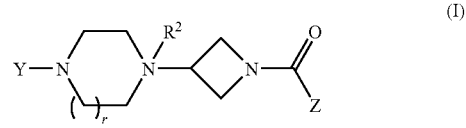

wherein the compound of Formula (I) is selected from the group consisting of a compound wherein Y is pyridin-2-yl, Z is (3-fluoro-4-phenyl)phenyl, r is 1, and $R^2$ is absent;

a compound wherein Y is pyrimidin-2-yl, Z is (2-cyclohexyl)benzoxazol-6-yl, r is 1, and $R^2$ is absent;

a compound wherein Y is pyridin-2-yl, Z is 4-phenylmethyl-phenyl, r is 1, and $R^2$ is absent;

a compound wherein Y is pyridin-2-yl, Z is 3-(phenylcarbonyl)phenyl, r is 1, and $R^2$ is absent;

a compound wherein Y is pyridin-2-yl, Z is 4-(phenylcarbonyl)phenyl, r is 1, and $R^2$ is absent;

a compound wherein Y is pyridin-2-yl, Z is biphenyl-4-ylmethyl, r is 1, and $R^2$ is absent;

a compound wherein Y is pyridin-2-yl, Z is 3-(4-fluorophenyl)phenyl, r is 1, and $R^2$ is absent;

a compound wherein Y is pyridin-2-yl, Z is 9H-fluoren-1-yl, r is 1, and $R^2$ is absent;

a compound wherein Y is pyridin-2-yl, Z is fluoren-9-on-2-yl, r is 1, and $R^2$ is absent;
a compound wherein Y is pyridin-2-yl, Z is biphenyl-3-yl, r is 1, and $R^2$ is absent;
a compound wherein Y is pyridin-2-yl, Z is quinolin-6-yl, r is 1, and $R^2$ is absent;
a compound wherein Y is pyridin-2-yl, Z is 1H-indol-5-yl, r is 1, and $R^2$ is absent;
a compound wherein Y is pyridin-2-yl, Z is 1,2,3,4-tetrahydro-quinolin-6-yl, r is 1, and $R^2$ is absent;
a compound wherein Y is pyridin-2-yl, Z is 3-methyl-benzofuran-2-yl, r is 1, and $R^2$ is absent;
a compound wherein Y is pyridin-2-yl, Z is 5-phenyl-furan-2-yl, r is 1, and $R^2$ is absent;
a compound wherein Y is pyridin-2-yl, Z is 5-(3-trifluoromethyl-phenyl)furan-2-yl, r is 1, and $R^2$ is absent;
a compound wherein Y is pyridin-2-yl, Z is 5-(4-methoxyphenyl)furan-2-yl, r is 1, and $R^2$ is absent;
a compound wherein Y is pyridin-2-yl, Z is 5-(phenylethynyl)furan-2-yl, r is 1, and $R^2$ is absent;
a compound wherein Y is pyridin-2-yl, Z is 5-(4-methylphenyl)furan-2-yl, r is 1, and $R^2$ is absent;
a compound wherein Y is pyridin-2-yl, Z is biphenyl-4-yl, r is 1, and $R^2$ is absent;
a compound wherein Y is pyridin-2-yl, Z is 4-(cyclohexylcarbonylamino)phenyl, r is 1, and $R^2$ is absent;
a compound wherein Y is pyridin-2-yl, Z is (4-phenoxy)phenyl, r is 1, and $R^2$ is absent;
a compound wherein Y is pyridin-2-yl, Z is 1-propyl-indol-5-yl, r is 1, and $R^2$ is absent;
a compound wherein Y is pyridin-2-yl, Z is 2-(1-cyclohexyl-2,3-dihydro-1H-indol-5-yl)-vinyl, r is 1, and $R^2$ is absent;
a compound wherein Y is pyridin-2-yl, Z is (4-azepan-1-yl)phenyl, r is 1, and $R^2$ is absent;
a compound wherein Y is pyridin-2-yl, Z is 4-(cyclohexylmethyl-amino)phenyl, r is 1, and $R^2$ is absent;
a compound wherein Y is pyridin-2-yl, Z is 4-(phenylmethyl-amino)phenyl, r is 1, and $R^2$ is absent;
a compound wherein Y is pyridin-2-yl, Z is 2-(4-(cyclohexylmethyl-methyl-amino)phenyl)-ethyl, r is 1, and $R^2$ is absent;
a compound wherein Y is pyridin-2-yl, Z is 2-(1,1,4,4-tetramethyl-1,2,3,4-tetrahydro-naphth-6-yl)ethyl, r is 1, and $R^2$ is absent;
a compound wherein Y is pyridin-2-yl, Z is 4-(1,1-dimethyl-propyl)-phenyl, r is 1, and $R^2$ is absent;
a compound wherein Y is pyridin-2-yl, Z is 2-(4-t-butyl-phenyl)ethyl, r is 1, and $R^2$ is absent;
a compound wherein Y is pyridin-2-yl, Z is 2-(4-trifluoromethylthio-phenyl)-vinyl, r is 1, and $R^2$ is absent;
a compound wherein Y is pyridin-2-yl, Z is 5-(4-chlorophenyl)-1-(3,4-dichloro-phenyl)-1H-pyrazol-3-yl, r is 1, and $R^2$ is absent;
a compound wherein Y is pyridin-2-yl, Z is 5-(4-chlorophenyl)-1-(4-aminosulfonyl-phenyl)-1H-pyrazol-3-yl, r is 1, and $R^2$ is absent;
a compound wherein Y is pyridin-2-yl, Z is 5-(4-chlorophenyl)-1-(2,4-dichloro-phenyl)-4-methyl-1H-pyrazol-3-yl, r is 1, and $R^2$ is absent;
a compound wherein Y is pyridin-2-yl, Z is 2-phenyl-5-trifluoromethyl-oxazol-4-yl, r is 1, and $R^2$ is absent;
a compound wherein Y is pyridin-2-yl, Z is 5-(phenylmethoxy)indol-2-yl, r is 1, and $R^2$ is absent;
a compound wherein Y is pyridin-2-yl, Z is 4-phenylmethoxy-1H-indol-2-yl, r is 1, and $R^2$ is absent;
a compound wherein Y is pyridin-2-yl, Z is 4-n-butyl-phenyl, r is 1, and $R^2$ is absent;
a compound wherein Y is pyridin-2-yl, Z is (4-cyclohexyl)phenyl, r is 1, and $R^2$ is absent;
a compound wherein Y is pyridin-2-yl, Z is (3-phenoxy)phenyl, r is 1, and $R^2$ is absent;
a compound wherein Y is pyridin-2-yl, Z is (4-phenylmethoxy)phenyl, r is 1, and $R^2$ is absent;
a compound wherein Y is pyridin-2-yl, Z is (2-phenylmethoxy)phenyl, r is 1, and $R^2$ is absent;
a compound wherein Y is pyridin-2-yl, Z is 4-(isoindol-1,3-dion-2-yl)phenyl, r is 1, and $R^2$ is absent;
a compound wherein Y is pyridin-2-yl, Z is 6-methoxynaphth-2-yl, r is 1, and $R^2$ is absent;
a compound wherein Y is pyridin-2-yl, Z is 1,2-diphenylethyl, r is 1, and $R^2$ is absent;
a compound wherein Y is pyridin-2-yl, Z is (3-phenoxy)phenylmethyl, r is 1, and $R^2$ is absent;
a compound wherein Y is pyridin-2-yl, Z is 4-(1-t-butoxycarbonyl)piperidin-4-yl)phenyl, r is 1, and $R^2$ is absent;
a compound wherein Y is pyridin-2-yl, Z is 4-(1-t-butoxycarbonyl)piperidin-4-yloxy)phenyl, r is 1, and $R^2$ is absent;
a compound wherein Y is pyrimidin-2-yl, Z is biphenyl-4-yl, r is 1, and $R^2$ is absent;
a compound wherein Y is pyrimidin-2-yl, Z is (4-phenoxy)phenyl, r is 1, and $R^2$ is absent;
a compound wherein Y is pyrimidin-2-yl, Z is 4-iodo-3-methyl-phenyl, r is 1, and $R^2$ is absent;
a compound wherein Y is pyrimidin-2-yl, Z is (3-fluoro-4-phenyl)phenyl, r is 1, and $R^2$ is absent;
a compound wherein Y is pyrimidin-2-yl, Z is (4-phenylmethyl)phenyl, r is 1, and $R^2$ is absent;
a compound wherein Y is pyridin-2-yl, Z is 4-t-butyl-cyclohexyl, r is 1, and $R^2$ is absent;
a compound wherein Y is pyridin-2-yl, Z is 4-n-pentyl-cyclohexyl, r is 1, and $R^2$ is absent;
a compound wherein Y is pyridin-2-yl, Z is 2-(4-isopropyl-phenyl)-vinyl, r is 1, and $R^2$ is absent;
a compound wherein Y is pyridin-2-yl, Z is 2-(3-trifluoromethylphenyl)-vinyl, r is 1, and $R^2$ is absent;
a compound wherein Y is pyridin-2-yl, Z is 2-(biphenyl-4-yl)-vinyl, r is 1, and $R^2$ is absent;
a compound wherein Y is pyridin-2-yl, Z is 5-n-butyl-pyridin-2-yl, r is 1, and $R^2$ is absent;
a compound wherein Y is pyridin-2-yl, Z is quinolin-2-yl, r is 1, and $R^2$ is absent;
a compound wherein Y is pyridin-2-yl, Z is 4-phenyl-5-trifluoromethyl-thien-2-yl, r is 1, and $R^2$ is absent;
a compound wherein Y is pyridin-2-yl, Z is 3-(1,3-dihydro-isoindol-2-yl)phenyl, r is 1, and $R^2$ is absent;
a compound wherein Y is 3-iodo-pyridin-2-yl, Z is (4-cyclohexyl)phenyl, r is 1, and $R^2$ is absent;
a compound wherein Y is pyrimidin-2-yl, Z is 4-iodo-phenyl, r is 1, and $R^2$ is absent;
a compound wherein Y is pyrimidin-2-yl, Z is (4-phenylmethoxy)phenyl, r is 1, and $R^2$ is absent;
a compound wherein Y is pyrimidin-2-yl, Z is (4-cyclohexyl)phenyl, r is 1, and $R^2$ is absent;
a compound wherein Y is 3-iodo-pyridin-2-yl, Z is (4-phenylmethoxy)phenyl, r is 1, and $R^2$ is absent;
a compound wherein Y is 3-iodo-pyridin-2-yl, Z is (4-phenylmethyl)phenyl, r is 1, and $R^2$ is absent;
a compound wherein Y is pyridin-2-yl, Z is 1-phenyl-1H-pyrazol-4-yl, r is 1, and $R^2$ is absent;
a compound wherein Y is pyrimidin-2-yl, Z is 1,5-diphenyl-1H-pyrazol-3-yl, r is 1, and $R^2$ is absent;

a compound wherein Y is pyridin-2-yl, Z is 4-diethylamino-phenyl, r is 1, and $R^2$ is absent;
a compound wherein Y is pyridin-2-yl, Z is 2-(3-ethoxyphenyl)-vinyl, r is 1, and $R^2$ is absent;
a compound wherein Y is pyridin-2-yl, Z is 2-phenyl-1H-benzimidazol-5-yl, r is 1, and $R^2$ is absent;
a compound wherein Y is thiazol-2-yl, Z is (4-cyclohexyl)phenyl, r is 1, and $R^2$ is absent;
a compound wherein Y is benzothiazol-2-yl, Z is (4-cyclohexyl)phenyl, r is 1, and $R^2$ is absent;
a compound wherein Y is benzoxazol-2-yl, Z is (4-cyclohexyl)phenyl, r is 1, and $R^2$ is absent;
a compound wherein Y is 5-bromo-pyridin-2-yl, Z is (4-cyclohexyl)phenyl, r is 1, and $R^2$ is absent;
a compound wherein Y is pyrimidin-2-yl, Z is 3-iodo-4-methyl-phenyl, r is 1, and $R^2$ is absent;
a compound wherein Y is pyrimidin-2-yl, Z is 4-chloro-3-iodophenyl, r is 1, and $R^2$ is absent;
a compound wherein Y is pyrimidin-2-yl, Z is 3-iodo-4-methoxyphenyl, r is 1, and $R^2$ is absent;
a compound wherein Y is pyrimidin-2-yl, Z is 2-(3-iodophenyl)ethyl, r is 1, and $R^2$ is absent;
a compound wherein Y is pyrimidin-2-yl, Z is 2-(4-iodophenyl)ethyl, r is 1, and $R^2$ is absent;
a compound wherein Y is 3-chloro-pyridin-2-yl, Z is (4-cyclohexyl)phenyl, r is 1, and $R^2$ is absent;
a compound wherein Y is 5-chloro-pyridin-2-yl, Z is (4-cyclohexyl)phenyl, r is 1, and $R^2$ is absent;
a compound wherein Y is benzo[d]isoxazol-3-yl, Z is (4-cyclohexyl)phenyl, r is 1, and $R^2$ is absent;
a compound wherein Y is 5-trifluoromethyl-1,3,4-thiadiazol-2-yl, Z is 4-cyclohexyl-phenyl, r is 1, and $R^2$ is absent;
a compound wherein Y is 1,3,5-triazin-2-yl, Z is (4-cyclohexyl)phenyl, r is 1, and $R^2$ is absent;
a compound wherein Y is 4-methyl-pyridin-2-yl, Z is (4-cyclohexyl)phenyl, r is 1, and $R^2$ is absent;
a compound wherein Y is 3-methyl-pyridin-2-yl, Z is (4-cyclohexyl)phenyl, r is 1, and $R^2$ is absent;
a compound wherein Y is 3-cyano-pyridin-2-yl, Z is (4-cyclohexyl)phenyl, r is 1, and $R^2$ is absent;
a compound wherein Y is 5-cyano-pyridin-2-yl, Z is (4-cyclohexyl)phenyl, r is 1, and $R^2$ is absent;
a compound wherein Y is 3-trifluoromethyl-pyridin-2-yl, Z is (4-cyclohexyl)phenyl, r is 1, and $R^2$ is absent;
a compound wherein Y is pyrimidin-2-yl, Z is biphenyl-4-yl, r is 1, and $R^2$ is oxo
a compound wherein Y is 4-methyl-pyridin-2-yl, Z is biphenyl-4-yl, r is 1, and $R^2$ is absent;
a compound wherein Y is 3-cyano-pyridin-2-yl, Z is biphenyl-4-yl, r is 1, and $R^2$ is absent;
a compound wherein Y is 3-trifluoromethyl-pyridin-2-yl, Z is biphenyl-4-yl, r is 1, and $R^2$ is absent;
a compound wherein Y is thiazol-2-yl, Z is biphenyl-4-yl, r is 1, and $R^2$ is absent;
a compound wherein Y is benzothiazol-2-yl, Z is biphenyl-4-yl, r is 1, and $R^2$ is absent;
a compound wherein Y is benzoxazol-2-yl, Z is biphenyl-4-yl, r is 1, and $R^2$ is absent;
a compound wherein Y is 5-bromo-pyridin-2-yl, Z is biphenyl-4-yl, r is 1, and $R^2$ is absent;
a compound wherein Y is pyrimidin-2-yl, Z is 4-(4-fluorophenyl)phenyl, r is 1, and $R^2$ is absent;
a compound wherein Y is pyrimidin-2-yl, Z is 4-(2-chlorophenyl)phenyl, r is 1, and $R^2$ is absent;
a compound wherein Y is pyrimidin-2-yl, Z is 4-(3,4-dichlorophenyl)phenyl, r is 1, and $R^2$ is absent;
a compound wherein Y is pyrimidin-2-yl, Z is 4-(3-trifluoromethylphenyl)phenyl, r is 1, and $R^2$ is absent;
a compound wherein Y is pyrimidin-2-yl, Z is 4-(4-methoxyphenyl)phenyl, r is 1, and $R^2$ is absent;
a compound wherein Y is pyrimidin-2-yl, Z is 4-dimethylamino-phenyl, r is 1, and $R^2$ is absent;
a compound wherein Y is pyrimidin-2-yl, Z is (4-pyrrol-1-yl)phenyl, r is 1, and $R^2$ is absent;
a compound wherein Y is pyrimidin-2-yl, Z is (4-pyrazol-1-yl)phenyl, r is 1, and $R^2$ is absent;
a compound wherein Y is pyrimidin-2-yl, Z is (4-imidazol-1-yl)phenyl, r is 1, and $R^2$ is absent;
a compound wherein Y is pyrimidin-2-yl, Z is (4-pyrrolidin-1-yl)phenyl, r is 1, and $R^2$ is absent;
a compound wherein Y is pyrimidin-2-yl, Z is 1-isopropyl-2-trifluoromethyl-1H-benzimidazol-5-yl, r is 1, and $R^2$ is absent;
a compound wherein Y is pyrimidin-2-yl, Z is 2-methyl-1-phenyl-1H-benzimidazol-5-yl, r is 1, and $R^2$ is absent;
a compound wherein Y is pyrimidin-2-yl, Z is 1-cyclohexyl-2-methyl-1H-benzimidazol-5-yl, r is 1, and $R^2$ is absent;
a compound wherein Y is pyrimidin-2-yl, Z is 4-nitrophenyl, r is 1, and $R^2$ is absent;
a compound wherein Y is pyrimidin-2-yl, Z is 4-(2-iodophenylmethylamino)phenyl, r is 1, and $R^2$ is absent;
a compound wherein Y is pyrimidin-2-yl, Z is 4-(5-iodofuran-2-ylmethylamino)phenyl, r is 1, and $R^2$ is absent;
a compound wherein Y is pyrimidin-2-yl, Z is 4-(4-iodophenyl)phenyl, r is 1, and $R^2$ is absent;
a compound wherein Y is 2-methoxyphenyl, Z is biphenyl-4-yl, r is 1, and $R^2$ is absent;
a compound wherein Y is 2-methylthiophenyl, Z is biphenyl-4-yl, r is 1, and $R^2$ is absent;
a compound wherein Y is 2-nitrophenyl, Z is biphenyl-4-yl, r is 1, and $R^2$ is absent;
a compound wherein Y is pyrimidin-2-yl, Z is biphenyl-4-yl, r is 2, and $R^2$ is absent;
a compound wherein Y is pyrimidin-2-yl, Z is (4-pyrrolidin-1-yl)phenyl, r is 2, and $R^2$ is absent;
a compound wherein Y is pyrimidin-2-yl, Z is (4-phenylmethyl)phenyl, r is 2, and $R^2$ is absent;
a compound wherein Y is pyrimidin-2-yl, Z is 6-trifluoromethyl-benzothien-2-yl, r is 1, and $R^2$ is absent;

and enantiomers, diastereomers, solvates and pharmaceutically acceptable salt forms thereof.

In another embodiment, the present invention is directed to a compound of formula (I) wherein Y is pyrimidin-2-yl, r is 1, $R^2$ is absent and Z is biphen-4-yl; or a pharmaceutically acceptable salt thereof.

In an embodiment, the present invention is directed to treating, ameliorating or preventing a disease, syndrome, condition or disorder that is affected by inhibition of MGL, wherein the disease, syndrome, condition or disorder that is affected by inhibition of MGL is selected from the group consisting of inflammatory pain and neuropathic pain; comprising administering to a subject in need thereof (including a mammal and/or human), a therapeutically effective amount of a compound of Formula (I)

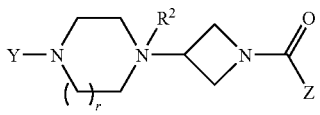

selected from the group as herein defined; and enantiomers, diastereomers, solvates and pharmaceutically acceptable salt thereof.

In an embodiment, the present invention is directed to treating, ameliorating or preventing inflammatory pain; comprising administering to a subject in need thereof (including a mammal and/or human), a therapeutically effective amount of a compound of Formula (I)

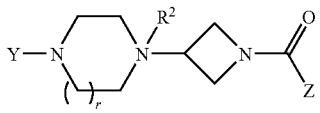

selected from the group as herein defined; and enantiomers, diastereomers, solvates and pharmaceutically acceptable salt thereof. In another embodiment of the present invention, the inflammatory pain is selected from the group consisting of visceral pain and inflammatory hyeralgesia, preferably visceral pain.

In an embodiment, the present invention is directed to treating, ameliorating or preventing inflammatory hyperalgesia, comprising administering to a subject in need thereof (including a mammal and/or human), a therapeutically effective amount of a compound of Formula (I)

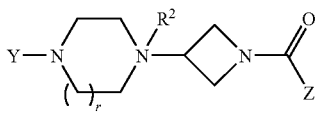

selected from the group as herein defined; and enantiomers, diastereomers, solvates and pharmaceutically acceptable salt thereof. In another embodiment of the present invention, the inflammatory hyperalgesia is ulcerative colitis.

In an embodiment, the present invention is directed to treating, ameliorating or preventing neuropathic pain, comprising administering to a subject in need thereof (including a mammal and/or human), a therapeutically effective amount of a compound of Formula (I)

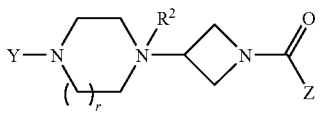

as herein defined; and enantiomers, diastereomers, solvates and pharmaceutically acceptable salt thereof. In another embodiment of the present invention, the neuropathic pain is neuropathic cold allodynia.

For use in medicine, salts of compounds of Formula (I) as herein defined refer to non-toxic "pharmaceutically acceptable salts." Other salts may, however, be useful in the preparation of compounds of formula (I) or of their pharmaceutically acceptable salts thereof. Suitable pharmaceutically acceptable salts of compounds of Formula (I) as herein defined include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) as herein defined carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids such as acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of Formula (I) as herein defined. In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I) as herein defined.

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\% \ (+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\% \ (-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry*, Second Edition, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) as herein defined and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) as herein defined may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) as herein defined can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as herein defined can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of Formula (I) as herein defined or a pharmaceutical composition thereof includes a dose range from about 0.1 mg to about 3000 mg, or any amount or range therein, in particular from about 1 mg to about 1000 mg, or any amount or range therein, more particularly, from about 10 mg to about 500 mg, or any amount or range therein, of ingredient compound of Formula (I) as herein defined in a regimen of about 1 to 4 times per day for an average (70 kg) human; although, it is apparent to one skilled in the art that the therapeutically effective amount for a compound of Formula (I) as herein defined will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of Formula (I) as herein defined.

Advantageously, a compound of Formula (I) as herein defined may be administered in a single daily dose, or the total daily dosage may be administered in divided doses of two, three and four times daily.

Optimal dosages of a compound of Formula (I) as herein defined to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

A compound of Formula (I) as herein defined may be administered in any of the foregoing compositions and dosage regimens or by means of those compositions and dosage regimens established in the art whenever use of a compound of Formula (I) as herein defined is required for a subject in need thereof.

General Synthetic Methods

Representative compounds of the present invention may be synthesized in accordance with the general synthetic methods described below and illustrated in the schemes that follow. Since the schemes are an illustration, the invention should not be construed as being limited by the specific chemical reactions and specific conditions described in the schemes and examples. The various starting materials used in the schemes are commercially available or may be prepared by methods well within the skill of persons versed in the art. The variables are as defined herein and within the skill of persons versed in the art.

Compounds of Formula (I) wherein $R^2$ is absent may be prepared according to the process outlined in Scheme 1, below.

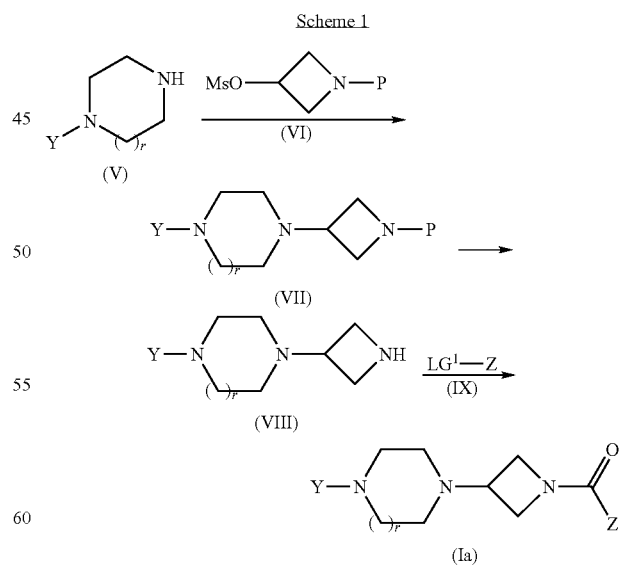

Accordingly, a suitably substituted compound of formula (V), a known compound or compound prepared by known methods, is reacted with a suitably substituted compound of formula (VI), wherein P is a suitably selected nitrogen protecting group such as —CH(phenyl)$_2$, benzyl, t-butyl, methyl, and the like, preferably —CH(phenyl)$_2$, a known compound or compound prepared by known methods; in the presence of an organic base such as DIPEA, TEA, pyridine, and the like; in an organic solvent such as acetonitrile, THF, DCM, and the like; preferably at a temperature in the range of from about 50° C. to about 90° C.; to yield the corresponding compound of formula (VII).

The compound of formula (VII) is de-protected according to known methods, to yield the corresponding compound of formula (VIII). For example, wherein P is —CH(phenyl)$_2$, the compound of formula (VII) is de-protected by reacting with 1-chloroethyl chloroformate, in an organic solvent such as dichloromethane, and then refluxed in an organic solvent such as methanol, to yield the corresponding compound of formula (VIII).

The compound of formula (VIII) is reacted with a suitably substituted compound of formula (IX), wherein LG$^1$ is selected from the group consisting of —C(O)Cl and —C(O)OH, and wherein LG$^1$ is bound at the desired bonding position on benzene ring of the benzo-fused portion of the compound of formula (IX), a known compound or compound prepared by known methods, in the presence of a suitably selected coupling agent such as HATU, HBTU, DCC, and the like; optionally in the presence of a suitably selected organic base such as DIPEA, TEA, pyridine, and the like; in an organic solvent such as acetonitrile, DMF, DCM, and the like; to yield the corresponding compound of formula (Ia).

Compounds of Formula (I) wherein R$^2$ is oxo may be prepared according to the process outlined in Scheme 2, below.

Scheme 2

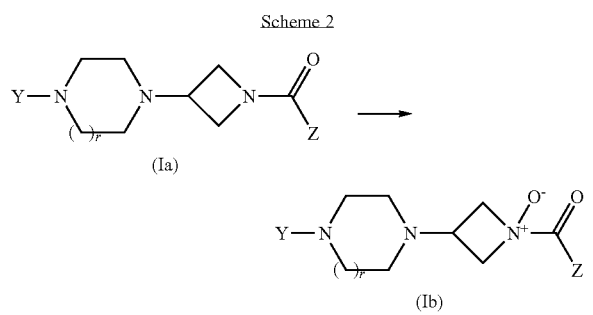

Accordingly, a suitably substituted (and as necessary and/or desirable, suitably protected) compound of formula (Ia) is oxidized to yield the corresponding compound of formula (Ib). More particularly, a suitably substituted compound of formula (Ia) is reacted with a suitably selected oxidizing agent, such as mCPBA, H$_2$O$_2$, and the like, in a solvent such as DCM, chloroform, acetic acid, and the like; preferably at about room temperature; to yield the corresponding compound of formula (Ib).

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

Compound #12

Biphenyl-4-yl-[3-(4-pyrimidin-2-yl-piperazin-1-yl)-azetidin-1-yl]-methanone

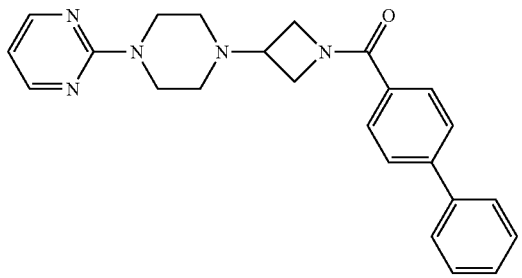 [SMILES: O=C(c1ccc(-c2ccccc2)cc1)N1CC(N2CCN(c3ncccn3)CC2)C1]

STEP A: 2-[4-(1-Benzhydryl-azetidin-3-yl)-piperazin-1-yl]-pyrimidine

To a solution of 2-piperazin-1-yl-pyrimidine (2.48 g, 15.10 mmol, Alfa) and methanesulfonic acid 1-benzhydryl-azetidin-3-yl ester (4 g, 12.6 mmol, Oakwood) in CH$_3$CN (40 mL) was added DIPEA (2.63 mL, 15.10 mmol) at room temperature. The resulting mixture was then refluxed for 2 h. The solvent was removed by evaporation and the residue was partitioned between CH$_2$Cl$_2$ and aqueous NaHCO$_3$. The organic layer was washed with aqueous NaHCO$_3$ (2×) and then extracted with 1N HCl (2×). The aqueous layer was cooled and then pH adjusted with 1N NaOH. The resulting mixture was extracted with CH$_2$Cl$_2$ (2×). The organic layer was dried over MgSO$_4$ and concentrated. The resulting residue was purified by MPLC to yield 2-[4-(1-benzhydryl-azetidin-3-yl-piperazin-1-yl]-pyrimidine.

STEP B:
2-(4-Azetidin-3-yl-piperazin-1-yl)-pyrimidine

To a solution of 2-[4-(1-benzhydryl-azetidin-3-yl)-piperazin-1-yl]-pyrimidine (2.03 g, 5.27 mmol) in CH$_2$Cl$_2$ (20 mL) was added 1-chloroethyl chloroformate (1.704 mL, 15.79 mmol) at 0° C. under N$_2$. The resulting mixture was stirred at 0° C. for 90 min and then methanol (4 mL) was added. The resulting mixture was refluxed for 1 h, then cooled. Diethyl ether (40 mL) was added to the resulting mixture. The solid was filtered and dried to yield 2-(4-azetidin-3-yl-piperazin-1-yl)-pyrimidine, which was used in the next step without further purification.

STEP C: Biphenyl-4-yl-[3-(4-pyrimidin-2-yl-piperazin-1-yl)-azetidin-1-yl]-methanone To a solution of 2-(4-azetidin-3-yl-piperazin-1-yl)-pyrimidine (0.172 g, 0.87 mmol) and HATU (0.347 g, 0.913 mmol) in DMF (4 mL) was added DIPEA (0.607 mL, 3.48 mmol). The mixture was stirred at room temperature for 30 min and then biphenyl-4-carboxylic acid (0.87 mmol) was added. The resulting mixture was stirred at room temperature for 5 h.

H₂O (8 mL) was added and the resulting mixture extracted with EtOAc (3×). The organic layer was dried over MgSO₄ and concentrated. The resulting residue was purified by HPLC to yield biphenyl-4-yl-[3-(4-pyrimidin-2-yl-piperazin-1-yl)-azetidin-1-yl]-methanone.

Following the procedure as described in Example 1, above and substituting suitably selected and/or substituted reagents, starting materials and purification methods known to those skilled in the art, the following compounds of the present invention were prepared:

| Cmpd No. | Compound Name<br>Measured Physical Properties of Prepared Sample |
|---|---|
| 1 | N-Cyclohexyl-N-methyl-4-{[3-(4-pyridin-2-ylpiperazin-1-yl)azetidin-1-yl]carbonyl}aniline<br>¹H NMR (300 MHz, CD3CN) δ 8.12 (d, J = 4.9 Hz, 1H), 8.01 (ddd, J = 1.9, 7.2, 9.0 Hz, 1H), 7.63 (d, J = 9.0 Hz, 2H), 7.22 (d, J = 8.7 Hz, 3H), 7.02 (t, J = 6.6 Hz, 1H), 4.24-4.75 (m, 4H), 4.00 (t, J = 5.1 Hz, 5H), 3.53-3.73 (m, 1H), 3.30 (m, 4H), 3.01 (s, 3 H), 1.85 (d, J = 9.8 Hz, 4H), 1.58-1.72 (m, 1H), 1.24-1.59 (m, 4 H), 1.03-1.24 (m, 1H); LC/MS m/z (M + H+) 434.4 (calculated for C26H35N5O, 431.56) |
| 2 | 2-(4-{1-[(4-Pyrrolidin-1-ylphenyl)carbonyl]azetidin-3-yl}piperazin-1-yl)pyrimidine<br>¹H NMR (300 MHz, CD3OD) δ 8.32 (d, 2H), 7.47 (d, 2H), 6.65 (t, 1H), 6.49 (d, 2H), 4.25-4.64 (m, 4H), 3.82-4.19 (m, 5H), 3.16-3.32 (m, 8H), 1.89-2.02 (m, 4H); LC/MS m/z (M + H+) 393.3 (calculated for C22H28N6O, 392.51) |
| 3 | 1-(4-{[3-(4-Pyridin-2-ylpiperazin-1-yl)azetidin-1-yl]carbonyl}phenyl)azepane<br>¹H NMR (300 MHz, CD3CN) δ 8.11 (d, J = 6.0 Hz, 1H), 7.91-8.07 (m, 1H), 7.48 (d, J = 9.0 Hz, 2H), 7.21 (d, J = 9.4 Hz, 1H), 7.02 (t, J = 6.6 Hz, 1H), 6.71 (d, J = 9.0 Hz, 2H), 4.47 (m, 4H), 3.99 (d, J = 4.5 Hz, 5H), 3.40-3.60 (m, 4H), 3.31 (m, 4H), 1.78 (m, 4H), 1.52 (m, 4H); LC/MS m/z (M + H+) 420.3 (calculated for C25H33N5O, 419.57) |
| 4 | 2-[4-(1-{[3'-(Trifluoromethyl)biphenyl-4-yl]carbonyl}azetidin-3-yl)piperazin-1-yl]pyrimidine<br>¹H NMR (300 MHz, CD3OD) δ 8.32 (d, 2H), 7.78-7.91 (m, 2H), 7.72 (s, 4H), 7.51-7.67 (m, 2H), 6.65 (t, 1H), 4.51-4.72 (m, 2H), 4.28-4.51 (m, 2H), 3.92-4.18 (m, 5H), 3.22-3.35 (m, 4H); LC/MS m/z (M + H+) 468.1 (calculated for C25H24F3N5O, 467.5) |
| 5 | 2-(4-{1-[(4'-Methoxybiphenyl-4-yl)carbonyl]azetidin-3-yl}piperazin-1-yl)pyrimidine<br>¹H NMR (300 MHz, CD3OD) δ 8.32 (d, 2H), 7.63 (s, 4H), 7.52 (d, 2H), 6.93 (d, 2H), 6.65 (t, 1H), 4.50-4.71 (m, 2H), 4.25-4.49 (m, 2H), 3.95-4.20 (m, 5H), 3.75 (s, 3H), 3.22-3.37 (m, 4H); LC/MS m/z (M + H+) 430.2 (calculated for C25H27N5O2, 429.53) |
| 6 | 1-{1-[(4-Cyclohexylphenyl)carbonyl]azetidin-3-yl}-4-(1,3-thiazol-2-yl)piperazine<br>¹H NMR (300 MHz, CD3OD) δ 7.58 (d, J = 8.3 Hz, 2H), 7.21-7.41 (m, 3H), 6.98 (d, J = 4.1 Hz, 1H), 4.19-4.70 (m, 4H), 3.91 (m, 1H), 3.68-3.85 (m, 4H), 3.16 (m, 4H), 2.58 (m, 1H), 1.68-1.96 (m, 5H), 1.19-1.57 (m, 5H); LC/MS m/z (M + H+) 411.3 (calculated for C23H30N4OS, 410.59) |
| 7 | N-(2-Iodobenzyl)-4-{[3-(4-pyrimidin-2-ylpiperazin-1-yl)azetidin-1-yl]carbonyl}aniline<br>¹H NMR (400 MHz, DMSO-d6) δ 8.45 (d, J = 4.9 Hz, 2H), 7.87-7.92 (m, 1H), 7.44 (d, J = 8.8 Hz, 2H), 7.33-7.40 (m, 1H), 7.27-7.33 (m, 1H), 7.01-7.08 (m, 1H), 6.77 (s, 1H), 6.55 (d, J = 8.8 Hz, 2H), 4.62-4.77 (m, 2H), 4.31-4.59 (m, 4H), 4.26 (s, 2H), 4.00-4.11 (m, 2H), 3.57 (m, 1H), 3.10-3.35 (m, 2H), 2.88-3.10 (m, 2H); MS m/z (M + H+) 555.1 |
| 8 | 2-(4-{1-[(2'-Chlorobiphenyl-4-yl)carbonyl]azetidin-3-yl}piperazin-1-yl)pyrimidine<br>¹H NMR (300 MHz, CD3OD) δ 8.32 (d, 2H), 7.67 (d, 2H), 7.37-7.53 (m, 3H), 7.121-7.36 (m, 3H), 6.65 (t, 1H), 4.54-4.72 (m, 2 H), 4.27-4.50 (m, 2H), 3.90-4.21 (m, 5H), 3.22-3.36 (m, 4H); LC/MS m/z (M + H+) 434.1 (calculated for C24H24ClN5O, 433.94) |
| 9 | 2-(4-{1-[(4'-Fluorobiphenyl-4-yl)carbonyl]azetidin-3-yl}piperazin-1-yl)pyrimidine<br>¹H NMR (300 MHz, CD3OD) δ 8.32 (d, J = 4.9 Hz, 2H), 7.53-7.70 (m, 6H), 7.11 (t, 2H), 6.65 (t, 1H), 4.52-4.69 (m, 2H), 4.28-4.47 (m, 2H), 3.89-4.19 (m, 5H), 3.21-3.36 (m, 4H); LC/MS m/z (M + H+) 418.1 (calculated for C24H24N5O, 417.49) |
| 10 | 2-Cyclohexyl-6-{[3-(4-pyrimidin-2-ylpiperazin-1-yl)azetidin-1-yl]carbonyl}-1,3-benzoxazole<br>¹H NMR (300 MHz, CDCl3): δ 8.31 (d, J = 4.9 Hz, 2H), 7.80 (s, 1 H), 7.64-7.73 (m, 1H), 7.53-7.64 (m, 1H), 6.51 (t, J = 4.7 Hz, 1 H), 4.05-4.42 (m, 4H), 3.87 (t, J = 4.9 Hz, 4H), 3.18-3.30 (m, 1 H), 2.92-3.06 (m, 1H), 2.30-2.54 (m, 4H), 2.10-2.24 (m, 2H), 1.81-1.95 (m, 2H), 1.67-1.81 (m, 2H), 1.22-153 (m, 4H); LC/MS m/z (M + H+) 447.3 (calculated for C25H30N6O2, 446.56) |

| Cmpd No. | Compound Name<br>Measured Physical Properties of Prepared Sample |
|---|---|
| 11 | 2-(4-{1-[(3',4'-Dichlorobiphenyl-4-yl)carbonyl]azetidin-3-yl}piperazin-1-yl)pyrimidine<br>$^1$H NMR (300 MHz, CD3OD) δ 8.32 (d, 2H), 7.76 (s, 1H), 7.69 (s, 4H), 7.46-7.58 (m, 2H), 6.65 (t, 1H), 4.50-4.70 (m, 2H), 4.25-4.48 (m, 2H), 3.89-4.13 (m, 5H), 3.19-3.37 (m, 4H); LC/MS m/z (M + H+) 468.1 (calculated for C24H23Cl2N5O, 468.39) |
| 12 | 2-{4-[1-(Biphenyl-4-ylcarbonyl)azetidin-3-yl]piperazin-1-yl}pyrimidine<br>$^1$H NMR (300 MHz, CD3CN) δ 8.31 (d, J = 4.5 Hz, 2H), 7.54-7.73 (m, 6H), 7.24-7.48 (m, 3H), 6.62 (t, J = 4.7 Hz, 1H), 4.19-4.69 (m, 4H), 3.82-4.18 (m, 5H), 2.84-3.42 (m, 4H); LC/MS m/z (M + H+) 400.2 (calculated for C24H25N5O, 399.5) |
| 13 | 2-(4-{1-[(4-Cyclohexylphenyl)carbonyl]azetidin-3-yl}piperazin-1-yl)pyrimidine<br>$^1$H NMR (400 MHz, DMSO-d6) δ = 8.44 (d, J = 4.9 Hz, 2H), 7.58 (d, J = 8.1 Hz, 2H), 7.34 (d, J = 8.3 Hz, 2H), 6.77 (t, J = 4.8 Hz, 1 H), 4.55 (m, 2H), 4.25-4.32 (m, 2H), 3.99-4.09 (m, 1H), 3.65 (br. s., 4H), 2.92-3.2 (br. s., 4H), 2.52-2.62 (m, 1H), 1.79 (dd, J = 3.1, 6.7 Hz, 4H), 1.67-1.75 (m, 1H), 1.40 (d, J = 10.5 Hz, 4H), 1.17-1.31 (m, 1H); MS m/z (M + H+) 406.3 |
| 14 | 2-Methyl-1-phenyl-5-{[3-(4-pyrimidin-2-ylpiperazin-1-yl)azetidin-1-yl]carbonyl}-1H-benzimidazole<br>$^1$H NMR (300 MHz, CD3OD) δ 8.31 (d, J = 4.9 Hz, 2H), 8.05 (s, 1H), 7.62-7.76 (m, 4H), 7.49-7.62 (m, 2H), 7.36 (d, J = 8.7 Hz, 1 H), 6.63 (t, J = 4.7 Hz, 1H), 4.55-4.75 (m, 2H), 4.35-4.53 (m, 2 H), 3.94-4.20 (m, 5H), 3.24 (m, 4H), 2.66 (s, 3H); LC/MS m/z (M + H+) 454.2 (calculated for C26H27N7O, 453.55) |
| 15 | 1-{1-[(4-Cyclohexylphenyl)carbonyl]azetidin-3-yl}-4-pyridin-2-ylpiperazine<br>$^1$H NMR (300 MHz, CD3CN) δ 8.02 (d, J = 4.9 Hz, 1H), 7.82 (ddd, J = 1.9, 7.2, 9.0 Hz, 1H), 7.44 (d, J = 8.3 Hz, 2H), 7.22 (d, J = 7.9 Hz, 2H), 7.03 (d, J = 9.0 Hz, 1H), 6.86 (t, J = 6.4 Hz, 1H), 4.12-4.54 (m, 4H), 3.67-3.95 (m, 5H), 3.11 (d, J = 1.9 Hz, 4H), 2.50 (m, 1H), 1.57-1.93 (m, 5H), 1.02-1.49 (m, 5H); LC/MS m/z (M + H+) 405.3 (calculated for C25H32N4O, 404.56) |
| 16 | 1-(1-Methylethyl)-5-{[3-(4-pyrimidin-2-ylpiperazin-1-yl)azetidin-1-yl]carbonyl}-2-(trifluoromethyl)-1H-benzimidazole<br>$^1$H NMR (300 MHz, CD3OD) δ 8.32 (d, J = 4.5 Hz, 2H), 7.02 (s, 1H), 7.94 (d, 1H), 7.70 (d, 1H), 6.65 (t, 1H), 4.92 (m, 1H), 4.52-4.73 (m, 2H), 4.28-4.52 (m, 2H), 3.83-4.21 (m, 5H), 3.23-3.39 (m, 4H), 1.64 (d, 6H); LC/MS m/z (M + H+) 474.3 (calculated for C23H26F3N7O, 473.51) |
| 17 | 1-Cyclohexyl-2-methyl-5-{[3-(4-pyrimidin-2-ylpiperazin-1-yl)azetidin-1-yl]carbonyl}-1H-benzimidazole<br>$^1$H NMR (300 MHz, CD3OD) δ 8.31 (d, J = 4.9 Hz, 2H), 8.09 (d, J = 8.7 Hz, 1H), 7.97 (s, 1H), 7.75 (d, J = 1.5 Hz, 1H), 6.64 (t, J = 4.9 Hz, 1H), 4.33-4.72 (m, 4H), 3.89-4.19 (m, 5H), 3.21-3.37 (m, 4H), 2.85 (s, 3H), 2.11-2.35 (m, 2H), 1.86-2.06 (m, 4H), 1.68-1.82 (m, 1H), 1.25-1.65 (m, 4H); LC/MS m/z (M + H+) 460.4 (calculated for C26H33N7O, 459.6) |
| 18 | N-Methyl-N-phenyl-4-{[3-(4-pyridin-2-ylpiperazin-1-yl)azetidin-1-yl]carbonyl}aniline<br>$^1$H NMR (300 MHz, CD3CN) δ 8.01 (d, J = 4.9 Hz, 1H), 7.86 (ddd, J = 1.9, 7.2, 9.0 Hz, 1H), 7.25-7.47 (m, 4H), 7.00-7.19 (m, 4H), 6.89 (t, J = 6.6 Hz, 1H), 6.69 (d, J = 9.0 Hz, 2H), 4.18-4.55 (m, 4H), 3.74-3.94 (m, 5H), 3.23 (s, 3H), 3.09-3.20 (m, 4H); LC/MS m/z (M + H+) 428.3 |
| 19 | 2-(4-{1-[(4'-Iodobiphenyl-4-yl)carbonyl]azetidin-3-yl}piperazin-1-yl)pyrimidine<br>$^1$H NMR (400 MHz, DMSO-d6) δ = 8.45 (d, J = 4.9 Hz, 2H), 7.87 (d, J = 8.6 Hz, 2H), 7.77 (q, J = 8.5 Hz, 4H), 7.54 (d, J = 8.3 Hz, 2H), 6.77 (s, 1H), 4.59-4.69 (m, 2H), 4.50-4.59 (m, 2H), 4.25-4.36 (m, 3H), 3.94-4.16 (m, 2H), 3.17-3.41 (m, 2H), 2.98 (br. s., 2H); MS m/z (M + H+) 526.1 |
| 20 | 2-(4-{1-[(4-Phenoxyphenyl)carbonyl]azetidin-3-yl}piperazin-1-yl)pyrimidine<br>$^1$H NMR (300 MHz, CD3CN) δ 8.31 (d, J = 4.9 Hz, 2H), 7.52 (d, J = 8.7 Hz, 2H), 7.34 (t, 2H), 7.13 (t, 1H), 6.98 (d, J = 7.9 Hz, 2 H), 6.91 (d, J = 8.7 Hz, 2H), 6.62 (t, J = 4.9 Hz, 1H), 3.75-4.72 (m, 9H), 3.12 (m, 4H); LC/MS m/z (M + H+) 416.2 (calculated for C24H25N5O2, 415.5) |

| Cmpd No. | Compound Name / Measured Physical Properties of Prepared Sample |
|---|---|
| 21 | 2-(4-{1-[(4-Cyclohexylphenyl)carbonyl]azetidin-3-yl}piperazin-1-yl)pyridine-3-carbonitrile<br>$^1$H NMR (300 MHz, CD3OD) δ 8.46 (dd, J = 1.9, 4.9 Hz, 1H), 8.04 (dd, J = 1.9, 7.9 Hz, 1H), 7.59 (d, J = 8.3 Hz, 2H), 7.34 (d, J = 7.9 Hz, 2H), 7.06 (dd, J = 4.9, 7.5 Hz, 1H), 4.57-4.78 (m, 2H), 4.34-4.56 (m, 2H), 4.22 (m, 1H), 3.93 (m, 4H), 3.44 (m, 4H), 2.58 (m, 1H), 1.69-1.96 (m, 5H), 1.19-1.58 (m, 5H); LC/MS m/z (M + H+) 430.2 (calculated for C26H31N5O, 429.57) |
| 22 | N-[(5-Iodofuran-2-yl)methyl]-4-{[3-(4-pyrimidin-2-ylpiperazin-1-yl)azetidin-1-yl]carbonyl}aniline<br>$^1$H NMR (400 MHz, MeOD) δ = 8.36-8.43 (m, 2H), 7.44-7.53 (m, 2H), 6.63-6.77 (m, 3H), 6.43-6.51 (m, 1H), 6.14-6.21 (m, 1H), 4.39-4.76 (m, 6H), 4.37 (s, 2H), 3.89-4.29 (m, 5H), 2.74 (br. s., 2 H); MS m/z (M + H+) |
| 23 | 2-{4-[1-(Biphenyl-4-ylcarbonyl)azetidin-3-yl]piperazin-1-yl}pyridine-3-carbonitrile<br>$^1$H NMR (300 MHz, CD3OD) δ 8.46 (dd, 1H), 8.04 (dd, 1H), 7.76 (s, 4H), 7.62-7.72 (m, 2H), 7.31-7.55 (m, 3H), 7.06 (dd, 1 H), 4.35-4.80 (m, 4H), 4.20 (m, 1H), 3.81-4.04 (m, 4H), 3.35-3.51 (m, 4H); LC/MS m/z (M + H+) 424.2 (calculated for C26H25N5O, 423.52) |
| 24 | 2-(4-{1-[(4-Benzylphenyl)carbonyl]azetidin-3-yl}piperazin-1-yl)pyrimidine<br>$^1$H NMR (400 MHz, DMSO-d6) δ = 8.44 (d, J = 4.6 Hz, 2H), 7.58 (d, J = 8.3 Hz, 2H), 7.35 (d, J = 8.1 Hz, 2H), 7.30 (d, J = 7.1 Hz, 2H), 7.27 (d, J = 1.7 Hz, 2H), 7.17-7.23 (m, 1H), 6.77 (s, 1H), 4.53-4.65 (m, 2H), 4.43-4.53 (m, 2H), 4.27-4.31 (m, 1H), 4.04-4.14 (br. s., 4H), 4.01 (s, 2H), 2.80-3.13 (m, 4H); MS m/z (M + H+) 414.3 |
| 25 | 2-[4-(1-{[4-(1H-Pyrrol-1-yl)phenyl]carbonyl}azetidin-3-yl)piperazin-1-yl]pyrimidine<br>$^1$H NMR (300 MHz, CD3OD) δ 8.32 (d, 2H), 7.68 (d, 2H), 7.53 (d, 2H), 7.20 (t, 2H), 6.65 (t, 1H), 6.23 (t, 2H), 4.51-4.72 (m, 2 H), 4.24-4.48 (m, 2H), 3.93-4.19 (m, 5H), 3.22-3.18 (m, 4H); LC/MS m/z (M + H+) 389.2 (calculated for C22H24N6O, 388.48) |
| 26 | 2-(4-{1-[(2-Fluorobiphenyl-4-yl)carbonyl]azetidin-3-yl}piperazin-1-yl)pyrimidine<br>$^1$H NMR (400 MHz, DMSO-d6) δ 8.45 (d, J = 8.0 Hz, 2H), 7.66 (d, J = 8.0 Hz, 1H), 7.57-7.62 (m, 3H), 7.49-7.57 (m, 2H), 7.47 (d, J = 7.3 Hz, 1H), 6.77 (t, J = 4.6 Hz, 1H), 4.58-4.73 (m, 2H), 4.34 (br. s., 2H), 4.01-3.83 (br. s., 5H), 2.89-3.35 (m, 4H); MS m/z (M + H+) 418.3 |
| 27 | N-(4-{[3-(4-Pyridin-2-ylpiperazin-1-yl)azetidin-1-yl]carbonyl}phenyl)cyclohexanecarboxamide<br>$^1$H NMR (400 MHz, DMSO-d6) δ 10.08 (s, 1H), 8.09-8.20 (m, 1 H), 7.69-7.75 (m, 3H), 7.64-7.69 (m, 1H), 7.61 (d, J = 8.8 Hz, 3 H), 6.98-7.06 (m, 1H), 6.75-6.81 (m, 1H), 4.57-4.66 (m, 2H), 4.49-4.57 (m, 2H), 4.04-4.13 (m, 1H), 3.4-2.8 (br. s., 8H), 2.29-2.40 (m, 1H), 1.78 (br. s., 4H), 1.61-1.69 (m, 1H), 1.34-1.46 (m, 2H), 1.12-1.34 (m, 3H); MS m/z (M + H+) 448.3 |
| 28 | N,N-Dimethyl-4-{[3-(4-pyrimidin-2-ylpiperazin-1-yl)azetidin-1-yl]carbonyl}aniline<br>$^1$H NMR (300 MHz, CD3OD) δ 8.44 (d, J = 4.9 Hz, 2H), 7.60 (d, J = 9.0 Hz, 2H), 6.72-6.88 (m, 3H), 4.35-4.82 (m, 4H), 3.95-4.29 (m, 5H), 3.34-3.47 (m, 4H), 3.06 (s, 6H); LC/MS m/z (M + H+) 367.2 (calculated for C20H26N6O, 366.47) |
| 29 | 1-Pyridin-2-yl-4-{1-[3-(5,5,8,8-tetramethyl-5,6,7,8-tetrahydronaphth-2-yl)propanoyl]azetidin-3-yl}piperazine<br>$^1$H NMR (300 MHz, CD3CN) δ 8.01 (d, J = 4.9 Hz, 1H), 7.89 (ddd, J = 1.9, 7.2, 9.0 Hz, 1H), 7.05-7.21 (m, 3H), 6.80-6.96 (m, 2H), 4.32 (dd, 1H), 3.96-4.24 (m, 3H), 3.87 (t, J = 5.1 Hz, 4H), 3.65-3.81 (m, 1H), 3.13 (m, 4H), 2.66 (d, J = 8.3 Hz, 2H), 2.27 (d, J = 8.3 Hz, 2H), 1.58 (s, 4H), 1.15 (d, 12H); LC/MS m/z (M + H+) 461.4 (calculated for C29H40N4O, 460.67) |
| 30 | 1-{1-[(4-Benzylphenyl)carbonyl]azetidin-3-yl}-4-pyridin-2-ylpiperazine<br>$^1$H NMR (400 MHz, DMSO-d6) δ = 8.12-8.17 (m, 1H), 7.63-7.70 (m, 1H), 7.59 (d, J = 8.1 Hz, 2H), 7.35 (d, J = 8.1 Hz, 2H), 7.30 (d, J = 7.1 Hz, 2H), 7.27 (s, 2H), 7.17-7.23 (m, 1H), 6.99-7.06 (m, 1H), 6.75-6.81 (m, 1H), 4.54-4.63 (m, 2H), 4.43-4.53 (m, 2 H), 4.19-4.34 (m, 4H), 4.03-4.12 (m, 1H), 4.01 (s, 2H), 3.01-3.19 (m, 4H); MS m/z (M + H+) 413.3 |

-continued

| Cmpd No. | Compound Name<br>Measured Physical Properties of Prepared Sample |
|---|---|
| 31 | 1-Propyl-5-{[3-(4-pyridin-2-ylpiperazin-1-yl)azetidin-1-yl]carbonyl}-1H-indole<br>$^1$H NMR (300 MHz, CD3CN) δ 8.02 (d, J = 4.9 Hz, 1H), 7.72-7.88 (m, 2H), 7.35 (s, 2H), 7.22 (d, J = 3.0 Hz, 1H), 7.02 (d, J = 9.0 Hz, 1H), 6.85 (t, J = 6.2 Hz, 1H), 6.45 (d, J = 3.4 Hz, 1H), 4.16-4.59 (m, 4H), 4.04 (t, J = 7.0 Hz, 2H), 3.71-3.92 (m, 5H), 3.13 (m, 4H), 1.61-1.81 (m, 2H), 0.78 (t, 3H); LC/MS m/z (M + H+) 404.2 (calculated for C24H29N5O, 403.53) |
| 32 | 2-(4-{1-[(4-Cyclohexylphenyl)carbonyl]azetidin-3-yl}piperazin-1-yl)-1,3,5-triazine<br>$^1$H NMR (300 MHz, CD3OD) δ 8.64 (s, 2H), 7.60 (d, 2H), 7.35 (d, 2H), 4.25-4.69 (m, 4H), 4.07-4.25 (m, 4H), 3.97 (m, 1H), 3.09-3.26 (m, 4H), 2.59 (m, 1H), 1.69-1.97 (m, 5H), 1.17-1.60 (m, 5H); LC/MS m/z (M + H+) 407.3 (calculated for C23H30N6O, 406.54) |
| 33 | 3-(4-{1-[(4-Cyclohexylphenyl)carbonyl]azetidin-3-yl}piperazin-1-yl)-1,2-benzisoxazole<br>$^1$H NMR (300 MHz, CD3OD) δ 7.89 (d, 1H), 7.49-7.66 (m, 4H), 7.29-7.41 (m, 3H), 4.29-4.76 (m, 4H), 4.16 (m, 1H), 3.74-3.91 (m, 4H), 3.36-3.50 (m, 4H), 2.59 (m, 1H), 1.69-1.94 (m, 5H), 1.21-1.58 (m, 5H); LC/MS m/z (M + H+) 445.2 (calculated for C27H32N4O2, 444.58) |
| 34 | 1-{1-[(4-Cyclohexylphenyl)carbonyl]azetidin-3-yl}-4-[5-(trifluoromethyl)-1,3,4-thiadiazol-2-yl]piperazine<br>$^1$H NMR (300 MHz, CD3OD) δ 7.59 (d, 2H), 7.34 (d, 2H), 4.15-4.66 (m, 4H), 3.75-3.95 (m, 5H), 2.97-3.19 (m, 4H), 2.58 (m, 1 H), 1.68-1.95 (m, 5H), 1.19-1.58 (m, 5H); LC/MS m/z (M + H+) 480.1 (calculated for C23H28F3N5OS, 479.57) |
| 35 | 1-{1-[(4-Butylphenyl)carbonyl]azetidin-3-yl}-4-pyridin-2-ylpiperazine<br>$^1$H NMR (300 MHz, CD3CN) δ 8.15 (d, J = 4.9 Hz, 1H), 7.95 (ddd, J = 1.9, 7.2, 9.0 Hz, 1H), 7.54 (d, J = 8.3 Hz, 2H), 7.30 (d, J = 7.9 Hz, 2H), 7.16 (d, J = 9.0 Hz, 1H), 6.98 (t, J = 6.6 Hz, 1H), 4.24-4.73 (m, 4H), 3.81-4.06 (m, 5H), 3.25 (d, J = 3.8 Hz, 4H), 2.68 (t, 2H), 1.51-1.71 (m, 2H), 1.22-1.47 (m, 2H), 0.79-1.05 (m, 3H); LC/MS m/z (M + H+) 379.4 (calculated for C23H30N4O, 378.52) |
| 36 | 1-[1-(Biphenyl-4-ylcarbonyl)azetidin-3-yl]-4-(1,3-thiazol-2-yl)piperazine<br>$^1$H NMR (300 MHz, CD3OD) δ 7.76 (s, 4H), 7.60-7.71 (m, 2H), 7.33-7.53 (m, 3H), 7.29 (d, 1H), 6.99 (d, 1H), 4.59-4.71 (m, 1 H), 4.37-4.59 (m, 2H), 4.23-4.36 (m, 1H), 3.88 (m, 1H), 3.68-3.82 (m, 4H), 2.98-3.20 (m, 4H); LC/MS m/z (M + H+) 405.1 (calculated for C23H24N4OS, 404.54) |
| 37 | N,N-Diethyl-4-{[3-(4-pyridin-2-ylpiperazin-1-yl)azetidin-1-yl]carbonyl}aniline<br>$^1$H NMR (300 MHz, CD3OD) δ 7.95-8.13 (m, 2H), 7.63-7.74 (d, 2H), 7.35 (d, 1H), 6.98-7.16 (m, 3H), 4.24-4.74 (m, 4H), 3.84-4.04 (m, 5H), 3.47-3.62 (q, 4H), 3.18 (m, 4H), 1.16 (t, 6H); LC/MS m/z (M + H+) 394.4 (calculated for C23H31N5O, 393.54) |
| 38 | 2-(4-{1-[(3-Iodo-4-methoxyphenyl)carbonyl]azetidin-3-yl}piperazin-1-yl)pyrimidine<br>$^1$H NMR (400 MHz, DMSO-d6) δ 8.45 (d, J = 4.9 Hz, 2H), 8.02 (d, J = 2.0 Hz, 1H), 7.68 (dd, J = 2.2, 8.6 Hz, 1H), 7.08 (d, J = 8.6 Hz, 1H), 6.77 (t, J = 4.8 Hz, 1H), 4.57-4.64 (m, 2H), 4.52 (br. s., 2H), 4.23-4.31 (m, 5H), 4.02-4.09 (m, 4H); MS m/z (M + H+) 480.2 |
| 39 | 1-(1-{[5-(4-Chlorophenyl)-1-(2,4-dichlorophenyl)-4-methyl-1H-pyrazol-3-yl]carbonyl}azetidin-3-yl)-4-pyridin-2-ylpiperazine<br>$^1$H NMR (300 MHz, CD3CN) δ 8.02 (d, J = 6.0 Hz, 1H), 7.76 (td, 1H), 7.50 (t, 1H), 7.23-7.37 (m, 4H), 7.02-7.13 (m, 2H), 6.97 (d, J = 9.0 Hz, 1H), 6.81 (t, J = 6.2 Hz, 1H), 4.61 (d, J = 6.4 Hz, 2 H), 4.12-4.32 (m, 2H), 3.80 (t, J = 5.3 Hz, 5H), 3.08 (m, 4H), 2.16 (s, 3H); LC/MS m/z (M + H+) 581.1/583.1 (calculated for C29H27Cl3N6O, 581.94) |
| 40 | N-(Cyclohexylmethyl)-N-methyl-4-{3-oxo-3-[3-(4-pyridin-2-ylpiperazin-1-yl)azetidin-1-yl]propyl}aniline<br>$^1$H NMR (300 MHz, CD3CN) δ 8.15 (d, J = 4.9 Hz, 1H), 7.99 (ddd, J = 1.9, 7.2, 9.0 Hz, 1H), 7.33-7.45 (m, 4H), 7.21 (d, J = 9.0 Hz, 1H), 7.01 (t, J = 6.6 Hz, 1H), 4.48 (dd, J = 4.7, 9.6 Hz, 1H), 4.33 (t, 1H), 4.08-4.26 (m, 2H), 3.79-4.07 (m, 5H), 3.19-3.43 (m, 6H), 3.15 (s, 3H), 2.91 (t, J = 7.3 Hz, 2H), 2.43 (t, J = 7.7 Hz, 2 H), 1.48-1.75 (m, 5H), 1.27-1.47 (m, 1H), 0.85-1.22 (m, 5H); LC/MS m/z (M + H+) 476.4 |

| Cmpd No. | Compound Name<br>Measured Physical Properties of Prepared Sample |
|---|---|
| 41 | 1-Pyridin-2-yl-4-{1-[(2E)-3-{4-[(trifluoromethyl)sulfanyl]phenyl}prop-2-enoyl]azetidin-3-yl}piperazine<br>$^1$H NMR (300 MHz, CD3CN) δ 8.15 (d, J = 4.9 Hz, 1H), 7.96 (ddd, J = 1.9, 7.2, 9.0 Hz, 1H), 7.73 (s, 4H), 7.56 (d, J = 15.8 Hz, 1H), 7.18 (d, J = 9.4 Hz, 1H), 6.99 (t, J = 6.6 Hz, 1H), 6.71 (d, J = 15.8 Hz, 1H), 4.52-4.70 (m, 2H), 4.20-4.39 (m, 2H), 3.88-4.07 (m, 5H), 3.16-3.37 (m, 4H); LC/MS m/z (M + H+) 449.2 (calculated for C22H23F3N4OS, 448.51) |
| 42 | 1-[1-(Biphenyl-4-ylcarbonyl)azetidin-3-yl]-4-pyridin-2-ylpiperazine<br>MS m/z (M + H+) 399.3 |
| 43 | 2-(4-{1-[(4-Chloro-3-iodophenyl)carbonyl]azetidin-3-yl}piperazin-1-yl)pyrimidine<br>MS m/z (M + H+) 484.1 |
| 44 | 1-(1-{[4-(1,1-Dimethylpropyl)phenyl]carbonyl}azetidin-3-yl)-4-pyridin-2-ylpiperazine<br>LC/MS m/z (M + H+) 393.3 |
| 45 | 1-{1-[(4-Phenoxyphenyl)carbonyl]azetidin-3-yl}-4-pyridin-2-ylpiperazine<br>LC/MS m/z (M + H+) 415.2 |
| 46 | 2-[4-(1-{[4-(1H-Pyrazol-1-yl)phenyl]carbonyl}azetidin-3-yl)piperazin-1-yl]pyrimidine<br>LC/MS m/z (M + H+) 390.1 |
| 47 | 1-{1-[(3-Phenoxyphenyl)carbonyl]azetidin-3-yl}-4-pyridin-2-ylpiperazine<br>LC/MS m/z (M + H+) 415.2 |
| 48 | 2-(4-{1-[(3-Iodo-4-methylphenyl)carbonyl]azetidin-3-yl}piperazin-1-yl)pyrimidine<br>MS m/z (M + H+) 464.2 |
| 49 | 2-Phenyl-5-{[3-(4-pyridin-2-ylpiperazin-1-yl)azetidin-1-yl]carbonyl}-1H-benzimidazole<br>LC/MS m/z (M + H+) 439.3 |
| 50 | 2-(4-{1-[(4-Iodo-3-methylphenyl)carbonyl]azetidin-3-yl}piperazin-1-yl)pyrimidine<br>MS m/z (M + H+) 464.2 |
| 51 | 2-(4-{1-[3-(4-Iodophenyl)propanoyl]azetidin-3-yl}piperazin-1-yl)pyrimidine<br>LC/MS m/z (M + H+) 478.0 |
| 52 | 1-{1-[(4'-Fluorobiphenyl-3-yl)carbonyl]azetidin-3-yl}-4-pyridin-2-ylpiperazine<br>LC/MS m/z (M + H+) 417.3 |
| 53 | 2-(4-{1-[(4-Iodophenyl)carbonyl]azetidin-3-yl}piperazin-1-yl)pyrimidine<br>MS m/z (M + H+) 450.1 |
| 54 | 1-{1-[(4-Pentylcyclohexyl)carbonyl]azetidin-3-yl}-4-pyridin-2-ylpiperazine<br>LC/MS m/z (M + H+) 399.3 |
| 55 | 1-{1-[3-(4-tert-Butylphenyl)propanoyl]azetidin-3-yl}-4-pyridin-2-ylpiperazine<br>LC/MS m/z (M + H+) 407.3 |
| 56 | 1-(5-Chloropyridin-2-yl)-4-{1-[(4-cyclohexylphenyl)carbonyl]azetidin-3-yl}piperazine<br>LC/MS m/z (M + H+) 439.2 |
| 57 | 1-{1-[(6-Methoxynaphth-2-yl)carbonyl]azetidin-3-yl}-4-pyridin-2-ylpiperazine<br>LC/MS m/z (M + H+) 403.2 |
| 58 | 1-(1-{[2-(Benzyloxy)phenyl]carbonyl}azetidin-3-yl)-4-pyridin-2-ylpiperazine<br>LC/MS m/z (M + H+) 429.3 |
| 59 | 2-{[3-(4-Pyridin-2-ylpiperazin-1-yl)azetidin-1-yl]carbonyl}-9H-fluoren-9-one<br>LC/MS m/z (M + H+) 425.2 |
| 60 | 1-{1-[(2-Fluorobiphenyl-4-yl)carbonyl]azetidin-3-yl}-4-pyridin-2-ylpiperazine<br>MS m/z (M + H+) 417.3 |
| 61 | 1-(1-{[4-Phenyl-5-(trifluoromethyl)thiophen-2-yl]carbonyl}azetidin-3-yl)-4-pyridin-2-ylpiperazine<br>LC/MS m/z (M + H+) 473.2 |
| 62 | 5-(Benzyloxy)-2-{[3-(4-pyridin-2-ylpiperazin-1-yl)azetidin-1-yl]carbonyl}-1H-indole<br>LC/MS m/z (M + H+) 468.3 |
| 63 | 1-Cyclohexyl-5-{(1E)-3-oxo-3-[3-(4-pyridin-2-ylpiperazin-1-yl)azetidin-1-yl]prop-1-en-1-yl}-2,3-dihydro-1H-indole<br>LC/MS m/z (M + H+) 472.4 |

| Cmpd No. | Compound Name<br>Measured Physical Properties of Prepared Sample |
|---|---|
| 64 | 2-(4-{1-[3-(3-Iodophenyl)propanoyl]azetidin-3-yl}piperazin-1-yl)pyrimidine<br>MS m/z (M + H+) 478.2 |
| 65 | 1-(1-{(2E)-3-[4-(1-Methylethyl)phenyl]prop-2-enoyl}azetidin-3-yl)-4-pyridin-2-ylpiperazine<br>LC/MS m/z (M + H+) 391.4 |
| 66 | 2-(4-{1-[(4-Cyclohexylphenyl)carbonyl]azetidin-3-yl}piperazin-1-yl)-1,3-benzoxazole<br>LC/MS m/z (M + H+) 445.4 |
| 67 | 1-[1-(Biphenyl-3-ylcarbonyl)azetidin-3-yl]-4-pyridin-2-ylpiperazine<br>LC/MS m/z (M + H+) 399.3 |
| 68 | 1-(1-{[5-(4-Chlorophenyl)-1-(3,4-dichlorophenyl)-1H-pyrazol-3-yl]carbonyl}azetidin-3-yl)-4-pyridin-2-ylpiperazine<br>LC/MS m/z (M + H+) 567.2/569.1 |
| 69 | 2-{4-[1-(Biphenyl-4-ylcarbonyl)azetidin-3-yl]-4-oxidopiperazin-1-yl}pyrimidine<br>MS m/z (M + H+) 416.2 |
| 70 | 1-{1-[(1,5-Diphenyl-1H-pyrazol-3-yl)carbonyl]azetidin-3-yl}-4-pyridin-2-ylpiperazine<br>LC/MS m/z (M + H+) 465.3 |
| 71 | 2-[4-(1-{[4-(1H-Imidazol-1-yl)phenyl]carbonyl}azetidin-3-yl)piperazin-1-yl]pyrimidine<br>LC/MS m/z (M + H+) 390.1 |
| 72 | 4-[5-(4-Chlorophenyl)-3-{[3-(4-pyridin-2-ylpiperazin-1-yl)azetidin-1-yl]carbonyl}-1H-pyrazol-1-yl]benzenesulfonamide<br>LC/MS m/z (M + H+) 578.3/580.2 |
| 73 | 1-{1-[(2E)-3-Biphenyl-4-ylprop-2-enoyl]azetidin-3-yl}-4-pyridin-2-ylpiperazine<br>LC/MS m/z (M + H+) 425.2 |
| 74 | Phenyl(4-{[3-(4-pyridin-2-ylpiperazin-1-yl)azetidin-1-yl]carbonyl}phenyl)methanone<br>LC/MS m/z (M + H+) 427.4 |
| 75 | 1-(3-Chloropyridin-2-yl)-4-{1-[(4-cyclohexylphenyl)carbonyl]azetidin-3-yl}piperazine<br>LC/MS m/z (M + H+) 439.2 |
| 75 | 1-{1-[(4-Cyclohexylphenyl)carbonyl]azetidin-3-yl}-4-(4-methylpyridin-2-yl)piperazine<br>LC/MS m/z (M + H+) 419.2 |
| 76 | 2-(4-{[3-(4-Pyridin-2-ylpiperazin-1-yl)azetidin-1-yl]carbonyl}phenyl)-1H-isoindole-1,3(2H)-dione<br>LC/MS m/z (M + H+) 468.3 |
| 77 | 1-(5-Bromopyridin-2-yl)-4-{1-[(4-cyclohexylphenyl)carbonyl]azetidin-3-yl}piperazine<br>LC/MS m/z (M + H+) 483.1/485.2 |
| 78 | 1-{1-[(4-tert-Butylcyclohexyl)carbonyl]azetidin-3-yl}-4-pyridin-2-ylpiperazine<br>LC/MS m/z (M + H+) 385.4 |
| 80 | 1-Pyridin-2-yl-4-[1-({5-[3-(trifluoromethyl)phenyl]furan-2-yl}carbonyl)azetidin-3-yl]piperazine<br>LC/MS m/z (M + H+) 457.4 |
| 81 | 2-(3-{[3-(4-Pyridin-2-ylpiperazin-1-yl)azetidin-1-yl]carbonyl}phenyl)-2,3-dihydro-1H-isoindole<br>LC/MS m/z (M + H+) 440.2 |
| 82 | 1-{1-[(4-Cyclohexylphenyl)carbonyl]azetidin-3-yl}-4-[3-(trifluoromethyl)pyridin-2-yl]piperazine<br>LC/MS m/z (M + H+) 473.2 |
| 84 | 1-(1-{[5-(4-Methylphenyl)furan-2-yl]carbonyl}azetidin-3-yl)-4-pyridin-2-ylpiperazine<br>LC/MS m/z (M + H+) 403.4 |
| 85 | 1-[1-(Biphenyl-4-ylcarbonyl)azetidin-3-yl]-4-(5-bromopyridin-2-yl)piperazine<br>LC/MS m/z (M + H+) 477.1/479.1 |
| 86 | Phenyl(3-{[3-(4-pyridin-2-ylpiperazin-1-yl)azetidin-1-yl]carbonyl}phenyl)methanone<br>LC/MS m/z (M + H+) 427.4 |
| 87 | 1-Pyridin-2-yl-4-[1-(4-pyrrolidin-1-yl-phenyl)-azetidin-3-yl]-[1,4]diazepane<br>MS m/z (M + H+) 407.2 |

| Cmpd No. | Compound Name<br>Measured Physical Properties of Prepared Sample |
|---|---|
| 88 | 1-[1-(Biphenyl-4-ylacetyl)azetidin-3-yl]-4-pyridin-2-ylpiperazine<br>LC/MS m/z (M + H+) 413.3 |
| 89 | 1-[1-(Biphenyl-4-ylcarbonyl)azetidin-3-yl]-4-(2-methoxyphenyl)piperazine<br>LC/MS m/z (M + H+) 428.3 |
| 90 | 2-{4-[1-(Biphenyl-4-ylcarbonyl)azetidin-3-yl]piperazin-1-yl}-1,3-benzoxazole<br>LC/MS m/z (M + H+) 439.2 |
| 91 | 1-[1-(Biphenyl-4-ylcarbonyl)azetidin-3-yl]-4-[2-(methylsulfanyl)phenyl]piperazine<br>LC/MS m/z (M + H+) 444.1 |
| 92 | 1-(1-{[5-(4-Methoxyphenyl)furan-2-yl]carbonyl}azetidin-3-yl)-4-pyridin-2-ylpiperazine<br>LC/MS m/z (M + H+) 419.2 |
| 93 | 6-(4-{1-[(4-Cyclohexylphenyl)carbonyl]azetidin-3-yl}piperazin-1-yl)pyridine-3-carbonitrile<br>LC/MS m/z (M + H+) 430.2 |
| 94 | 2-(4-{1-[(4-Nitrophenyl)carbonyl]azetidin-3-yl}piperazin-1-yl)pyrimidine<br>MS m/z (M + H+) 369.2 |
| 95 | 1-Pyridin-2-yl-4-(1-{(2E)-3-[3-(trifluoromethyl)phenyl]prop-2-enoyl}azetidin-3-yl)piperazine<br>LC/MS m/z (M + H+) 417.2 |
| 96 | 1-[1-(9H-Fluoren-1-ylcarbonyl)azetidin-3-yl]-4-pyridin-2-ylpiperazine<br>LC/MS m/z (M + H+) 411.3 |
| 97 | 6-{[3-(4-Pyridin-2-ylpiperazin-1-yl)azetidin-1-yl]carbonyl}-1,2,3,4-tetrahydroquinoline<br>LC/MS m/z (M + H+) 378.3 |
| 98 | 1-{1-[(4-Cyclohexylphenyl)carbonyl]azetidin-3-yl}-4-(3-iodopyridin-2-yl)piperazine<br>MS m/z (M + H+) 531.2 |
| 99 | 1-{1-[(5-Phenylfuran-2-yl)carbonyl]azetidin-3-yl}-4-pyridin-2-ylpiperazine<br>LC/MS m/z (M + H+) 398.2 |
| 100 | 1-{1-[(4-Cyclohexylphenyl)carbonyl]azetidin-3-yl}-4-(3-methylpyridin-2-yl)piperazineLC/MS m/z (M + H+) 419.2 |
| 101 | 1-[1-(Biphenyl-4-ylcarbonyl)azetidin-3-yl]-4-[3-(trifluoromethyl)pyridin-2-yl]piperazine<br>LC/MS m/z (M + H+) 467.3 |
| 102 | 1-[1-(Biphenyl-4-ylcarbonyl)azetidin-3-yl]-4-(4-methylpyridin-2-yl)piperazine<br>LC/MS m/z (M + H+) 413.3 |
| 103 | 1-[1-(2,3-Diphenylpropanoyl)azetidin-3-yl]-4-pyridin-2-ylpiperazine<br>LC/MS m/z (M + H+) 427.4 |
| 104 | 2-(4-{1-[(4-Cyclohexylphenyl)carbonyl]azetidin-3-yl}piperazin-1-yl)-1,3-benzothiazole<br>LC/MS m/z (M + H+) 461.2 |
| 105 | 1-[1-(Biphenyl-4-ylcarbonyl)azetidin-3-yl]-4-(2-nitrophenyl)piperazine<br>LC/MS m/z (M + H+) 443.2 |
| 106 | 2-{4-[1-(Biphenyl-4-ylcarbonyl)azetidin-3-yl]piperazin-1-yl}-1,3-benzothiazole<br>LC/MS m/z (M + H+) 455.1 |
| 107 | 1-{1-[(1-Phenyl-1H-pyrazol-4-yl)carbonyl]azetidin-3-yl}-4-pyridin-2-ylpiperazine<br>MS m/z (M + H+) 389.3 |
| 108 | 1-(1-{[2-Phenyl-5-(trifluoromethyl)-1,3-oxazol-4-yl]carbonyl}azetidin-3-yl)-4-pyridin-2-ylpiperazine<br>LC/MS m/z (M + H+) 458.3 |
| 109 | 1-{1-[(3-Phenoxyphenyl)acetyl]azetidin-3-yl}-4-pyridin-2-ylpiperazine<br>LC/MS m/z (M + H+) 429.3 |
| 110 | 1-[1-(4-Benzyl-phenyl)-azetidin-3-yl]-4-pyrimidin-2-yl-[1,4]diazepane<br>MS m/z (M + H+) 428.2 |
| 111 | 2-[4-(1-{[4-(Benzyloxy)phenyl]carbonyl}azetidin-3-yl)piperazin-1-yl]pyrimidine<br>$^1$H NMR (400 MHz, DMSO-d6) δ = 8.44 (d, J = 4.9 Hz, 2H), 7.64 (d, J = 8.8 Hz, 2H), 7.44-7.49 (m, 2H), 7.41 (t, J = 7.2 Hz, 2H), 7.32-7.38 (m, 1H), 7.10 (d, J = 8.8 Hz, 2H), 6.76 (s, 1H), 5.19 (s, 2H), 4.54-4.64 (m, 2H), 4.45-4.54 (m, 2H), 4.19-4.29 (m, 1H), 3.93-4.10 (m, 4H), 2.99 (br. s., 4H); MS m/z (M + H+) 430.3 |

| Cmpd No. | Compound Name<br>Measured Physical Properties of Prepared Sample |
|---|---|
| 112 | 1-(1-{[4-(Benzyloxy)phenyl]carbonyl}azetidin-3-yl)-4-pyridin-2-ylpiperazine<br>$^1$H NMR (300 MHz, CD3CN) δ 8.01 (d, J = 4.5 Hz, 1H), 7.80 (ddd, J = 1.9, 7.2, 9.0 Hz, 1H), 7.44-7.56 (m, 2H), 7.20-7.43 (m, 5H), 7.02 (d, J = 9.0 Hz, 1H), 6.95 (d, J = 7.9 Hz, 2H), 6.85 (t, J = 6.4 Hz, 1H), 5.06 (s, 2H), 4.11-4.58 (m, 4H), 3.72-3.91 (m, 5 H), 3.08 (m, 4H); LC/MS m/z (M + H+) 429.3 (calculated for C26H28N4O2, 428.54) |
| 113 | 1-{1-[(2E)-3-(3-Ethoxyphenyl)prop-2-enoyl]azetidin-3-yl}-4-pyridin-2-ylpiperazine<br>LC/MS m/z (M + H+) 393.3 |
| 114 | 1-{1-[(4-Benzylphenyl)carbonyl]azetidin-3-yl}-4-(3-iodopyridin-2-yl)piperazine<br>MS m/z (M + H+) 539.2 |
| 115 | 6-{[3-(4-Pyridin-2-ylpiperazin-1-yl)azetidin-1-yl]carbonyl}quinoline<br>LC/MS m/z (M + H+) 374.2 |
| 116 | 2-{[3-(4-Pyridin-2-ylpiperazin-1-yl)azetidin-1-yl]carbonyl}quinoline<br>LC/MS m/z (M + H+) 374.2 |
| 117 | 1-{1-[(3-Methyl-1-benzofuran-2-yl)carbonyl]azetidin-3-yl}-4-pyridin-2-ylpiperazine<br>LC/MS m/z (M + H+) 377.2 |
| 118 | 1-(1-{[4-(Benzyloxy)phenyl]carbonyl}azetidin-3-yl)-4-(3-iodopyridin-2-yl)piperazineMS m/z (M + H+) 555.2 |
| 119 | 1-{1-[(5-Butylpyridin-2-yl)carbonyl]azetidin-3-yl}-4-pyridin-2-ylpiperazine<br>LC/MS m/z (M + H+) 380.2 |
| 120 | 4-(Benzyloxy)-2-{[3-(4-pyridin-2-ylpiperazin-1-yl)azetidin-1-yl]carbonyl}-1H-indole<br>LC/MS m/z (M + H+) 468.3 |
| 121 | 5-{[3-(4-Pyridin-2-ylpiperazin-1-yl)azetidin-1-yl]carbonyl}-1H-indoleLC/MS m/z (M + H+) 362.3 |
| 122 | tert-Butyl 4-(4-{[3-(4-pyridin-2-ylpiperazin-1-yl)azetidin-1-yl]carbonyl}phenyl)piperidine-1-carboxylate<br>LC/MS m/z (M + H+) 506.4 |
| 123 | 1-(1-{[5-(Phenylethynyl)furan-2-yl]carbonyl}azetidin-3-yl)-4-pyridin-2-ylpiperazine<br>LC/MS m/z (M + H+) 413.3 |
| 124 | 4-{4-[3-(4-Pyridin-2-yl-[1,4]diazepan-1-yl)-azetidin-1-yl]-phenoxy}-piperidine-1-carboxylic acid tert-butyl ester<br>MS m/z (M + H+) 522.3 |
| 125 | 1-Pyridin-2-yl-4-[1-(1,2,3,4-tetrahydronaphth-2-ylcarbonyl)azetidin-3-yl]piperazine<br>LC/MS m/z (M + H+) 377.2 |
| 126 | 1-{1-[(2R)-2-(2-Fluorobiphenyl-4-yl)propanoyl]azetidin-3-yl}-4-pyridin-2-ylpiperazine<br>MS m/z (M + H+) 445.3 |
| 128 | 1-{1-[(4-Pentylbicyclo[2.2.2]oct-1-yl)carbonyl]azetidin-3-yl}-4-pyridin-2-ylpiperazine<br>LC/MS m/z (M + H+) 425.4 |
| 129 | 1-(1-{[5-(3,5-Dichlorophenoxy)furan-2-yl]carbonyl}azetidin-3-yl)-4-pyridin-2-ylpiperazine<br>LC/MS m/z (M + H+) 473.1/475.2 |
| 130 | 3-{[3-(4-Pyridin-2-ylpiperazin-1-yl)azetidin-1-yl]carbonyl}-9H-xanthen-9-one<br>MS m/z (M + H+) 441.3 |
| 131 | 2-(3-{4-[(4-Benzylphenyl)carbonyl]piperazin-1-yl}azetidin-1-yl)pyrimidine<br>MS m/z (M + H+) 414.2 |
| 132 | 1-Phenyl-6-{[3-(4-phenylpiperazin-1-yl)azetidin-1-yl]carbonyl}-1,2,3,4-tetrahydroquinoline<br>LC/MS m/z (M + H+) 453.2 |
| 133 | 6-[(3-{4-[4-(Trifluoromethyl)phenyl]piperazin-1-yl}azetidin-1-yl)carbonyl]-1,2,3,4-tetrahydroquinoline<br>LC/MS m/z (M + H+) 445.2 |
| 134 | 1-[4-(Trifluoromethyl)phenyl]-6-[(3-{4-[4-(trifluoromethyl)phenyl]piperazin-1-yl}azetidin-1-yl)carbonyl]-1,2,3,4-tetrahydroquinoline<br>LC/MS m/z (M + H+) 589.0 |
| 135 | 1-[3-(Trifluoromethyl)phenyl]-6-[(3-{4-[3-(trifluoromethyl)phenyl]piperazin-1-yl}azetidin-1-yl)carbonyl]-1,2,3,4-tetrahydroquinoline<br>LC/MS m/z (M + H+) 489.0 |

EXAMPLE 2

Compound #139

(6-Trifluoromethyl-benzo[b]thien-2-yl)-[3-(4-pyrimidin-2-yl-piperazin-1-yl)-azetidin-1-yl]-methanone

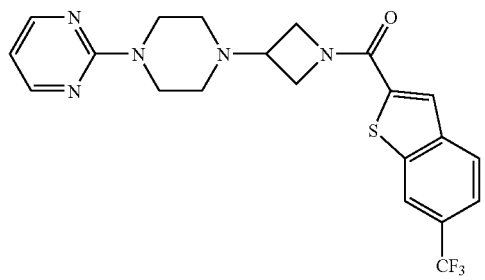 [SMILES: O=C(c1cc2ccc(C(F)(F)F)cc2s1)N1CC(N2CCN(c3ncccn3)CC2)C1]

STEP A: 4-(2,2,2-Trifluoro-acetyl)-piperazine-1-carboxylic acid tert-butyl ester To a solution of piperazine-1-carboxylic acid tert-butyl ester (10 g, 53.69 mmol) and pyridine (8.7 mL, 107.57 mmol) in $CH_2Cl_2$ (100 mL) was added dropwise $(CF_3CO)_2O$ (10.5 mL, 75.54 mmol) at 0° C. The resulting mixture was stirred at 0° C. for 2 h. 2N HCl (60 mL) was then added. The organic layer was dried over $MgSO_4$, filtered, and then concentrated. The resulting residue, the title compound, was used in the next reaction without further purification. MS m/z (MH$^+$-Boc) 183.1, (MH$^+$—$C_4H_9$) 227.1; $^1$H NMR (300 MHz, $CDCl_3$): δ 3.45-3.7 (m, 8H), 1.5 (s, 9H).

STEP B: 2,2,2-Trifluoro-1-piperazin-1-yl-ethanone

To a solution of compound 4-(2,2,2-trifluoro-acetyl)-piperazine-1-carboxylic acid tent-butyl ester (15.15 g, 53.69 mmol) in $CH_2Cl_2$ (60 mL) was added trifluoroacetic acid (18 mL) at room temperature. The resulting mixture was stirred at room temperature for 18 h. The solvent was removed by evaporation. Diethyl ether (100 mL) was added to the residue. The white solid was collected by filtration, washed with diethyl ether, and dried under vacuum. The resulting residue, the title compound, was used in the next reaction without further purification. MS m/z (M+H$^+$) 183.1.

STEP C: 1-[4-(1-Benzhydryl-azetidin-3-yl)-piperazin-1-yl]-2,2,2-trifluoro-ethanone To a solution of 2,2,2-trifluoro-1-piperazin-1-yl-ethanone (6 g, 32.94 mmol) and 1-benzhydrylazetidin-3-yl methanesulfonate (12.5 g, 39.38 mmol) in $CH_3CN$ (60 mL) was added DIPEA (12 mL, 68.89 mmol) at room temperature. The resulting mixture was refluxed for 2 h. The solvent was removed by evaporation and the residue was partitioned between $CH_2Cl_2$ and aq $NaHCO_3$. The organic layer was washed with aq $NaHCO_3$ (2×) and then extracted with 1N HCl (2×). The aqueous layer was cooled and then the pH adjusted with 1N NaOH until basic (pH=10). The resulting mixture was extracted with $CH_2Cl_2$ (2×). The organic layer was dried over $MgSO_4$ and concentrated. The title compound was purified by reverse phase chromatography. MS m/z (M+H$^+$) 404.2.

STEP D. 1-(4-Azetidin-3-yl-piperazin-1-yl)-2,2,2-trifluoro-ethanone

To a solution of 1-[4-(1-benzhydryl-azetidin-3-yl)-piperazin-1-yl]-2,2,2-trifluoro-ethanone (2.11 g, 5.23 mmol) in $CH_2Cl_2$ (60 mL) was added 1-chloroethyl chloroformate (2.0 mL, 18.35 mmol) at 0° C. under $N_2$. The resulting mixture was stirred at 0° C. for 90 min and then methanol (4 mL) was added. The resulting mixture was refluxed for 1 h. Upon cooling, diethyl ether (50 mL) was added to the mixture. The resulting solid was collected by filtration and dried to yield the title compound, which was used in the next reaction without further purification. MS m/z (M+H$^+$) 238.1.

STEP E: 6-(Trifluoromethyl)benzo[b]thiophene-2-carbonyl chloride

Oxalyl chloride (2.29 mmol, 0.20 mL) was added to a solution of 6-(trifluoromethyl)benzo[b]thiophene-2-carboxylic acid (2.03 mmol, 500 mg) $CH_2Cl_2$ (15 mL). DMF (15 μL) was added and the resulting mixture was stirred for 4 h at room temperature. The resulting solution was concentrated to yield 6-(trifluoromethyl)benzo[b]thiophene-2-carbonyl chloride, which was used in the next step without purification.

STEP F: 2,2,2-Trifluoro-1-(4-(1-(6-(trifluoromethyl)benzo[b]thiophene-2-carbonyl)azetidin-3-yl)piperazin-1-yl)ethanone A solution of 6-(trifluoromethyl)benzo[b]thiophene-2-carbonyl chloride (2.03 mmol, 537 mg) in $CH_2Cl_2$ (5 mL) was added to a solution of 1-(4-azetidin-3-yl-piperazin-1-yl)-2,2,2-trifluoro-ethanone (2.26 mmol, 700 mg) and TEA in $CH_2Cl_2$ (15 mL) at 0° C. The resulting mixture was allowed to warm to room temperature and was stirred for 2 h. Following workup and extraction, the residue was purified by flash column chromatography (silica gel, 3% methanol/$CH_2Cl_2$) to yield 2,2,2-trifluoro-1-(4-(1-(6-(trifluoromethyl)benzo[b]thiophene-2-carbonyl)azetidin-3-yl)piperazin-1-yl)ethanone.

STEP G: (3-(piperazin-1-yl)azetidin-1-yl)(6-(trifluoromethyl)benzo[b]thien-2-yl)methanone A solution of 2,2,2-trifluoro-1-(4-(1-(6-(trifluoromethyl)benzo[b]thiophene-2-carbonyl)azetidin-3-yl)piperazin-1-yl)ethanone (1.12 mmol, 520 mg) in 20 mL of methanol and TEA (2 mL) was stirred at room temperature for 3 days. The resulting mixture was concentrated to yield (3-(piperazin-1-yl)azetidin-1-yl)(6-(trifluoromethyl)benzo[b]thiophen-2-yl)methanone, which was used in the next step without purification.

STEP H: (3-(4-(Pyrimidin-2-yl)piperazin-1-yl)azetidin-1-yl)(6-(trifluoromethyl)benzo[b]thien-2-yl)methanone (Compound #139)

A mixture of (3-(piperazin-1-yl)azetidin-1-yl)(6-(trifluoromethyl)benzo[b]thiophen-2-yl)methanone (0.14 mmol, 50 mg), 2-bromopyrimidine (0.23 mmol, 37 mg), and $K_2CO_3$ (0.34 mmol, 47 mg) in THF (3 mL) and water (1.5 mL) was refluxed for 8 h. Following workup and extraction, the residue was purified by flash column chromatography (silica gel, 3% methanol/$CH_2Cl_2$) to yield (3-(4-(pyrimidin-2-yl)piperazin-1-yl)azetidin-1-yl)(6-(trifluoromethyl)benzo[b]thiophen-2-yl)methanone as a white solid.

$^1$H NMR (400 MHz, CDCl$_3$) δ 8.33 (d, J=4.6 Hz, 2H), 8.16 (s, 1H), 7.95 (d, J=8.3 Hz, 1H), 7.74 (s, 1H), 7.62 (d, J=8.3 Hz, 1H), 6.53 (t, J=4.6 Hz, 1H), 4.55-4.70 (m, 1H), 4.40-4.55 (m, 1H), 4.25-4.40 (m, 1H), 4.17 (m, 1H), 3.89 (m, 4H), 3.33 (m, 1H), 2.49 (m, 4H); LC/MS m/z (M+H$^+$) 448 (calculated for C$_{21}$H$_{20}$F$_3$N$_5$OS, 448.1).

EXAMPLE 3

In Vitro Assay

MGL Enzyme Activity Assay

All rate-based assays were performed in black 384-well polypropylene PCR microplates (Abgene) in a total volume of 30 μL. Substrate 4-methylumbelliferyl butyrate (4MU-B; Sigma) and either purified mutant MGL enzyme (mut-MGLL 11-313 L179S L186S) or purified wild type MGL (wt-MGLL 6H-11-313) were diluted separately into 20 mM PIPES buffer (pH=7.0), containing 150 mM NaCl and 0.001% Tween 20. Compounds of Formula (I) were pre-dispensed (50 mL) into the assay plate using a Cartesian Hummingbird (Genomic Solutions, Ann Arbor, Mich.) prior to adding 4MU-B (25 μL, of 1.2× solution to a final concentration of 10 μM) followed by enzyme (5 μL of a 6× solution to a final concentration of 5 nM) to initiate the reaction. Final compound concentrations ranged from 17 to 0.0003 μM. The fluorescence change due to 4MU-B cleavage was monitored with excitation and emission wavelengths of 335 and 440 nm, respectively, and a bandwidth of 10 nm (Safire$^2$, Tecan) at 37° C. for 5 min.

For determining percent inhibition, the initial rates were measured in the predetermined steady-state range (<10% substrate hydrolysis). The following equation was applied to determine percent inhibition:

% inhibition=[(maximum rate−inhibited rate)×100]/maximum rate.

The IC$_{50}$ values for compounds of Formula (I) were determined using Excel from a fit of the equation to the concentration-response plot of the fractional activity as a function of inhibitor concentration.

EXAMPLE 4

In Vitro Assay

MGL ThermoFluor® Assay

The ThermoFluor (TF) assay is a 384-well plate-based binding assay that measures thermal stability of proteins (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R., *J Biomol Screen* 2001, 6, 429-40; Matulis, D., Kranz, J. K., Salemme, F. R., and Todd, M. J., *Biochemistry* 2005, 44, 5258-66). The experiments were carried out using instruments available from Johnson & Johnson Pharmaceutical Research & Development, LLC. TF dye used in all experiments was 1,8-ANS (Invitrogen: A-47). Final TF assay conditions used for MGL studies were 0.07 mg/ml of purified mutant MGL (mut-MGLL 11-313 L179S L186S), 100 μM ANS, 200 mM NaCl and 0.001% Tween-20 in 50 mM PIPES (pH=7.0).

Screening compound plates contained 100% DMSO compound solutions at a single concentration. For follow-up concentration-response studies, compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For both single and multiple compound concentration-response experiments, the compound aliquots (50 mL) were robotically predispensed directly into black 384-well polypropylene PCR microplates (Abgene: TF-0384/k) using a Cartesian Hummingbird liquid handler (Genomic Solutions, Ann Arbor, Mich.). Following compound dispense, protein and dye solutions were added to achieve the final assay volume of 3 μL. The assay solutions were overlayed with 1 μL of silicone oil (Fluka, type DC 200: 85411) to prevent evaporation.

Bar-coded assay plates were robotically loaded onto a thermostatically controlled PCR-type thermal block and then heated from 40 to 90° C. at a ramp-rate of 1° C./min for all experiments. Fluorescence was measured by continuous illumination with UV light (Hamamatsu LC6) supplied via fiber optics and filtered through a band-pass filter (380-400 nm; >60D cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded vs temperature and fit to standard equations to yield the T$_m$ (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R., *J Biomol Screen* 2001, 6, 429-40).

EXAMPLE 5

2-AG Accumulation Assay Using HeLa Cells

HeLa cells were homogenated with a Polytron in 10 ml (about 400 million cells) HEPES buffer (HEPES 20 mM, pH 7.4, NaCl 125 mM, EDTA 1 mM, KCl 5 mM, Glucose 20 mM). The homogenate from 20 million cells (0.5 ml) was incubated with MGL inhibitor for 15 min to block MGL activity and then the HEPES buffer solution was incubated with calcium (10 mM) for 20 min. The total reaction volume was 5 ml. The reactions were stopped by 6 mL organic solvent extraction (2:1 chloroform/methanol). Methoxy arachidonyl fluorophosphonate (MAFP) was used as positive control. In the absence of MAFP the 2-AG levels are about 3.4 pmol/sample. In the presence of 100 nM MAFP 2-AG levels increase to 174 pmol/sample. Accumulated 2-AG in the organic phase was measured by a HPLC/MS method, according to the following equation: % MAFP=(Compound 2-AG/MAFP 2-AG)×100.

Representative compounds of formula (I) were tested according to the procedure as described in Example 3, 4 and 5 above, with results as listed in Table 3.

TABLE 3

| Cmpd No. | Ex. 3 (mutant) IC$_{50}$ (μM) | Ex. 3 (wild-type) IC$_{50}$ (μM) | Ex. 4 Kd (μM) | Ex. 5 % MAFP @ 1 μM | Ex. 5 % MAFP @10 μM |
|---|---|---|---|---|---|
| 1 | <0.005 |  | 0.010 |  | 70.5 |
| 2 | <0.005 |  | 0.003 |  | 105.1 |
| 3 | <0.005 |  | 0.008 |  | 67.3 |
| 4 | 0.006 |  | 0.002 |  | 111.5 |
| 5 | 0.007 |  | 0.050 |  | 98.8 |
| 6 | 0.008 | 0.016 | 0.014 | 24.3 | 41.5 |
| 7 | 0.009 |  | 0.002 |  |  |
| 8 | 0.009 |  | 0.018 |  | 58.3 |
| 9 | 0.009 |  | 0.008 |  | 81.0 |

TABLE 3-continued

| Cmpd No. | Ex. 3 (mutant) IC$_{50}$ (µM) | Ex. 3 (wild-type) IC$_{50}$ (µM) | Ex. 4 Kd (µM) | Ex. 5 % MAFP @ 1 µM | Ex. 5 % MAFP @ 10 µM |
|---|---|---|---|---|---|
| 10 | 0.010 | | 0.007 | 97.8 | 115.4 |
| 11 | 0.012 | | 0.004 | | 55.2 |
| 12 | 0.006, 0.009, 0.015, 0.017 | 0.009 | 0.014, 0.025 | 63.1 | 107.9 |
| 13 | <0.013 | | 0.010 | | |
| 14 | 0.016 | | 0.012 | | 105.9 |
| 15 | 0.018 | 0.040 | 0.092 | | 47.6 |
| 16 | 0.019 | | 0.021 | | 91.5 |
| 17 | 0.019 | | 0.007 | | 83.9 |
| 18 | 0.021 | | 0.038 | | 66.2 |
| 19 | 0.022 | | 0.018 | | |
| 20 | 0.023 | <0.005 | 0.062 | | 71.9 |
| 21 | 0.024 | 0.011 | 0.025 | | 79.5 |
| 22 | 0.026 | | 0.017 | | |
| 23 | 0.027 | | 0.036 | | 96.8 |
| 24 | 0.030 | | 0.042 | | 81.9 |
| 25 | 0.032 | | 0.059 | | 87.7 |
| 26 | 0.032 | <0.005 | 0.051 | | 124.6 |
| 27 | 0.034 | 0.060 | 0.055 | 66.2 | 110.1 |
| 28 | 0.035 | | 0.083 | | 82.2 |
| 29 | 0.037 | | 0.229 | | 76.5 |
| 30 | 0.040 | 0.038 | 0.333 | 34.7 | 37.3 |
| 31 | 0.048 | 0.015 | 0.042 | | 69.5 |
| 32 | 0.051 | | 0.029 | | |
| 33 | 0.055 | | 0.027 | 17.5 | 33.0 |
| 34 | 0.055 | | 0.084 | | |
| 35 | 0.055 | | 0.373 | | 66.7 |
| 36 | 0.056 | | 0.031 | | 91.3 |
| 37 | 0.062 | | 0.044 | 32.0 | 65.9 |
| 38 | 0.063 | | 0.192 | | |
| 39 | 0.075 | 0.01 | 0.182 | | 87.6 |
| 40 | 0.078 | | 0.451 | 77.3 | 90.4 |
| 41 | 0.084 | | 0.395 | | 66.8 |
| 42 | 0.104 | 0.162 | 0.118 | | |
| 43 | 0.104 | | 0.400 | | |
| 44 | 0.127 | | 0.556 | | |
| 45 | 0.140 | | 0.244 | | |
| 46 | 0.152 | | 0.454 | | |
| 47 | 0.160 | | 1.021 | | |
| 48 | 0.162 | | 0.435 | | |
| 49 | 0.169 | | 0.704 | | |
| 50 | 0.179 | | 0.284 | | |
| 51 | 0.196 | | 0.417 | | |
| 52 | 0.200 | 0.823 | 1.900 | 28.0 | 52.2 |
| 53 | 0.239 | | 0.333 | | |
| 54 | 0.263 | | 1.319 | | |
| 55 | 0.271 | | 0.364 | | |
| 56 | 0.279 | | 0.250 | | |
| 57 | 0.291 | | 0.577 | | |
| 58 | 0.346 | | 1.083 | | |
| 59 | 0.400 | | 2.300 | 10.2 | 39.7 |
| 60 | 0.450 | | 0.313 | 28.2 | 57.8 |
| 61 | 0.462 | | 2.182 | | |
| 62 | 0.513 | | 4.546 | | |
| 63 | 0.518 | | 2.500 | | |
| 64 | 0.547 | | 0.769 | | |
| 65 | 0.549 | | 0.488 | | |
| 66 | 0.614 | 4.73 | 1.282 | | |
| 67 | 0.620 | | 0.794 | | |
| 68 | 0.624 | | 1.000 | | |
| 69 | 0.735 | | 1.389 | | |
| 70 | 0.749 | | 0.952 | | |
| 71 | 0.761 | | 3.226 | | |
| 72 | 0.967 | | 0.476 | | |
| 73 | 1.002 | | 1.782 | | |
| 74 | 1.200 | | 2.200 | | 29.5 |
| 75 | 1.536 | | 1.923 | | |
| 75 | 1.283 | | 0.769 | | |
| 76 | 1.362 | | 3.849 | | |
| 77 | 1.368 | | 3.030 | | |
| 78 | 1.466 | | 4.584 | | |
| 80 | 1.750 | | 12.500 | | |
| 81 | 2.057 | | 1.161 | | |
| 82 | 2.229 | | 4.546 | | |
| 83 | 2.802 | | 2.381 | | |
| 84 | 3.160 | | 8.333 | | |
| 85 | 3.453 | | 4.545 | | |
| 86 | 3.102 | | 2.381 | | |
| 86 | 5.300 | | 10.200 | | 10.4 |
| 87 | 3.987 | | 1.538 | | |
| 88 | 4.000 | | 7.101 | | 2.8 |
| 89 | 4.503 | | 6.250 | | |
| 90 | 4.576 | | 0.769 | | |
| 91 | 4.664 | | 6.250 | | |
| 92 | >5.00034 | | 4.546 | | |
| 93 | 5.109 | | 2.857 | | |
| 94 | 5.401 | | 4.000 | | |
| 95 | 5.451 | | 4.189 | | |
| 96 | 5.600 | | 15.198 | | 0.0 |
| 97 | 5.880 | | 3.571 | | |
| 98 | 6.028 | | 5.556 | | |
| 99 | 6.100 | | 12.987 | | |
| 100 | 6.500 | | 6.667 | | |
| 101 | 6.515 | | 6.667 | | |
| 102 | 6.593 | | 1.300 | | |
| 103 | 9.425 | | 45.646 | | |
| 104 | 10.109 | | 22.223 | | |
| 105 | 11.403 | | >76.7 | | |
| 106 | 12.482 | | 12.500 | | |
| 107 | 12.850 | | 11.363 | | |
| 108 | 13.262 | | 24.998 | | |
| 109 | 13.338 | | 32.255 | | |
| 110 | 1.687 | | 2.000 | | |
| 111 | <0.013 | | 0.014 | | 106.5 |
| 112 | 0.024 | | 0.120 | | 79.2 |
| 113 | 7.099 | | 4.000 | | |
| 114 | 7.976 | | 10.000 | | |
| 115 | 8.130 | | 6.667 | | |
| 116 | 8.700 | | 6.845 | | |
| 117 | 10.661 | | 18.180 | | |
| 118 | 2.330 | | >76.7 | | |
| 119 | 2.349 | | 4.518 | | |
| 120 | 2.781 | | 2.941 | | |
| 121 | 3.080 | | 2.500 | | |
| 122 | 0.131 | | 0.413 | | 67.8 |
| 123 | 3.460 | | 3.226 | | |
| 124 | 0.263 | | 0.541 | | |
| 125 | 10.789 | | 7.143 | | |
| 126 | 13.240 | | >76.7 | | |
| 128 | | 5.61 | 19.999 | | |
| 129 | | 7.53 | 9.806 | | |
| 130 | 0.653 | | 0.909 | | |
| 131 | 0.628 | | 0.340 | | |
| 132 | 1.227 | | 6.049 | | |
| 133 | 0.844 | | 15.157 | | |
| 134 | 4.290 | | >31.2 | | |
| 135 | 10.792 | | >31.2 | | |
| 139 | | 0.006 | 0.0250 | | |

Compounds #200-223 were similarly tested according to the assay procedures as described in Examples 3, 4 and 5, above with results as listed in Table 4, below.

TABLE 4

| Cmpd No. | Ex. 3 (mutant) IC$_{50}$ (µM) | Ex. 4 Kd (µM) | Ex. 5 % MAFP @ 1 µM | Ex. 5 % MAFP @ 10 µM |
|---|---|---|---|---|
| 200 | 15.2 | 12.5 | | |
| 201 | 15.3 | >76.7 | | |
| 202 | >15.3 | 25 | | |
| 203 | >15.3 | 31.2 | | |
| 204 | >15.3 | >19 | | |
| 205 | >15.3 | >76.7 | | |
| 206 | >16.7 | 12.5 | | |
| 207 | >15.3 | 12.5 | | |
| 208 | >15.3 | 16.7 | | |

TABLE 4-continued

| Cmpd No. | Ex. 3 (mutant) IC$_{50}$ (μM) | Ex. 4 Kd (μM) | Ex. 5 % MAFP @ 1 μM | Ex. 5 % MAFP @ 10 μM |
|---|---|---|---|---|
| 209 | 1.07 | 0.172 | 19.9 | 47.3 |
| 210 | 0.186 | 0.0833 | | 79.5 |
| 211 | 0.050 | 0.130 | 39.7 | 100.8 |
| 212 | 0.220 | 0.330 | | 72.9 |
| 213 | 0.810 | 4.55 | | 61.1 |
| 214 | 0.430 | 0.030 | | 93.5 |
| 215 | 0.0604 | 0.0020 | | |
| 216 | 1.34 | 5.56 | | 86.9 |
| 217 | >15.3 | >76.7 | | |
| 218 | >15.3 | >76.7 | | |
| 219 | >15.3 | >76.7 | | |
| 220 | >15.3 | >76.7 | | |
| 221 | >15.3 | 17.2 | | |
| 222 | >15.3 | >76.7 | | |
| 223 | >17 | >31.2 | | |

EXAMPLE 6

In Vivo Assay

Carrageenan-Induced Paw Edema Model in C57B1/6 Mice

Carrageenan challenge: Male C57B1/6 mice (Taconic) were lightly sedated with a gas mixture of 30% oxygen and 70% carbon dioxide. Using a 27-gauge needle and syringe, 20 microliters of a 2% solution of carrageenan (w/v) in saline was injected into the intraplantar space of the ventral surface of the right hind paw. The control group received an intraplantar injection of saline of equal volume. The animals were allowed to recover, and paw volume measured as an index of tissue edema and inflammation.

Paw volume measurement: Increases in paw volume following the injection of carrageenan serves as a measure of tissue edema and inflammation. Paw volume was measured using a hydro-plethysmometer (Ugo Basaile) at baseline and at 0.5, 1, 2 and 4 hours post-challenge with carrageenan. Percent changes in paw volume from baseline were calculated.

Compound #12 was formulated in a 20% solution of hydroxypropyl beta cyclodextran just prior to administration at a dose of 30 mg/kg and a volume of 10 mL/kg. A single dose of Compound #12 was given orally 30 minutes prior to carrageenan challenge. Vehicle control groups received a single oral dose of the 20% hydroxypropyl beta cyclodextran solution at a dose of 10 mL/kg.

| Pretreatment (po) | Paw Challenge |
|---|---|
| 20% HPbCD | saline |
| 20% HPbCD | 2% carrageenan |
| Compound #12, 30 mg/kg | 2% carrageenan |

Results: Four hours after challenge, carrageenan induced an increase in paw volume as compared to saline challenge (34.5±8.2% and −10.7±2.4%, respectively; p<0.001). Pretreatment with Compound #12 at a dose of 30 mg/kg, sc, 30 minutes prior to carrageenan challenge blunted the increase in paw volume observed four hours after challenge when compared to vehicle pretreatment and carrageenan challenge (17.7±3.3% and 34.5±8.2%, respectively; p<0.04).

EXAMPLE 7

In Vivo Assay

Neuropathic Pain

The sciatic nerve is the major sensorimotor innervation of the (hind) leg and foot. Injury to the sciatic nerve or its constituent spinal nerves often results in pain-related behaviors. In rats and mice, tight ligation of the L5 spinal nerve with silk suture, partial tight ligation of the sciatic nerve with silk suture or loose ligation of the sciatic nerve with chromic gut suture each result in behaviors reminiscent of neuropathic pain in humans. These lesions (one per animal) are performed surgically in anesthetized rodents. Both the spinal nerve and sciatic nerve lesions result in allodynia, a painful response to normally innocuous stimuli, and hyperalgesia, an exaggerated response to normally noxious stimuli. In addition to induction by nerve damage resulting from accidental trauma or surgical procedures, neuropathic pain can also be induced by diabetes (Fox, A et al., *Pain* 81:307-316, 1999) or by treatment with chemotherapeutic agents, such as paclitaxel or vincristine (Yaksh, T L et al., *Pain* 93:69-76, 2001).

Agents that attenuate neuropathic pain in the clinic also are effective in rodent neuropathic pain models. These agents include the recently approved Cymbalta (Duloxetine, Iyengar, S., et al., *JPET* 2004 311:576-584), morphine (Suzuki, R et al., *Pain* 1999 80:215-228) and gabapentin (Hunter, J C et al., *Eur J Pharmacol* 1997 324:153-160). The dual TRPV1/TRPM8 receptor antagonist BCTC reduced mechanical hyperalgesia and tactile allodynia in the chronic constriction injury rodent neuropathic pain model (Pomonis, J D et al., *JPET* 2003 306:387-393; Behrendt, H et al., *Brit J Pharm* 2004 141:737). Cold allodynia is a particularly debilitating symptom of neuropathic pain conditions (Jorum E et al. *Pain* 2003 101: 229-235). The antiallodynic effect of compounds of the Formula (I) as defined herein in this rodent model is predictive of clinical effect for these novel agents.

EXAMPLE 7a

In Vivo Assay

Chronic Constriction Injury (CCI)-Induced Model of Neuropathic Pain—Acetone-Induced Hypersensitivity Male Sprague Dawley rats (225-450 g; n=5-8/treatment) were used to evaluate the ability of selected compounds of the Formula (I) to reverse CCI-induced cold hypersensitivity. Four loose ligatures of 4-0 chromic gut were surgically placed around the left sciatic nerve under inhalation anesthesia as described by Bennett et al (Bennett G J, Xie Y K. *Pain* 1988, 33(1): 87-107). Fourteen to 35 days following CCI surgery, subjects were placed in elevated observation chambers containing wire mesh floors, and five applications of acetone (0.05 mL/application separated by approximately 5 minutes) were spritzed onto the plantar surface of the paw using a multidose syringe. An abrupt withdrawal or lifting of the paw was considered a positive response. The number of positive responses was recorded for each rat over the five trials. Following baseline withdrawal determinations, compounds of formula (I) were administered in an appropriate vehicle, such as hydroxypropyl-β-cyclodextrin (HP β CD), methylcellulose, Methocel, 10% Solutol, or H$_2$O, or the like, by the appropriate route, i.p. or p.o. The number of withdrawals were re-determined 1 to 4 h after compound administration.

Results are presented as a percent inhibition of shakes, which was calculated for each subject as [1−(test compound withdrawals/pre-test withdrawals)]×100 and then averaged by treatment. Compound #12 was tested according to the procedure as described above, with results as listed in Table 5, below.

TABLE 5

Compound #12 (HCl salt); 30 mg/kg oral dosing in 20% HPbCD

| Pretreatment Time, hr | Percent Inhibition |
| --- | --- |
| 1 | 57.1 |
| 2 | 74.3 |
| 3 | 80.0 |
| 4 | 48.6 |

EXAMPLE 8

In Vivo Assay

Visceral Hyperalgesia Model

This protocol uses barostat-controlled, isobaric colorectal distensions (CRD) in rats to evaluate the potency and efficacy of test compounds in treating visceral hyperalgesia. Male Sprague Dawley rats, weighing 275-350 g, (Charles River Labs) were housed 2-4/cage in a temperature and humidity controlled room with a 12 h/12 h light/dark cycle and ad libitum access to food and water. One day after release from quarantine, rats were acclimated to progressively longer (30 min and, 4 h later, 45 min) periods of simple restraint in plexiglass devices (G-3, rat ECU; Braintree Scientific; Braintree Mass.). The rats were returned to their home cage overnight. The next day, they were acclimated in the restraint device for 60 min in the morning and 4 h later, lightly anesthetized with 70% $CO_2$: 30% $O_2$, and a highly compliant, 4-cm long polyethylene balloon, lubricated with K-Y® brand lubricating jelly, was inserted per anus into the rectum and distal colon. The balloon was positioned such that the aboral end was 1 cm from the anus and secured in place by taping the balloon catheter to the base of the tail. The catheter was connected to a computerized barostat that controlled the inflation of the balloon and thus CRD. The balloon pressure, which represents intracolonic pressure, was continuously recorded.

CRD in conscious animals elicits a reflex visceromotor response (VMR), consisting of contraction of the anterior abdominal wall muscles (Ness T J, and Gebhart G F, Colorectal distension as a noxious visceral stimulus: physiologic and pharmacologic characterization of pseudaffective reflexes in the rat, *Brain Res* 1988, 450: 153-169). Contraction of these muscles increases intraabdominal pressure and subsequently increases intracolonic pressure. Changes in intracolonic pressure are transduced through the same balloon used to deliver the CRD. The manometric VMR mimics the myoelectric VMR recorded from electrodes placed in the anterior abdominal wall muscles in rat (Tammpere A, Brusberg M, Axenborg J, Hirsch I, Larsson H, and Lindstrom E., Evaluation of pseudo-affective responses to noxious colorectal distension in rats by manometric recordings, *Pain* 2005, 116: 220-226).

Stimulus-response data were obtained by delivering two series of 20-sec distensions of stepwise (15 mmHg increments) increasing pressure at four-min intervals and recording the manometric response as follows: the intracolonic pressure signal was passed through a digital 1-Hz highpass filter and rectified, and then the integral of the initial 15 sec of the CRD was subjected to baseline subtraction (the 15 sec immediately preceding balloon distension); the baseline-subtracted manometric VMR to distending pressures of 15, 30, 45 mmHg were averaged to obtain a control stimulus-response relationship for each rat. Colorectal balloons were removed, and the rats were returned to their home cages.

The following morning, colitis was induced by the intracolonic instillation of a 1.5-mL bolus of 2.5% (w/v) zymosan A (from *Saccharomyces cerevisiae*; Sigma Chemical Co., St. Louis) in 30% ethanol under light 70% $CO_2$: 30% $O_2$ anesthesia. Four hours later, the rats were lightly anesthetized and the colorectal balloons were inserted as on the previous day for control distensions. The identical CRD stimuli were applied, and manometric VMRs were recorded and analyzed as described for the control phase of the experiment. Rats were then subcutaneously (s.c.) administered 1 mg/kg with 3, 10 or 30 mg/kg test compound that was solubilized in 20% hydroxypropyl-β-cyclodextrin (N=14, 10 and 6, respectively). CRD stimuli were applied 20 min after dosing. CRD stimuli at 45 mmHg elicited peak responses in the control (pre-zymosan) condition; therefore, the responses of each rat were calculated as a percent of the manometric VMR at that pressure, recorded the day before induction of colitis; thus, each rat served as its own control. VMR data from rats in which the post-zymosan VMR at 45 mmHg was not greater than 100% of control (N=7) were excluded.

Compound #12 (30 mg/kg, s.c.) reversed the hyperalgesic response to 45 mmHg CRD in this model of visceral pain (103.8±22.1% of control vs. 239.6±28.9% of control in vehicle-treated rats (P<0.001 compared to control).

EXAMPLE 9

In Vivo Assay

CFA-Induced Paw Radiant Heat Hypersensitivity

Each rat was placed in a test chamber on a thermally controlled glass surface and allowed to acclimate for approximately 10 min. A radiant thermal stimulus (beam of light) was then focused through the glass onto the plantar surface of the hind paw. The thermal stimulus was automatically shut off by a photoelectric relay when the paw was moved or when the cut-off time was reached (20 sec). An initial (baseline) response latency to the thermal stimulus was recorded for each animal prior to the injection of CFA. 24 h following intraplantar CFA injection, the response latency to the thermal stimulus was then re-evaluated and compared to the animal's baseline response time. Only rats that exhibit at least a 25% reduction in response latency (i.e., hyperalgesia) were included in further analysis. Immediately following the post-CFA latency assessment, test compound or vehicle (usually solutol, hydroxypropyl methylcellulose, hydroxypropyl beta-cyclodextrin or PEG-400) was administered i.p. or p.o. to rats. Post-compound treatment withdrawal latencies were assessed at fixed time intervals, typically 30, 60 and 120 minutes. The percent reversal of hypersensitivity is calculated according to the following formula: % reversal=(post dose latency-predoselatency)/(baseline (pre CFA) latency-predose latency)×100.

Compound #12 (as its corresponding HCl salt) was administered in a solution of 20% HPβCD, at a dose of 30 mg/kg, i.p. and a treatment time of 30 min. The compound was measured to result in 90.3% reversal of hypersensitivity and exhibit an $ED_{50}$ value of 0.9 mg/kg.

EXAMPLE 10

Solid, Oral Formulation

Prophetic Example

As a specific embodiment of an oral composition, 100 mg of the Compound #12, prepared as in Example 1, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

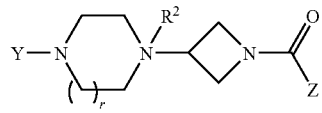

(I)

wherein
Y is phenyl or a heteroaryl selected from the group consisting of thiazolyl, pyridyl, pyrimidinyl, 1,3,5-triazinyl, benzoxazolyl, benzisoxazolyl, benzthiazolyl, and 1,3,4-thiadiazolyl;
wherein the phenyl or heteroaryl is optionally substituted with one substituent selected from the group consisting of fluoro, chloro, bromo, iodo, $C_{1-4}$alkyl, trifluoromethyl, $C_{1-4}$alkoxy, $C_{1-4}$alkylthio, nitro and cyano;
r is an integer from 1 to 2;
$R^2$ is absent or is oxido;
Z is selected from the group consisting of
(a) phenyl substituted with $NR^aR^b$;
wherein $R^a$ is hydrogen or $C_{1-4}$alkyl; wherein $R^b$ is $C_{1-4}$alkyl, cycloalkyl, phenyl, furanylmethyl, or phenyl($C_{1-2}$alkyl); and wherein the phenyl or of $R^b$, the phenyl of phenyl($C_{1-2}$alkyl) of $R^b$ or the furanyl of furanylmethyl of $R^b$ are optionally substituted with an iodo substituent;
alternatively, $R^a$ and $R^b$ are taken together with the nitrogen atom to which they are both bound to form a 5 to 8 membered heterocyclyl, which heterocyclyl is optionally fused to a benzo group;
(b) biphenyl-3-yl or biphenyl-4-yl; wherein the interior phenyl ring, attached to the carbonyl of Formula (I) is optionally substituted with a fluoro substituent; and wherein the terminal phenyl ring is optionally substituted with a substituent selected from the group consisting of trifluoromethyl, $C_{1-4}$alkoxy, chloro, dichloro, fluoro, and iodo;
(c) phenyl substituted with a substituent selected from the group consisting of $C_{5-8}$cycloalkyl, —NHC(=O)cyclohexyl, phenyloxy, phenylcarbonyl, phenyl($C_{1-3}$)alkyl, phenyl($C_{1-3}$)alkoxy, pyrrolyl, pyrazolyl, imidazolyl, isoindol-2-yl-1,3-dione, 2,3-dihydro-isoindol-2-yl; 1-(t-butoxycarbonyl)piperidin-4-yloxy, and 1-(t-butoxycarbonyl)piperidin-4-yl;

(d) phenyl substituted with one to two substituents independently selected from the group consisting of $C_{1-6}$alkyl, $C_{1-4}$alkoxy, iodo, chloro and nitro;
(e) phenyl($C_{1-2}$)alkyl-; wherein the phenyl is optionally substituted with one to two substituent independently selected from the group consisting of iodo, fluoro, $C_{1-6}$alkyl, phenyl, and $NR^cR^d$; wherein $R^c$ is hydrogen or $C_{1-4}$alkyl; a wherein $R^d$ is $C_{1-4}$alkyl or $C_{3-6}$cycloalkyl($C_{1-4}$)alkyl; and wherein the $C_{1-2}$alkyl of phenyl($C_{1-2}$)alkyl is optionally substituted with phenyl;
(f) phenyl($C_{2-4}$)alkenyl-; wherein the phenyl is optionally substituted with a substituent selected from the group consisting of $C_{1-4}$alkyl, $C_{1-4}$alkoxy, trifluoromethyl, trifluoromethylthio and phenyl;
(g) naphthyl; wherein the naphthyl is optionally substituted with one $C_{1-4}$alkoxy substituent;
(h) fluorenyl or xanthenyl; wherein the fluorenyl or xanthenyl is optionally substituted with oxo;
(i) $C_{5-8}$cycloalkyl; wherein the $C_{5-8}$cycloalkyl is optionally substituted with one $C_{1-6}$alkyl substituent;
(j) benzofused $C_{5-8}$cycloalkyl or benzofused $C_{5-8}$cycloalkyl($C_{1-4}$)alkyl; wherein said $C_{5-8}$cycloalkyl portion is optionally substituted with 1 to 4 methyl substituents
(k) bicyclo[2.2.2]octyl-1-yl; wherein the bicyclo[2.2.2]octyl-1-yl is optionally substituted with $C_{1-6}$alkyl;
(l) a heteroaryl or benzo-fused heteroaryl selected from the group consisting of benzooxazolyl, quinolinyl, benzimidazolyl, pyridinyl, indolyl, thienyl, furanyl, pyrazolyl, oxazolyl, benzothienyl, and benzofuranyl;
wherein the heteroaryl or benzo-fused heteroaryl is optionally substituted with one to two substituents independently selected from the group consisting of $C_{1-4}$alkyl, trifluoromethyl, $C_{5-8}$cycloalkyl, phenyl, phenyl($C_{1-2}$)alkoxy, phenyl($C_{2-4}$)alkynyl and dichlorophenoxy; and wherein the phenyl substituent on the heteroaryl is further optionally substituted with a substituent selected from $C_{1-4}$alkyl, $C_{1-4}$alkoxy or trifluoromethyl;
(m) 1,5-diphenyl-1H-pyrazol-3-yl; wherein the pyrazol-3-yl is optionally substituted with a methyl substituent; and wherein each of the phenyl groups of the 1,5-diphenyl substituents is further optionally substituted with a substituent selected from chloro, dichloro or aminosulfonyl;
(n) 1,2,3,4-tetrahydro-quinolin-6-yl; wherein the 1,2,3,4-tetrahydro-quinolin-6-yl is optionally substituted with phenyl or trifluoromethyl substituted phenyl; and
(o) benzofused heterocyclyl($C_{2-4}$)alkenyl; wherein the benzofused heterocyclyl is attached to the $C_{2-4}$alkenyl via the benzo ring; and wherein benzofused heterocyclyl is further optionally substituted with $C_{5-6}$cycloalkyl;
or an enantiomer, diastereomer or pharmaceutically acceptable salts thereof;
with the proviso that the compound of formula (I) is other than
a compound wherein Y is 3-methylpyridin-2-yl, r is 1, and $R^2$ is absent and Z is 4-biphenyl;
a compound wherein Y is pyridin-2-yl, r is 1, and $R^2$ is absent and Z is 2-(phenylcarbonyl)phenyl;
a compound wherein Y is 5-trifluoromethylpyridin-2-yl, r is 1, and $R^2$ is absent and Z is 4-cyclohexyl-phenyl;
a compound wherein Y is pyridin-2-yl, r is 1, and $R^2$ is absent and Z is 3-(cyclohexylcarbonylamino)phenyl;
a compound wherein Y is 5-cyanopyridin-2-yl, r is 1, and $R^2$ is absent and Z is 4-biphenyl;

a compound wherein Y is 5-trifluoromethylpyridin-2-yl, r is 1, and $R^2$ is absent and Z is 4-biphenyl;
a compound wherein Y is pyrimidin-2-yl, r is 2, and $R^2$ is absent and Z is 2-(4-trifluoromethylthiophenyl)-vinyl;
a compound wherein Y is pyridin-2-yl, r is 1, and $R^2$ is absent and Z is 2-phenyl-vinyl;
a compound wherein Y is pyridin-2-yl, r is 1, and $R^2$ is absent and Z is 2-phenylethyl;
a compound wherein Y is pyridin-2-yl, r is 1, and $R^2$ is absent and Z is 2-t-butyl-benzoxazol-6-yl;
a compound wherein Y is pyridin-2-yl, r is 1, and $R^2$ is absent and Z is 2-(4-methoxyphenyl)-benzoxazol-7-yl;
a compound wherein Y is pyridin-2-yl, r is 1, and $R^2$ is absent and Z is 2-cyclohexyl-benzoxazol-6-yl;
a compound wherein Y is pyridin-2-yl, r is 1, and $R^2$ is absent and Z is 1,2-diisobutyl-1H-indol-5-yl;
a compound wherein Y is pyridin-2-yl, r is 1, and $R^2$ is absent and Z is 1-methyl-2-propyl-1H-indol-5-yl;
a compound wherein Y is pyridin-2-yl, r is 1, and $R^2$ is absent and Z is 1-isobutyl-2-phenyl-1H-indol-5-yl;
a compound wherein Y is pyridin-2-yl, r is 1, and $R^2$ is absent and Z is 1-isobutyl-2-(4-methylphenyl)-1H-indol-5-yl;
a compound wherein Y is pyridin-2-yl, r is 1, and $R^2$ is absent and Z is 2-(3-methoxyphenyl)-benzoxazol-5-yl;
a compound wherein Y is pyridin-2-yl, r is 1, and $R^2$ is absent and Z is 2-benzylphenyl;
a compound wherein Y is pyridin-2-yl, r is 1, and $R^2$ is absent and Z is (1R)-1,2,3,4-tetrahydronaphthalen-1-yl;
a compound wherein Y is pyridin-2-yl, r is 1, and $R^2$ is absent and Z is (1S)-1-[4-(2-methylpropyl)phenyl]ethyl;
a compound wherein Y is pyridin-2-yl, r is 1, and $R^2$ is absent and Z is (1S)-1-(2-fluoro-[1,1'-biphenyl]-4-yl)ethyl;
a compound wherein Y is pyridin-2-yl, r is 1, and $R^2$ is absent and Z is 2,3-dihydro-1H-inden-2-yl;
a compound wherein Y is pyridin-2-yl, r is 1, and $R^2$ is absent and Z is 2,2-diphenylethyl;
a compound wherein Y is pyrimidin-2-yl, r is 1, and $R^2$ is absent and Z is 2-cyclohexyl-benzoxazol-6-yl; or
a compound wherein Y is 3-trifluoromethylphenyl, r is 1, and $R^2$ is absent and Z is 1,2,3,4-tetrahydroquinolin-6-yl.

2. A compound as in claim 1, wherein
Y is selected from the group consisting of phenyl, pyridyl, pyrimidyl, 1,3,5-triazinyl, thiazolyl, 1,3,4-thiadiazolyl, benzoxazolyl, benzisoxazolyl and benzothiazolyl; wherein the phenyl, pyridyl, pyrimidyl, 1,3,5-triazinyl, thiazolyl, 1,3,4-thiadiazolyl, benzoxazolyl, benzisoxazolyl, benzothiazolyl is optionally substituted with a substituent selected from the group consisting of cyano, fluoro, chloro, bromo, iodo, $C_{1-4}$alkyl, trifluoromethyl, $C_{1-4}$alkoxy, $C_{1-4}$alkylthio and nitro;
r is an integer from 1 to 2;
$R^2$ is absent or is oxido;
Z is selected from the group consisting of
(a) phenyl substituted with $NR^aR^b$; wherein $R^a$ is hydrogen or $C_{1-4}$alkyl; and $R^b$ is $C_{1-4}$alkyl, cycloalkyl, phenyl, furanylmethyl, or phenyl($C_{1-2}$alkyl); and wherein the phenyl of $R^b$, the phenyl of phenyl($C_{1-2}$alkyl) of $R^b$ or the furanyl of furanylmethyl of $R^b$ are optionally substituted with one iodo substituent; alternatively, $R^a$ and $R^b$ are taken together with the nitrogen atom to which they are both bound to form a 5 to 6 membered heterocyclyl, which heterocyclyl is optionally fused to a benzo group;
(b) biphenyl-3-yl or biphenyl-4-yl; wherein the terminal phenyl ring of is optionally substituted with a substituent selected from the group consisting of trifluoromethyl, $C_{1-4}$alkoxy, chloro, dichloro, fluoro, and iodo;
(c) phenyl substituted with a substituent selected from the group consisting of $C_{5-8}$cycloalkyl, —NHC(=O)cyclohexyl, phenyloxy, phenylcarbonyl, phenyl($C_{1-3}$)alkoxy, benzyl, pyrrolyl, pyrazolyl, imidazolyl, isoindol-2-yl-1, 3-dione, 2,3-dihydro-isoindol-2-yl; 1-(t-butoxycarbonyl)piperidin-4-yloxy, and 1-(t-butoxycarbonyl)piperidin-4-yl;
(d) phenyl substituted with one to two substituents independently selected from the group consisting of $C_{1-6}$alkyl, $C_{1-4}$alkoxy, iodo, chloro and nitro;
(e) phenyl($C_{1-2}$)alkyl-; wherein the phenyl is optionally substituted with one to two substituent independently selected from the group consisting of iodo, fluoro, $C_{1-6}$alkyl, phenyl, and $NR^cR^d$; wherein $R^c$ is hydrogen or $C_{1-4}$alkyl; and wherein $R^d$ is $C_{1-4}$alkyl or $C_{3-6}$cycloalkyl($C_{1-4}$alkyl; and wherein the $C_{1-2}$alkyl of phenyl($C_{1-2}$)alkyl is optionally substituted with phenyl;
(f) phenyl($C_{2-4}$)alkenyl-; wherein the phenyl is optionally substituted with a substituent selected from the group consisting of trifluoromethylthio, $C_{1-4}$alkyl, $C_{1-4}$alkoxy, phenyl, and trifluoromethyl;
(g) naphthyl; wherein the naphthyl is optionally substituted with one $C_{1-4}$alkoxy substituent;
(h) fluorenyl or xanthenyl; wherein the fluorenyl or xanthenyl is optionally substituted with oxo;
(i) $C_{5-6}$cyclalkyl; wherein the $C_{5-6}$cycloalkyl is optionally substituted with one $C_{1-5}$alkyl substituent;
(j) benzofused $C_{5-6}$cycloalkyl or benzofused $C_{5-6}$cycloalkyl($C_{1-4}$)alkyl; wherein said $C_{5-6}$cycloalkyl portion is optionally substituted with 1 to 4 methyl substituents
(k) bicyclo[2.2.2]octyl-1-yl; wherein the bicyclo[2.2.2]octyl-1-yl is optionally substituted with $C_{1-6}$alkyl;
(l) a heteroaryl or benzo-fused heteroaryl selected from the group consisting of benzooxazolyl, quinolinyl, benzimidazolyl, pyridinyl, indolyl, thienyl, furanyl, pyrazolyl, oxazolyl, benzothienyl, and benzofuranyl;
wherein the heteroaryl or benzo-fused heteroaryl is optionally substituted with one to two substituents independently selected from the group consisting of $C_{5-6}$cycloalkyl, $C_{1-4}$alkyl, phenyl, trifluoromethyl, phenyl($C_{1-2}$)alkoxy, dichlorophenoxy, and phenyl-ethynyl; and wherein the phenyl substituent on the heteroaryl is further optionally substituted with a substituent selected from methyl, methoxy, or trifluoromethyl;
(m) 1,5-diphenyl-1H-pyrazol-3-yl; wherein the pyrazol-3-yl is optionally substituted with a methyl substituent; and wherein each of the phenyl groups of the 1,5-diphenyl substituents is optionally substituted with a substituent selected from chloro, dichloro or aminosulfonyl;
(n) 1,2,3,4-tetrahydro-quinolin-6-yl; wherein the 1,2,3,4-tetrahydro-quinolin-6-yl is optionally substituted with phenyl or trifluoromethyl substituted phenyl; and
(o) benzofused heterocyclyl($C_{2-4}$)alkenyl; wherein the benzofused heterocyclyl is attached to the $C_{2-4}$alkenyl via the benzo ring; and wherein benzofused heterocyclyl is optionally substituted with $C_{5-6}$cycloalkyl;
or an enantiomer, diastereomer or pharmaceutically acceptable salts thereof;
with the proviso that the compound of formula (I) is other than
a compound wherein Y is 3-methylpyridin-2-yl, r is 1, and $R^2$ is absent and Z is 4-biphenyl;

a compound wherein Y is pyridin-2-yl, r is 1, and $R^2$ is absent and Z is 2-(phenylcarbonyl)phenyl;

a compound wherein Y is 5-trifluoromethylpyridin-2-yl, r is 1, and $R^2$ is absent and Z is 4-cyclohexyl-phenyl;

a compound wherein Y is pyridin-2-yl, r is 1, and $R^2$ is absent and Z is 3-(cyclohexylcarbonylamino)phenyl;

a compound wherein Y is 5-cyanopyridin-2-yl, r is 1, and $R^2$ is absent and Z is 4-biphenyl;

a compound wherein Y is 5-trifluoromethylpyridin-2-yl, r is 1, and $R^2$ is absent and Z is 4-biphenyl;

a compound wherein Y is pyrimidin-2-yl, r is 2, and $R^2$ is absent and Z is 2-(4-trifluoromethylthiophenyl)-vinyl;

a compound wherein Y is pyridin-2-yl, r is 1, and $R^2$ is absent and Z is 2-phenyl-vinyl;

a compound wherein Y is pyridin-2-yl, r is 1, and $R^2$ is absent and Z is 2-phenylethyl;

a compound wherein Y is pyridin-2-yl, r is 1, and $R^2$ is absent and Z is 2-t-butyl-benzoxazol-6-yl;

a compound wherein Y is pyridin-2-yl, r is 1, and $R^2$ is absent and Z is 2-(4-methoxyphenyl)-benzoxazol-7-yl;

a compound wherein Y is pyridin-2-yl, r is 1, and $R^2$ is absent and Z is 2-cyclohexyl-benzoxazol-6-yl;

a compound wherein Y is pyridin-2-yl, r is 1, and $R^2$ is absent and Z is 1,2-diisobutyl-1H-indol-5-yl;

a compound wherein Y is pyridin-2-yl, r is 1, and $R^2$ is absent and Z is 1-methyl-2-propyl-1H-indol-5-yl;

a compound wherein Y is pyridin-2-yl, r is 1, and $R^2$ is absent and Z is 1-isobutyl-2-phenyl-1H-indol-5-yl;

a compound wherein Y is pyridin-2-yl, r is 1, and $R^2$ is absent and Z is 1-isobutyl-2-(4-methylphenyl)-1H-indol-5-yl;

a compound wherein Y is pyridin-2-yl, r is 1, and $R^2$ is absent and Z is 2-(3-methoxyphenyl)-benzoxazol-5-yl;

a compound wherein Y is pyridin-2-yl, r is 1, and $R^2$ is absent and Z is 2-benzylphenyl;

a compound wherein Y is pyridin-2-yl, r is 1, and $R^2$ is absent and Z is (1R)-1,2,3,4-tetrahydronaphthalen-1-yl;

a compound wherein Y is pyridin-2-yl, r is 1, and $R^2$ is absent and Z is (1S)-1-[4-(2-methylpropyl)phenyl]ethyl;

a compound wherein Y is pyridin-2-yl, r is 1, and $R^2$ is absent and Z is (1S)-1-(2-fluoro-[1,1'-biphenyl]-4-yl)ethyl;

a compound wherein Y is pyridin-2-yl, r is 1, and $R^2$ is absent and Z is 2,3-dihydro-1H-inden-2-yl;

a compound wherein Y is pyridin-2-yl, r is 1, and $R^2$ is absent and Z is 2,2-diphenylethyl;

a compound wherein Y is pyrimidin-2-yl, r is 1, and $R^2$ is absent and Z is 2-cyclohexyl-benzoxazol-6-yl; or a compound wherein Y is 3-trifluoromethylphenyl, r is 1, and $R^2$ is absent and Z is 1,2,3,4-tetrahydroquinolin-6-yl.

3. A compound as in claim 1, wherein

Y is selected from the group consisting of phenyl, pyridyl, pyrimidyl, 1,3,5-triazinyl, thiazolyl, 1,3,4-thiadiazolyl, benzooxazolyl, benzisoxazolyl and benzothiazolyl; wherein the phenyl, pyridyl, pyrimidyl, 1,3,5-triazinyl, thiazolyl, 1,3,4-thiadiazolyl, benzooxazolyl, benzisoxazolyl, benzothiazolyl is optionally substituted with a substituent selected from the group consisting of cyano, fluoro, chloro, bromo, iodo, $C_{1-2}$alkyl, trifluoromethyl, $C_{1-2}$alkoxy, $C_{1-2}$alkylthio and nitro;

r is an integer from 1 to 2;

$R^2$ is absent or is oxido;

Z is selected from the group consisting of (a) phenyl substituted with $NR^aR^b$; wherein $R^a$ is hydrogen or $C_{1-4}$alkyl; and $R^b$ is $C_{1-4}$alkyl, cycloalkyl, phenyl, furanylmethyl, or benzyl; and wherein the phenyl or benzyl of $R^b$ or the furanyl of furanylmethyl of $R^b$ are optionally substituted with one iodo substituent; alternatively, $R^a$ and $R^b$ are taken together with the nitrogen atom to which they are both bound to form 1-pyrrolidinyl or 1-azepanyl;

(b) biphenyl-3-yl or biphenyl-4-yl; wherein the terminal phenyl ring of is optionally substituted with a substituent selected from the group consisting of trifluoromethyl, $C_{1-4}$alkoxy, chloro, dichloro, fluoro, and iodo;

(c) phenyl substituted with a substituent selected from the group consisting of cyclohexyl, —NHC(=O)cyclohexyl, phenyloxy, phenylcarbonyl, benzyloxy, benzyl, pyrrolyl, pyrazolyl, imidazolyl, isoindol-2-yl-1,3-dione, 2,3-dihydro-isoindol-2-yl; 1-(t-butoxycarbonyl)piperidin-4-yloxy, and 1-(t-butoxycarbonyl)piperidin-4-yl;

(d) phenyl substituted with one to two substituents independently selected from the group consisting of $C_{1-6}$alkyl, $C_{1-4}$alkoxy, iodo, chloro and nitro;

(e) phenyl($C_{1-2}$)alkyl-; wherein the phenyl is optionally substituted with one to two substituent independently selected from the group consisting of iodo, fluoro, $C_{1-6}$alkyl, phenyl, and $NR^cR^d$; wherein $R^c$ is hydrogen or $C_{1-4}$alkyl; and wherein $R^d$ is $C_{1-4}$alkyl or $C_{3-6}$cycloalkyl($C_{1-4}$alkyl; and wherein the $C_{1-2}$alkyl of phenyl($C_{1-2}$)alkyl is optionally substituted with phenyl;

(f) phenyl($C_{2-4}$alkenyl-; wherein the phenyl is optionally substituted with a substituent selected from the group consisting of trifluoromethylthio, $C_{1-4}$alkyl, $C_{1-4}$alkoxy, and trifluoromethyl;

(g) naphthyl; wherein the naphthyl is optionally substituted with one $C_{1-4}$alkoxy substituent;

(h) fluorenyl or xanthenyl; wherein the fluorenyl or xanthenyl is optionally substituted with oxo;

(i) cyclohexyl; wherein the cyclohexyl is optionally substituted with one $C_{1-6}$alkyl substituent;

(j) benzofused $C_{5-6}$cycloalkyl or benzofused $C_{5-6}$cycloalkyl($C_{1-4}$)alkyl; wherein said $C_{5-6}$cycloalkyl portion is optionally substituted with 1 to 4 methyl substituents;

(k) bicyclo[2.2.2]octyl-1-yl; wherein the bicyclo[2.2.2]octyl-1-yl is optionally substituted with $C_{1-6}$alkyl;

(l) a heteroaryl or benzo-fused heteroaryl selected from the group consisting of benzooxazolyl, quinolinyl, benzimidazolyl, pyridinyl, indolyl, thienyl, furanyl, pyrazolyl, oxazolyl, benzothienyl, and benzofuranyl; wherein the heteroaryl or benzo-fused heteroaryl is optionally substituted with one to two substituents independently selected from the group consisting of cyclohexyl, $C_{1-4}$alkyl, phenyl, trifluoromethyl, benzyloxy, dichlorophenoxy, and phenyl-ethynyl; and wherein the phenyl substituent on the heteroaryl is further optionally substituted with a substituent selected from methyl, methoxy, or trifluoromethyl;

(m) 1,5-diphenyl-1H-pyrazol-3-yl; wherein the pyrazol-3-yl is optionally substituted with a methyl substituent; and wherein each of the phenyl groups of the 1,5-diphenyl substituents is optionally substituted with a substituent selected from chloro, dichloro or aminosulfonyl;

(n) 1,2,3,4-tetrahydro-quinolin-6-yl; wherein the 1,2,3,4-tetrahydro-quinolin-6-yl is optionally substituted with phenyl or trifluoromethyl substituted phenyl; and (o) benzofused heterocyclyl($C_{2-4}$)alkenyl; wherein the benzofused heterocyclyl is attached to the $C_{2-4}$alkenyl via the benzo ring; and wherein benzofused heterocyclyl is optionally substituted with cyclohexyl;

or an enantiomer, diastereomer or pharmaceutically acceptable salts thereof;

with the proviso that the compound of formula (I) is other than a compound wherein Y is 3-methylpyridin-2-yl, r is 1, and $R^2$ is absent and Z is 4-biphenyl;

a compound wherein Y is pyridin-2-yl, r is 1, and $R^2$ is absent and Z is 2-(phenylcarbonyl)phenyl;

a compound wherein Y is 5-trifluoromethylpyridin-2-yl, r is 1, and $R^2$ is absent and Z is 4-cyclohexyl-phenyl;

a compound wherein Y is pyridin-2-yl, r is 1, and $R^2$ is absent and Z is 3-(cyclohexylcarbonylamino)phenyl;

a compound wherein Y is 5-cyanopyridin-2-yl, r is 1, and $R^2$ is absent and Z is 4-biphenyl;

a compound wherein Y is 5-trifluoromethylpyridin-2-yl, r is 1, and $R^2$ is absent and Z is 4-biphenyl;

a compound wherein Y is pyrimidin-2-yl, r is 2, and $R^2$ is absent and Z is 2-(4-trifluoromethylthiophenyl)-vinyl;

a compound wherein Y is pyridin-2-yl, r is 1, and $R^2$ is absent and Z is 2-phenyl-vinyl;

a compound wherein Y is pyridin-2-yl, r is 1, and $R^2$ is absent and Z is 2-phenylethyl;

a compound wherein Y is pyridin-2-yl, r is 1, and $R^2$ is absent and Z is 2-t-butyl-benzoxazol-6-yl;

a compound wherein Y is pyridin-2-yl, r is 1, and $R^2$ is absent and Z is 2-(4-methoxyphenyl)-benzoxazol-7-yl;

a compound wherein Y is pyridin-2-yl, r is 1, and $R^2$ is absent and Z is 2-cyclohexyl-benzoxazol-6-yl;

a compound wherein Y is pyridin-2-yl, r is 1, and $R^2$ is absent and Z is 1,2-diisobutyl-1H-indol-5-yl;

a compound wherein Y is pyridin-2-yl, r is 1, and $R^2$ is absent and Z is 1-methyl-2-propyl-1H-indol-5-yl;

a compound wherein Y is pyridin-2-yl, r is 1, and $R^2$ is absent and Z is 1-isobutyl-2-phenyl-1H-indol-5-yl;

a compound wherein Y is pyridin-2-yl, r is 1, and $R^2$ is absent and Z is 1-isobutyl-2-(4-methylphenyl)-1H-indol-5-yl;

a compound wherein Y is pyridin-2-yl, r is 1, and $R^2$ is absent and Z is 2-(3-methoxyphenyl)-benzoxazol-5-yl;

a compound wherein Y is pyridin-2-yl, r is 1, and $R^2$ is absent and Z is 2-benzylphenyl;

a compound wherein Y is pyridin-2-yl, r is 1, and $R^2$ is absent and Z is (1R)-1,2,3,4-tetrahydronaphthalen-1-yl;

a compound wherein Y is pyridin-2-yl, r is 1, and $R^2$ is absent and Z is (1S)-1-[4-(2-methylpropyl)phenyl]ethyl;

a compound wherein Y is pyridin-2-yl, r is 1, and $R^2$ is absent and Z is (1S)-1-(2-fluoro-[1,1'-biphenyl]-4-yl)ethyl;

a compound wherein Y is pyridin-2-yl, r is 1, and $R^2$ is absent and Z is 2,3-dihydro-1H-inden-2-yl;

a compound wherein Y is pyridin-2-yl, r is 1, and $R^2$ is absent and Z is 2,2-diphenylethyl;

a compound wherein Y is pyrimidin-2-yl, r is 1, and $R^2$ is absent and Z is 2-cyclohexyl-benzoxazol-6-yl; or a compound wherein Y is 3-trifluoromethylphenyl, r is 1, and $R^2$ is absent and Z is 1,2,3,4-tetrahydroquinolin-6-yl.

4. A compound as in claim 1, wherein

Y is selected from the group consisting of phenyl, 3-trifluoromethyl-phenyl, 4-trifluoromethyl-phenyl, 2-methoxy-phenyl, 2-methylthio-phenyl, 2-nitro-phenyl, pyrid-2-yl, 3-cyano-pyrid-2-yl, 5-cyano-pyrid-2-yl, 5-bromo-pyrid-2-yl, 3-chloro-pyrid-2-yl, 5-chloro-pyrid-2-yl, 3-iodo-pyrid-2-yl, 3-methyl-pyrid-2-yl, 4-methyl-pyrid-2-yl, 3-trifluoromethyl-pyrid-2-yl, pyrimidin-2-yl, 1,3,5-triazin-2-yl, benzoxazol-2-yl, benzoisoxazol-3-yl, thiazol-2-yl, 5-trifluoromethyl-1,3,4-thiadiazol-2-yl and benzothiazol-2-yl;

r is an integer from 1 to 2;

$R^2$ is absent or is oxido;

Z is selected from the group consisting of 4-(N-methyl-N-cyclohexyl-amino)-phenyl, 4-(pyrrolidin-1-yl)-phenyl, 4-(1-azepanyl)-phenyl, 4-(3-trifluoromethyl-phenyl)-phenyl, 4-(4-methoxyphenyl)-phenyl, 4-cyclohexyl-phenyl, 4-(N-(2-iodobenzyl)-amino)-phenyl, 4-(2-chlorophenyl)-phenyl, 4-(4-fluorophenyl)-phenyl, 4-(3,4-dichlorophenyl)-phenyl, biphen-4-yl, 4-(N-methyl-N-phenyl-amino)-phenyl, 4-(4-iodophenyl)-phenyl, 4-phenyloxy-phenyl 4-(N-(5-iodo-furan-2-ylmethyl)amino)-phenyl, 4-benzyl-phenyl, 4-(pyrrol-1-yl)-phenyl, 4-(3-fluorophenyl)-phenyl, 4-(N-cyclohexylcarbonyl-amino)-phenyl, 4-dimethylamino-phenyl, 4-butyl-phenyl, 4-diethylamino-phenyl, 3-iodo-4-methoxy-phenyl, 3-iodo-4-chloro-phenyl, 4-(1,1-dimethylpropyl)-phenyl, 4-(pyrazol-1-yl)-phenyl, 3-(phenyloxy)-phenyl, 3-iodo-4-methyl-phenyl, 3-methyl-4-iodo-phenyl, 3-(4-fluorophenyl)-phenyl, 4-iodophenyl, 2-(benzyloxy)-phenyl, biphen-3-yl, 4-(imidazol-1-yl)-phenyl, 4-(phenylcarbonyl)-phenyl, 2-(isoindolyl-1,3-dione)-phenyl, 3-(2,3-dihydro-1H-isoindol-2-yl)-phenyl, 3-(phenylcarbonyl)-phenyl, 4-nitrophenyl, 4-(1-t-butoxycarbonyl-piperidin-4-yl)-phenyl, 4-(1-t-butoxycarbonyl-piperidin-4-yl)oxy)-phenyl, 1,1,4,4,tetramethyl-1,2,3,4-tetrahydro-naphth-6-yl-ethyl, 6-methoxy-naphth-2-yl, 1,2,3,4-tetrahydronaphth-2-yl, 2-(9-oxo-fluorenyl), fluoren-2-yl, 4-(N-methyl-N-cyclohexylmethyl-amino)-phenylethyl, 4-iodo-phenylethyl, 4-(t-butyl)-phenylethyl, 3-iodo-phenylethyl,

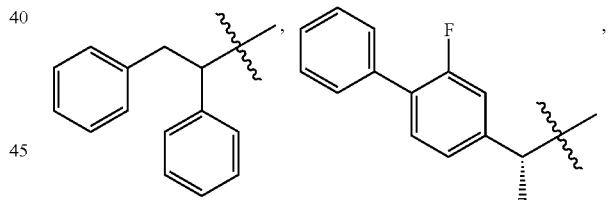

4-(trifluoromethyl-thio)-phenyl-ethenyl, 4-isopropyl-phenyl-ethenyl, 3-trifluoromethyl-phenyl-ethenyl, 3-ethoxy-phenyl-ethenyl, 4-(n-pentyl)-cyclohexyl, 4-(t-butyl)-cyclohexyl, 4-pentyl-bicyclo[2.2.2]oct-1-yl, 2-cyclohexyl-benzoxazol-6-yl, 2-methyl-3-phenyl-benzimidazol-6-yl, 1-isopropyl-2-trifluoromethyl-benzimidazol-4-yl, 1-cyclohexyl-2-methyl-benzimidazol-4-yl, 1-propyl-indol-5-yl, 1-(2,4-dichlorophenyl)-4-methyl-5-(4-chlorophenyl)-pyrazol-3-yl, 2-phenyl-benzimidazol-5-yl, 4-phenyl-5-trifluoromethyl-thien-2-yl, 5-benzyloxy-indol-2-yl, 1-(2,4-dichlorophenyl)-5-(4-chlorophenyl)-pyrazol-3-yl, 1,5-diphenyl-pyrazol-3-yl, 1-(4-aminosulfonyl-phenyl)-5-(4-chlorophenyl)-pyrazol-3-yl, 5-(3-trifluoro-methyl-phenyl)-furan-2-yl), 5-(4-methylphenyl)-furan-2-yl, 5-(4-methoxyphenyl)-furan-2-yl, 1,2,3,4-tetrahydro-quinolin-6-yl, 5-phenyl-furan-2-yl, 1-phenyl-pyrazol-4-yl, 2-phenyl-5-trifluoromethyl-oxazol-4-yl, quinolin-6-yl, quinolin-2-yl, 3-methyl-benzofuran-2-yl, 5-butyl-pyrid-2-yl, 4-benzyloxy-indol-2-yl, indol-5-yl, 5-(phenylethynyl)-furan-2-yl, 5-(3,5- dichlorophenyloxy)-furan-2-yl, xanthen-3-yl-9-one, 1-phenyl-1,2,3,4-tetrhydro-quiunolin-6-yl, 1-(4-trifluoromethyl-phenyl)-1,2,3,4-tetrahydro-quinolin-6-yl, 1-(3-trifluoromethyl-phenyl)-1,2,3,4-tetrahydro-quinolin-6-yl, (1-cyclohexyl-indolin-5-yl)-ethenyl- and 6-trifluoromethyl-benzo[b]thien-2yl;

or an enantiomer, diastereomer or pharmaceutically acceptable salts thereof;

with the proviso that the compound of formula (I) is other than a compound wherein Y is 3-methylpyridin-2-yl, r is 1, and $R^2$ is absent and Z is 4-biphenyl;

a compound wherein Y is 5-cyanopyridin-2-yl, r is 1, and $R^2$ is absent and Z is 4-biphenyl;

a compound wherein Y is pyrimidin-2-yl, r is 2, and $R^2$ is absent and Z is 2-(4-trifluoromethylthiophenyl)-vinyl;

a compound wherein Y is pyridin-2-yl, r is 1, and $R^2$ is absent and Z is 2-cyclohexyl-benzoxazol-6-yl;

a compound wherein Y is pyrimidin-2-yl, r is 1, and $R^2$ is absent and Z is 2-cyclohexyl-benzoxazol-6-yl; or a compound wherein Y is 3-trifluoromethylphenyl, r is 1, and $R^2$ is absent and Z is 1,2,3,4-tetrahydroquinolin-6-yl.

5. A compound as in claim 1, wherein

Y is selected from the group consisting of pyrid-2-yl-, 3-cyano-pyrid-2-yl, 5-chloro-pyrid-2-yl, pyrimidin-2-yl, thiazol-2-yl, 5-trifluoromethyl-1,3,4-thiadiazol-2-yl, 1,3,5-triazin-2-yl and benzisoxazol-2-yl;

r is 1;

$R^2$ is absent;

Z is selected from the group consisting of 4-(N-methyl-N-cyclohexyl-amino)-phenyl, 4-(pyrrolidin-1-yl)-phenyl, 4-(1-azepanyl)-phenyl, 4-(3-trifluoromethyl-phenyl)-phenyl, 4-(4-methoxyphenyl)-phenyl, 4-cyclohexyl-phenyl, 4-(N-(2-iodobenzyl)-amino)-phenyl, 4-(2-chlorophenyl)-phenyl, 4-(4-fluorophenyl)-phenyl, 4-(3,4-dichlorophenyl)-phenyl, biphen-4-yl, 4-(N-methyl-N-phenyl-amino)-phenyl, 4-(4-iodophenyl)-phenyl, 4-phenyloxy-phenyl, 4-(N-(5-iodo-furan-2-ylmethyl) amino)-phenyl, 4-benzyl-phenyl, 4-(pyrrol-1-yl)-phenyl, 4-(3-fluorophenyl)-phenyl, 4-(N-cyclohexylcarbonyl-amino)-phenyl, 4-dimethylamino-phenyl, 4-butyl-phenyl, 4-diethylamino-phenyl, 3-iodo-4-methoxy-phenyl, 3-iodo-4-chloro-phenyl, 4-(1,1-dimethyl-propyl)-phenyl, 4-(pyrazol-1-yl)-phenyl, 3-(phenyloxy)-phenyl, 3-iodo-4-methyl-phenyl, 3-methyl-4-iodo-phenyl, 3-(4-fluorophenyl)-phenyl, 4-iodophenyl, 2-(benzyloxy)-phenyl, 4-benzyloxy-phenyl, 4-(1-t-butoxycarbonyl-piperidin-4-yl)-phenyl, 4-(1-t-butoxycarbonyl-piperidin-4-yl)oxy)-phenyl, 1,1,4,4,tetramethyl-1,2,3,4-tetrahydro-naphth-6-yl-ethyl, 6-methoxy-naphth-2-yl, 2-(9-oxo-fluorenyl), 4-(N-methyl-N-cyclohexylmethyl-amino)-phenylethyl, 4-iodophenylethyl, 4-(t-butyl)-phenylethyl, 4-(trifluoromethyl-thio)-phenyl-ethenyl, 4-(n-pentyl)-cyclohexyl, 2-cyclohexyl-benzoxazol-6-yl, 2-methyl-3-phenyl-benzimidazol-6-yl, 1-isopropyl-2-trifluoromethyl-benzimidazol-4-yl, 1-cyclohexyl-2-methyl-benzimidazol-4-yl, 1-propyl-indol-5-yl, 2-phenyl-benzimidazol-5-yl, 4-phenyl-5-trifluoromethyl-thien-2-yl, xanthen-3-yl-9-one, 1-(2,4-dichlorophenyl)-4-methyl-5-(4-chlorophenyl)-pyrazol-3-yl and 6-trifluoromethyl-benzo[b]thien-2-yl;

or an enantiomer, diastereomer or pharmaceutically acceptable salts thereof;

with the proviso that the compound of formula (I) is other than a compound wherein Y is pyrid-2-yl, r is 1, $R^2$ is absent and Z is 2-cyclohexyl-benzoxazol-6-yl or a compound wherein Y is pyrimidin-2-yl, r is 1, and $R^2$ is absent and Z is 2-cyclohexyl-benzoxazol-6-yl.

6. A compound as in claim 1, wherein

Y is selected from the group consisting of pyrid-2-yl, 3-cyano-pyrid-2-yl, pyrimidin-2-yl, 1,3,5-triazin-2-yl, thiazol-2-yl, 5-trifluoromethyl-1,3,4-thiadiazol-2-yl and benzisoxazol-3-yl;

r is 1;

$R^2$ is absent;

Z is selected from the group consisting of 4-(N-methyl-N-cyclohexyl-amino)-phenyl, 4-(pyrrolidin-1-yl)-phenyl, 4-(1-azepanyl)-phenyl, 4-(3-trifluoromethyl-phenyl)-phenyl, 4-(4-methoxyphenyl)-phenyl, 4-cyclohexyl-phenyl, 4-(N-(2-iodobenzyl)-amino)-phenyl, 4-(2-chlorophenyl)-phenyl, 4-(4-fluorophenyl)-phenyl, 4-(3,4-dichlorophenyl)-phenyl, biphen-4-yl, 4-(N-methyl-N-phenyl-amino)-phenyl, 4-(4-iodophenyl)-phenyl, 4-phenyloxy-phenyl, 4-(N-(5-iodo-furan-2-ylmethyl) amino)-phenyl, 4-benzyl-phenyl, 4-(pyrrol-1-yl)-phenyl, 4-(3-fluorophenyl)-phenyl, 4-(N-cyclohexylcarbonyl-amino)-phenyl, 4-dimethylamino-phenyl, 4-diethylamino-phenyl, 4-benzyloxy-phenyl, 2-cyclohexyl-benzoxazol-6-yl, 2-methyl-3-phenyl-benzimidazol-6-yl, 1-isopropyl-2-trifluoromethyl-benzimidazol-4-yl, 1-cyclohexyl-2-methyl-benzimidazol-4-yl, 1-propyl-indol-5-yl and 6-trifluoromethyl-benzo[b]thien-2-yl;

or an enantiomer, diastereomer or pharmaceutically acceptable salts thereof;

with the proviso that the compound of formula (I) is other than a compound wherein Y is pyrid-2-yl, r is 1, $R^2$ is absent and Z is 2-cyclohexyl-benzoxazol-6-yl or a compound wherein Y is pyrimidin-2-yl, r is 1, and $R^2$ is absent and Z is 2-cyclohexyl-benzoxazol-6-yl.

7. A compound as in claim 1, wherein

Y is selected from the group consisting of pyrid-2-yl, 3-cyano-pyrid-2-yl, pyrimidin-2-yl and thiazol-2-yl;

r is 1;

$R^2$ is absent;

Z is selected from the group consisting of 4-(N-methyl,N-cyclohexyl-amino)-phenyl, 4-(pyrrolidin-1-yl)-phenyl, 4-(1-azepanyl)-phenyl, 4-(3-trifluoromethyl-phenyl)-phenyl, 4-(4-methoxyphenyl)-phenyl, 4-(2-chlorophenyl)-phenyl, 4-(4-fluorophenyl)-phenyl, 4-(3,4-dichlorophenyl)-phenyl, biphen-4-yl, 4-(N-methyl-N-phenyl-amino)-phenyl, 4-phenyloxy-phenyl, 4-cyclohexyl-phenyl, 4-benzyl-phenyl, 4-(pyrrol-1-yl)-phenyl, 4-(3-fluorophenyl)-phenyl, 4-(N-cyclohexylcarbonyl-amino)-phenyl, 4-dimethylamino-phenyl, 4-butyl-phenyl, 4-diethylamino-phenyl, 3-(4-fluorophenyl)-phenyl, 4-benzyloxy-phenyl, 4-(1-t-butoxycarbonyl-piperidin-4-yl)-phenyl, 1,1,4,4,tetramethyl-1,2,3,4-tetrahydro-naphth-6-yl-ethyl, 4-(N-methyl-N-cyclohexylmethyl-amino)-phenylethyl, 4-(trifluoromethyl-thio)-phenyl-ethenyl, 2-methyl-3-phenyl-benzimidazol-6-yl, 1-isopropyl-2-trifluoromethyl-benzimidazol-4-yl, 1-cyclohexyl-2-methyl-benzimidazol-4-yl, 1-propyl-indol-5-yl and 1-(2,4-dichlorophenyl)-4-methyl-5-(4-chlorophenyl)-pyrazol-3-yl;

or an enantiomer, diastereomer or pharmaceutically acceptable salts thereof.

8. A compound as in claim 1, wherein

Y is selected from the group consisting of pyrid-2-yl, pyrimidin-2-yl, thiazol-2-yl and benzisoxazol-2-yl;

r is 1;

R² is absent;

Z is selected from the group consisting of 4-cyclohexyl-phenyl, biphen-4-yl, 4-(N-cyclohexylcarbonyl-amino)-phenyl, 4-benzylphenyl, 4-diethylaminophenyl, 3-iodo-4-methoxy-phenyl, 3-(4-fluorophenyl)-phenyl, 4-(3-fluorophenyl)-phenyl, 4-(N-methyl-N-cyclohexylmethyl-amino)phenyl, 9-oxo-fluoren-2-yl and 2-cyclohexyl-benzooxazol-6-yl;

or an enantiomer, diastereomer or pharmaceutically acceptable salts thereof;

with the proviso that the compound of formula (I) is other than a compound wherein Y is pyrid-2-yl, r is 1, R² is absent and Z is 2-cyclohexyl-benzoxazol-6-yl or a compound wherein Y is pyrimidin-2-yl, r is 1, and R² is absent and Z is 2-cyclohexyl-benzoxazol-6-yl.

9. A pharmaceutical composition comprising a pharmaceutically acceptable carrier and a compound of claim 1.

10. A pharmaceutical composition made by mixing a compound of claim 1 and a pharmaceutically acceptable carrier.

11. A process for making a pharmaceutical composition comprising mixing a compound of claim 1 and a pharmaceutically acceptable carrier.

12. A method of treating or ameliorating a disease, syndrome, condition or disorder that is affected by inhibition of MGL, comprising administering to a subject in need thereof a therapeutically effective amount of a compound of claim 1, wherein the disease, syndrome, condition or disorder is selected from the group consisting of pain, inflammatory pain, and neuropathic pain.

13. A method as in claim 12, wherein the disease, syndrome, condition or disorder that is affected by inhibition of MGL is pain.

14. A method as in claim 13, wherein the disease, syndrome, condition or disorder that is affected by inhibition of MGL is inflammatory pain.

15. A method as in claim 12, wherein the disease, syndrome, condition or disorder that is affected by inhibition of MGL is visceral pain.

16. A method as in claim 12, wherein the disease, syndrome, condition or disorder that is affected by inhibition of MGL is neuropathic pain.

17. A method as in claim 12, wherein the disease, syndrome, condition or disorder that is affected by inhibition of MGL is neuropathic cold allodynia.

18. A method as in claim 12, wherein the disease, syndrome, condition or disorder that is affected by inhibition of MGL is selected from the group consisting of inflammatory pain and neuropathic pain.

* * * * *